US 11,246,704 B2

(12) United States Patent
Hariton et al.

(10) Patent No.: US 11,246,704 B2
(45) Date of Patent: Feb. 15, 2022

(54) PROSTHETIC HEART VALVE

(71) Applicant: CARDIOVALVE LTD., Or Yehuda (IL)

(72) Inventors: Ilia Hariton, Zichron Yaakov (IL); Meni Iamberger, Kfar Saba (IL); Aviram Baum, Tel Aviv (IL); Yelena Kasimov, Petach Tikva (IL)

(73) Assignee: CARDIOVALVE LTD., Or Yehuda (IL)

( * ) Notice: Subject to any disclaimer, the term of this patent is extended or adjusted under 35 U.S.C. 154(b) by 0 days.

(21) Appl. No.: 16/636,204

(22) PCT Filed: Jul. 4, 2018

(86) PCT No.: PCT/IL2018/050725
§ 371 (c)(1),
(2) Date: Feb. 3, 2020

(87) PCT Pub. No.: WO2019/026059
PCT Pub. Date: Feb. 7, 2019

(65) Prior Publication Data
US 2020/0246140 A1 Aug. 6, 2020

Related U.S. Application Data

(63) Continuation-in-part of application No. 15/956,956, filed on Apr. 19, 2018, now Pat. No. 10,575,948,
(Continued)

(51) Int. Cl.
*A61F 2/24* (2006.01)
(52) U.S. Cl.
CPC .......... *A61F 2/2418* (2013.01); *A61F 2/2415* (2013.01); *A61F 2/2436* (2013.01);
(Continued)

(58) Field of Classification Search
CPC .................................................... A61F 2/2415
See application file for complete search history.

(56) References Cited

U.S. PATENT DOCUMENTS 3,874,388 A 4/1975 King et al.
4,222,126 A 9/1980 Boretos et al.
(Continued)

FOREIGN PATENT DOCUMENTS

CA 2822801 8/2006
CN 103974674 8/2014
(Continued)

OTHER PUBLICATIONS

Notice of Allowance dated May 7, 2020 which issued during the prosecution of U.S. Appl. No. 16/637,166.
(Continued)

*Primary Examiner* — Jacqueline Woznicki
(74) *Attorney, Agent, or Firm* — Dilworth IP, LLC

(57) ABSTRACT

A frame assembly (222) includes a tubular portion (32) that defines a lumen along an axis; a plurality of arms (46) coupled to the tubular portion at a first axial level, each of the arms extending radially outward from the tubular portion to a respective arm-tip; and a plurality of ventricular legs (50) that are coupled to the tubular portion at a second axial level, and that extend radially outward from the tubular portion. A first sheet (440) has a greater perimeter (446), and a smaller perimeter (448) that defines an opening. The first sheet is stitched onto the plurality of arms, with the opening aligned with the lumen. Subsequently, an outer perimeter (454) of a second sheet (450) is stitched to the greater perimeter of the first sheet. Subsequently, the second sheet is everted by passing an inner perimeter (452) of the second sheet around the arm-tips.

16 Claims, 30 Drawing Sheets

Related U.S. Application Data which is a continuation-in-part of application No. 15/668,559, filed on Aug. 3, 2017, now Pat. No. 10,537,426.

(60) Provisional application No. 62/560,384, filed on Sep. 19, 2017.

(52) U.S. Cl.
CPC ............... *A61F 2220/0008* (2013.01); *A61F 2250/0003* (2013.01)

(56) References Cited

U.S. PATENT DOCUMENTS

| | | |
|---|---|---|
| 4,261,342 A | 4/1981 | Aranguren |
| 4,275,469 A | 6/1981 | Gabbay |
| 4,340,091 A | 7/1982 | Skelton et al. |
| 4,423,525 A | 1/1984 | Vallana et al. |
| 4,853,986 A | 8/1989 | Allen |
| 4,892,541 A | 1/1990 | Alonso |
| 4,972,494 A | 11/1990 | White et al. |
| 4,994,077 A | 2/1991 | Dobben |
| 5,078,739 A | 1/1992 | Martin |
| 5,108,420 A | 4/1992 | Marks |
| 5,314,473 A | 5/1994 | Godin |
| 5,332,402 A | 7/1994 | Teitelbaum |
| 5,397,351 A | 3/1995 | Pavcnik et al. |
| 5,405,378 A | 4/1995 | Strecker |
| 5,443,500 A | 8/1995 | Sigwart |
| 5,473,812 A | 12/1995 | Morris et al. |
| 5,607,444 A | 3/1997 | Lam |
| 5,607,470 A | 3/1997 | Milo |
| 5,647,857 A | 7/1997 | Anderson et al. |
| 5,702,397 A | 12/1997 | Goble et al. |
| 5,713,948 A | 2/1998 | Uflacker |
| 5,716,417 A | 2/1998 | Girard et al. |
| 5,741,297 A | 4/1998 | Simon |
| 5,765,682 A | 6/1998 | Bley et al. |
| 5,776,140 A | 7/1998 | Cottone |
| 5,868,777 A | 2/1999 | Lam |
| 5,873,906 A | 2/1999 | Lau et al. |
| 5,954,766 A | 9/1999 | Zadno-Azizi et al. |
| 5,957,949 A | 9/1999 | Leonhardt et al. |
| 5,980,565 A | 11/1999 | Jayaraman |
| 6,010,530 A | 1/2000 | Goicoechea |
| 6,019,787 A | 2/2000 | Richard et al. |
| 6,042,607 A | 3/2000 | Williamson, IV |
| 6,059,827 A | 5/2000 | Fenton |
| 6,074,417 A | 6/2000 | Peredo |
| 6,113,612 A | 9/2000 | Swanson et al. |
| 6,120,534 A | 9/2000 | Ruiz |
| 6,126,686 A * | 10/2000 | Badylak .............. A61L 27/3691 623/1.24 |
| 6,152,937 A | 11/2000 | Peterson et al. |
| 6,165,183 A | 12/2000 | Kuehn et al. |
| 6,165,210 A | 12/2000 | Lau et al. |
| 6,187,020 B1 | 2/2001 | Zegdi et al. |
| 6,193,745 B1 | 2/2001 | Fogarty et al. |
| 6,264,700 B1 | 7/2001 | Kilcoyne et al. |
| 6,287,339 B1 | 9/2001 | Vasquez et al. |
| 6,312,465 B1 | 11/2001 | Griffin et al. |
| 6,332,893 B1 | 12/2001 | Mortier et al. |
| 6,334,873 B1 | 1/2002 | Lane et al. |
| 6,346,074 B1 | 2/2002 | Roth |
| 6,350,278 B1 | 2/2002 | Lenker et al. |
| 6,352,561 B1 | 3/2002 | Leopold et al. |
| 6,391,036 B1 | 5/2002 | Berg et al. |
| 6,402,780 B2 | 6/2002 | Williamson, IV |
| 6,409,755 B1 | 6/2002 | Vrba |
| 6,419,696 B1 | 7/2002 | Ortiz et al. |
| 6,428,550 B1 | 8/2002 | Vargas et al. |
| 6,440,164 B1 | 8/2002 | Dimatteo et al. |
| 6,454,799 B1 | 9/2002 | Schreck |
| 6,458,153 B1 | 10/2002 | Bailey et al. |
| 6,482,228 B1 | 11/2002 | Norred |
| 6,511,491 B2 | 1/2003 | Grudem et al. |
| 6,530,952 B2 | 3/2003 | Vesely |
| 6,540,782 B1 | 4/2003 | Snyders |
| 6,551,350 B1 | 4/2003 | Thornton et al. |
| 6,558,396 B1 | 5/2003 | Inoue |
| 6,558,418 B2 | 5/2003 | Carpentier et al. |
| 6,569,196 B1 | 5/2003 | Vesely |
| 6,602,263 B1 | 8/2003 | Swanson et al. |
| 6,616,675 B1 | 9/2003 | Evard et al. |
| 6,652,556 B1 | 11/2003 | VanTassel et al. |
| 6,669,724 B2 | 12/2003 | Park et al. |
| 6,682,558 B2 | 1/2004 | Tu et al. |
| 6,699,256 B1 | 3/2004 | Logan et al. |
| 6,716,244 B2 | 4/2004 | Klaco |
| 6,719,781 B1 | 4/2004 | Kim |
| 6,719,788 B2 | 4/2004 | Cox |
| 6,730,118 B2 | 5/2004 | Spenser et al. |
| 6,730,121 B2 | 5/2004 | Ortiz et al. |
| 6,733,525 B2 | 5/2004 | Yang et al. |
| 6,752,813 B2 | 6/2004 | Goldfarb et al. |
| 6,764,518 B2 | 7/2004 | Godin |
| 6,767,362 B2 | 7/2004 | Schreck |
| 6,797,002 B2 | 9/2004 | Spence et al. |
| 6,821,297 B2 | 11/2004 | Snyders |
| 6,830,585 B1 | 12/2004 | Artof et al. |
| 6,830,638 B2 | 12/2004 | Boylan et al. |
| 6,893,460 B2 | 5/2005 | Spenser et al. |
| 6,926,715 B1 | 8/2005 | Hauck et al. |
| 6,951,571 B1 | 10/2005 | Srivastava |
| 6,960,217 B2 | 11/2005 | Bolduc |
| 6,964,684 B2 | 11/2005 | Ortiz et al. |
| 6,974,476 B2 | 12/2005 | McGuckin et al. |
| 7,011,681 B2 | 3/2006 | Vesely |
| 7,018,406 B2 | 3/2006 | Seguin et al. |
| 7,041,132 B2 | 5/2006 | Quijano et al. |
| 7,077,861 B2 | 7/2006 | Spence |
| 7,101,395 B2 | 9/2006 | Tremulis et al. |
| 7,101,396 B2 | 9/2006 | Artof et al. |
| 7,137,184 B2 | 11/2006 | Schreck |
| 7,172,625 B2 | 2/2007 | Shu et al. |
| 7,175,656 B2 | 2/2007 | Khairkhahan |
| 7,198,646 B2 | 4/2007 | Figulla et al. |
| 7,201,772 B2 | 4/2007 | Schwammenthal |
| 7,226,467 B2 | 6/2007 | Lucatero et al. |
| 7,226,477 B2 | 6/2007 | Cox |
| 7,288,097 B2 | 10/2007 | Séguin |
| 7,288,111 B1 | 10/2007 | Holloway et al. |
| 7,316,716 B2 | 1/2008 | Egan |
| 7,329,279 B2 | 2/2008 | Haug et al. |
| 7,335,213 B1 | 2/2008 | Hyde et al. |
| 7,351,256 B2 | 4/2008 | Hojeibane et al. |
| 7,374,573 B2 | 5/2008 | Gabbay |
| 7,377,938 B2 | 5/2008 | Sarac et al. |
| 7,381,218 B2 | 6/2008 | Schreck |
| 7,381,219 B2 | 6/2008 | Salahieh et al. |
| 7,404,824 B1 | 7/2008 | Webler et al. |
| 7,422,603 B2 | 9/2008 | Lane |
| 7,429,269 B2 | 9/2008 | Schwammenthal |
| 7,442,204 B2 | 10/2008 | Schwammenthal |
| 7,445,630 B2 | 11/2008 | Lashinski et al. |
| 7,455,677 B2 | 11/2008 | Vargas et al. |
| 7,455,688 B2 | 11/2008 | Furst et al. |
| 7,462,162 B2 | 12/2008 | Phan et al. |
| 7,481,838 B2 | 1/2009 | Carpentier et al. |
| 7,510,575 B2 | 3/2009 | Spenser et al. |
| 7,513,909 B2 | 4/2009 | Lane et al. |
| 7,524,331 B2 | 4/2009 | Birdsall |
| 7,527,646 B2 | 5/2009 | Randert et al. |
| 7,556,632 B2 | 7/2009 | Zadno |
| 7,556,646 B2 | 7/2009 | Yang et al. |
| 7,563,267 B2 | 7/2009 | Goldfarb et al. |
| 7,563,273 B2 | 7/2009 | Goldfarb et al. |
| 7,582,111 B2 | 9/2009 | Krolik et al. |
| 7,585,321 B2 | 9/2009 | Cribier |
| 7,597,711 B2 | 10/2009 | Drews et al. |
| 7,608,091 B2 | 10/2009 | Goldfarb et al. |
| 7,611,534 B2 | 11/2009 | Kapadia et al. |
| 7,621,948 B2 | 11/2009 | Hermann et al. |

(56) References Cited

U.S. PATENT DOCUMENTS

| | | |
|---|---|---|
| 7,625,403 B2 | 12/2009 | Krivoruchko |
| 7,632,302 B2 | 12/2009 | Vreeman et al. |
| 7,635,329 B2 | 12/2009 | Goldfarb et al. |
| 7,648,528 B2 | 1/2010 | Styrc |
| 7,655,015 B2 | 2/2010 | Goldfarb et al. |
| 7,666,204 B2 | 2/2010 | Thornton et al. |
| 7,682,380 B2 | 3/2010 | Thornton et al. |
| 7,708,775 B2 | 5/2010 | Rowe et al. |
| 7,717,952 B2 | 5/2010 | Case et al. |
| 7,717,955 B2 | 5/2010 | Lane et al. |
| 7,731,741 B2 | 6/2010 | Eidenschink |
| 7,736,388 B2 | 6/2010 | Goldfarb et al. |
| 7,748,389 B2 | 7/2010 | Salahieh et al. |
| 7,753,922 B2 | 7/2010 | Starksen |
| 7,758,595 B2 | 7/2010 | Allen et al. |
| 7,758,632 B2 | 7/2010 | Hojeibane et al. |
| 7,758,640 B2 | 7/2010 | Vesely |
| 7,771,467 B2 | 8/2010 | Svensson |
| 7,771,469 B2 | 8/2010 | Liddicoat |
| 7,776,083 B2 | 8/2010 | Vesely |
| 7,780,726 B2 | 8/2010 | Seguin |
| 7,785,341 B2 | 8/2010 | Forster et al. |
| 7,799,069 B2 | 9/2010 | Bailey et al. |
| 7,803,181 B2 | 9/2010 | Furst et al. |
| 7,811,296 B2 | 10/2010 | Goldfarb et al. |
| 7,811,316 B2 | 10/2010 | Kalmann et al. |
| 7,824,442 B2 | 11/2010 | Salahieh et al. |
| 7,837,645 B2 | 11/2010 | Bessler et al. |
| 7,837,727 B2 | 11/2010 | Goetz et al. |
| 7,842,081 B2 | 11/2010 | Yadin |
| 7,850,725 B2 | 12/2010 | Vardi et al. |
| 7,871,432 B2 | 1/2011 | Bergin |
| 7,871,436 B2 | 1/2011 | Ryan et al. |
| 7,887,583 B2 | 2/2011 | Macoviak |
| 7,892,281 B2 | 2/2011 | Seguin et al. |
| 7,896,915 B2 | 3/2011 | Guyenot et al. |
| 7,914,544 B2 | 3/2011 | Nguyen et al. |
| 7,914,569 B2 | 3/2011 | Nguyen et al. |
| 7,927,370 B2 | 4/2011 | Webler et al. |
| 7,942,927 B2 | 5/2011 | Kaye et al. |
| 7,947,072 B2 | 5/2011 | Yang et al. |
| 7,947,075 B2 | 5/2011 | Goetz et al. |
| 7,951,195 B2 | 5/2011 | Antonsson et al. |
| 7,955,375 B2 | 6/2011 | Agnew |
| 7,955,377 B2 | 6/2011 | Melsheimer |
| 7,955,384 B2 | 6/2011 | Rafiee et al. |
| 7,959,666 B2 | 6/2011 | Salahieh et al. |
| 7,959,672 B2 | 6/2011 | Salahieh et al. |
| 7,967,833 B2 | 6/2011 | Sterman et al. |
| 7,967,857 B2 | 6/2011 | Lane |
| 7,981,151 B2 | 7/2011 | Rowe |
| 7,981,153 B2 | 7/2011 | Fogarty et al. |
| 7,992,567 B2 | 8/2011 | Hirotsuka et al. |
| 7,993,393 B2 | 8/2011 | Carpentier et al. |
| 8,002,825 B2 | 8/2011 | Letac et al. |
| 8,002,826 B2 | 8/2011 | Seguin |
| 8,016,877 B2 | 9/2011 | Seguin et al. |
| 8,016,882 B2 | 9/2011 | Macoviak |
| 8,021,420 B2 | 9/2011 | Dolan |
| 8,021,421 B2 | 9/2011 | Fogarty et al. |
| 8,025,695 B2 | 9/2011 | Fogarty et al. |
| 8,029,518 B2 | 10/2011 | Goldfarb et al. |
| 8,029,557 B2 | 10/2011 | Sobrino-Serrano et al. |
| 8,029,564 B2 | 10/2011 | Johnson et al. |
| 8,034,104 B2 | 10/2011 | Carpentier et al. |
| 8,038,720 B2 | 10/2011 | Wallace et al. |
| 8,043,360 B2 | 10/2011 | McNamara et al. |
| 8,048,138 B2 | 11/2011 | Sulivan et al. |
| 8,048,140 B2 | 11/2011 | Purdy |
| 8,048,153 B2 | 11/2011 | Salahieh et al. |
| 8,052,592 B2 | 11/2011 | Goldfarb et al. |
| 8,052,741 B2 | 11/2011 | Bruszewski et al. |
| 8,052,749 B2 | 11/2011 | Salahieh et al. |
| 8,057,493 B2 | 11/2011 | Goldfarb et al. |
| 8,057,532 B2 | 11/2011 | Hoffman |
| 8,057,540 B2 | 11/2011 | Letac et al. |
| 8,062,355 B2 | 11/2011 | Figulla et al. |
| 8,062,359 B2 | 11/2011 | Marquez et al. |
| 8,070,708 B2 | 12/2011 | Rottenberg et al. |
| 8,070,800 B2 | 12/2011 | Lock et al. |
| 8,070,802 B2 | 12/2011 | Lamphere et al. |
| 8,070,804 B2 | 12/2011 | Hyde |
| 8,075,611 B2 | 12/2011 | Milwee et al. |
| 8,080,054 B2 | 12/2011 | Rowe |
| 8,083,793 B2 | 12/2011 | Lane et al. |
| D652,927 S | 1/2012 | Braido et al. |
| D653,341 S | 1/2012 | Braido et al. |
| 8,092,518 B2 | 1/2012 | Schreck |
| 8,092,520 B2 | 1/2012 | Quadri |
| 8,092,521 B2 | 1/2012 | Figulla et al. |
| 8,105,377 B2 | 1/2012 | Liddicoat |
| 8,109,996 B2 | 2/2012 | Stacchino et al. |
| 8,118,866 B2 | 2/2012 | Herrmann et al. |
| 8,133,270 B2 | 3/2012 | Kheradvar et al. |
| 8,136,218 B2 | 3/2012 | Millwee et al. |
| 8,137,398 B2 | 3/2012 | Tuval et al. |
| 8,142,492 B2 | 3/2012 | Forster et al. |
| 8,142,494 B2 | 3/2012 | Randert et al. |
| 8,142,496 B2 | 3/2012 | Berreklouw |
| 8,142,497 B2 | 3/2012 | Friedman |
| 8,147,504 B2 | 4/2012 | Ino et al. |
| 8,157,852 B2 | 4/2012 | Bloom et al. |
| 8,157,853 B2 | 4/2012 | Laske et al. |
| 8,157,860 B2 | 4/2012 | McNamara et al. |
| 8,163,008 B2 | 4/2012 | Wilson et al. |
| 8,163,014 B2 | 4/2012 | Lane et al. |
| D660,433 S | 5/2012 | Braido et al. |
| D660,967 S | 5/2012 | Braido et al. |
| 8,167,894 B2 | 5/2012 | Miles et al. |
| 8,167,932 B2 | 5/2012 | Bourang et al. |
| 8,167,935 B2 | 5/2012 | McGuckin, Jr. et al. |
| 8,172,896 B2 | 5/2012 | McNamara et al. |
| 8,172,898 B2 | 5/2012 | Alferness et al. |
| 8,177,836 B2 | 5/2012 | Lee et al. |
| 8,182,528 B2 | 5/2012 | Salahieh et al. |
| 8,211,169 B2 | 7/2012 | Lane et al. |
| 8,216,256 B2 | 7/2012 | Raschdorf, Jr. et al. |
| 8,216,301 B2 | 7/2012 | Bonhoeffer et al. |
| 8,221,492 B2 | 7/2012 | Case et al. |
| 8,221,493 B2 | 7/2012 | Boyle et al. |
| 8,226,710 B2 | 7/2012 | Nguyen et al. |
| 8,231,670 B2 | 7/2012 | Salahieh et al. |
| 8,236,045 B2 | 8/2012 | Benichou et al. |
| 8,236,049 B2 | 8/2012 | Rowe et al. |
| 8,252,042 B2 | 8/2012 | McNamara et al. |
| 8,252,051 B2 | 8/2012 | Chau et al. |
| 8,252,052 B2 | 8/2012 | Salahieh et al. |
| 8,257,390 B2 | 9/2012 | Carley et al. |
| 8,267,988 B2 | 9/2012 | Hamer et al. |
| 8,277,501 B2 | 10/2012 | Chalekian et al. |
| 8,287,591 B2 | 10/2012 | Keidar et al. |
| 8,298,280 B2 | 10/2012 | Yadin et al. |
| 8,303,653 B2 | 11/2012 | Bonhoeffer et al. |
| 8,308,798 B2 | 11/2012 | Pintor et al. |
| 8,317,853 B2 | 11/2012 | Agnew |
| 8,317,855 B2 | 11/2012 | Gregorich et al. |
| 8,323,335 B2 | 12/2012 | Rowe et al. |
| 8,328,868 B2 | 12/2012 | Paul et al. |
| 8,337,541 B2 | 12/2012 | Quadri et al. |
| 8,343,174 B2 | 1/2013 | Goldfarb et al. |
| 8,343,213 B2 | 1/2013 | Salahieh et al. |
| 8,348,999 B2 | 1/2013 | Kheradvar et al. |
| 8,361,144 B2 | 1/2013 | Fish et al. |
| 8,366,767 B2 | 2/2013 | Zhang |
| 8,372,140 B2 | 2/2013 | Hoffman et al. |
| 8,377,119 B2 | 2/2013 | Drews et al. |
| 8,398,708 B2 | 3/2013 | Meiri et al. |
| 8,403,981 B2 | 3/2013 | Forster et al. |
| 8,403,983 B2 | 3/2013 | Quadri et al. |
| 8,408,214 B2 | 4/2013 | Spenser |
| 8,414,644 B2 | 4/2013 | Quadri et al. |
| 8,425,593 B2 | 4/2013 | Braido et al. |
| 8,430,934 B2 | 4/2013 | Das |
| 8,444,689 B2 | 5/2013 | Zhang |

(56) References Cited

U.S. PATENT DOCUMENTS

| | | |
|---|---|---|
| 8,449,599 B2 | 5/2013 | Chau et al. |
| 8,449,625 B2 | 5/2013 | Campbell et al. |
| 8,454,686 B2 | 6/2013 | Alkhatib |
| 8,460,365 B2 | 6/2013 | Haverkost et al. |
| 8,474,460 B2 | 7/2013 | Barrett et al. |
| 8,500,821 B2 | 8/2013 | Sobrino-Serrano et al. |
| 8,512,400 B2 | 8/2013 | Tran et al. |
| 8,539,662 B2 | 9/2013 | Stacchino et al. |
| 8,540,767 B2 | 9/2013 | Zhang |
| 8,545,544 B2 | 10/2013 | Spenser et al. |
| 8,551,160 B2 | 10/2013 | Figulla et al. |
| 8,551,161 B2 | 10/2013 | Dolan |
| 8,562,672 B2 | 10/2013 | Bonhoeffer et al. |
| 8,568,475 B2 | 10/2013 | Nguyen et al. |
| 8,579,964 B2 | 11/2013 | Lane et al. |
| 8,579,965 B2 | 11/2013 | Bonhoeffer et al. |
| 8,585,755 B2 | 11/2013 | Chau et al. |
| 8,585,756 B2 | 11/2013 | Bonhoeffer et al. |
| 8,591,460 B2 | 11/2013 | Wilson et al. |
| 8,591,570 B2 | 11/2013 | Revuelta et al. |
| 8,623,075 B2 | 1/2014 | Murray et al. |
| 8,623,080 B2 | 1/2014 | Fogarty et al. |
| 8,628,569 B2 | 1/2014 | Benichou et al. |
| 8,628,570 B2 | 1/2014 | Seguin |
| 8,628,571 B1 | 1/2014 | Hacohen et al. |
| 8,652,203 B2 | 2/2014 | Quadri et al. |
| 8,652,204 B2 | 2/2014 | Quill et al. |
| 8,657,872 B2 | 2/2014 | Seguin |
| 8,663,322 B2 | 3/2014 | Keranen |
| 8,673,020 B2 | 3/2014 | Sobrino-Serrano et al. |
| 8,679,174 B2 | 3/2014 | Ottma et al. |
| 8,685,086 B2 | 4/2014 | Navia et al. |
| 8,696,742 B2 | 4/2014 | Pintor et al. |
| 8,728,155 B2 | 5/2014 | Montorfano et al. |
| 8,734,507 B2 | 5/2014 | Keranen |
| 8,747,460 B2 | 6/2014 | Tuval et al. |
| 8,771,345 B2 | 7/2014 | Tuval et al. |
| 8,784,472 B2 | 7/2014 | Eidenschink |
| 8,784,479 B2 | 7/2014 | Antonsson et al. |
| 8,784,481 B2 | 7/2014 | Alkhatib et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,801,776 B2 | 8/2014 | House et al. |
| 8,808,366 B2 | 8/2014 | Braido et al. |
| 8,840,663 B2 | 9/2014 | Salahieh et al. |
| 8,840,664 B2 | 9/2014 | Karapetian et al. |
| 8,845,722 B2 | 9/2014 | Gabbay |
| 8,852,261 B2 | 10/2014 | White |
| 8,852,272 B2 | 10/2014 | Gross et al. |
| 8,870,948 B1 | 10/2014 | Erzberger et al. |
| 8,870,949 B2 | 10/2014 | Rowe |
| 8,870,950 B2 | 10/2014 | Hacohen |
| 8,876,800 B2 | 11/2014 | Behan |
| 8,894,702 B2 | 11/2014 | Quadri et al. |
| 8,900,294 B2 | 12/2014 | Paniagua et al. |
| 8,900,295 B2 | 12/2014 | Migliazza et al. |
| 8,906,083 B2 | 12/2014 | Obermiller et al. |
| 8,911,455 B2 | 12/2014 | Quadri et al. |
| 8,911,489 B2 | 12/2014 | Ben-Muvhar |
| 8,911,493 B2 | 12/2014 | Rowe et al. |
| 8,932,343 B2 | 1/2015 | Alkhatib et al. |
| 8,961,595 B2 | 2/2015 | Alkhatib |
| 8,979,922 B2 | 3/2015 | Jayasinghe et al. |
| 8,986,370 B2 | 3/2015 | Annest |
| 8,986,373 B2 | 3/2015 | Chau et al. |
| 8,986,375 B2 | 3/2015 | Garde et al. |
| 8,992,599 B2 | 3/2015 | Thubrikar et al. |
| 8,992,604 B2 | 3/2015 | Gross et al. |
| 8,992,608 B2 | 3/2015 | Haug et al. |
| 8,998,982 B2 | 4/2015 | Richter et al. |
| 9,005,273 B2 | 4/2015 | Salahieh et al. |
| 9,011,527 B2 | 4/2015 | Li et al. |
| 9,017,399 B2 | 4/2015 | Gross et al. |
| D730,520 S | 5/2015 | Braido et al. |
| D730,521 S | 5/2015 | Braido et al. |
| 9,023,100 B2 | 5/2015 | Quadri et al. |
| 9,034,032 B2 | 5/2015 | McLean et al. |
| 9,034,033 B2 | 5/2015 | McLean et al. |
| 9,039,757 B2 | 5/2015 | McLean et al. |
| D732,666 S | 6/2015 | Nguyen et al. |
| 9,050,188 B2 | 6/2015 | Schweich et al. |
| 9,060,858 B2 | 6/2015 | Thornton et al. |
| 9,072,603 B2 | 7/2015 | Tuval et al. |
| 9,084,676 B2 | 7/2015 | Chau et al. |
| 9,095,434 B2 | 8/2015 | Rowe |
| 9,125,738 B2 | 9/2015 | Figulla et al. |
| 9,125,740 B2 | 9/2015 | Morriss et al. |
| 9,132,006 B2 | 9/2015 | Spenser et al. |
| 9,132,009 B2 | 9/2015 | Hacohen et al. |
| 9,138,312 B2 | 9/2015 | Tuval et al. |
| 9,155,619 B2 | 10/2015 | Liu et al. |
| 9,173,659 B2 | 11/2015 | Bodewadt et al. |
| 9,173,738 B2 | 11/2015 | Murray et al. |
| 9,220,594 B2 | 12/2015 | Braido et al. |
| 9,226,820 B2 | 1/2016 | Braido et al. |
| 9,226,839 B1 | 1/2016 | Kariniemi et al. |
| 9,232,995 B2 | 1/2016 | Kovalsky et al. |
| 9,241,790 B2 | 1/2016 | Lane et al. |
| 9,241,791 B2 | 1/2016 | Braido et al. |
| 9,241,792 B2 | 1/2016 | Benichou et al. |
| 9,241,794 B2 | 1/2016 | Braido et al. |
| 9,248,014 B2 | 2/2016 | Lane et al. |
| 9,289,290 B2 | 3/2016 | Alkhatib et al. |
| 9,289,291 B2 | 3/2016 | Gorman et al. |
| 9,295,550 B2 | 3/2016 | Nguyen et al. |
| 9,295,552 B2 | 3/2016 | McLean et al. |
| 9,301,836 B2 | 4/2016 | Buchbinder et al. |
| 9,308,087 B2 | 4/2016 | Lane et al. |
| D755,384 S | 5/2016 | Pesce et al. |
| 9,326,852 B2 | 5/2016 | Spenser |
| 9,326,876 B2 | 5/2016 | Acosta et al. |
| 9,345,573 B2 | 5/2016 | Nyuli et al. |
| 9,387,078 B2 | 7/2016 | Gross et al. |
| 9,421,098 B2 | 8/2016 | Gifford et al. |
| 9,427,303 B2 | 8/2016 | Liddy et al. |
| 9,427,316 B2 | 8/2016 | Schweich, Jr. et al. |
| 9,439,757 B2 | 9/2016 | Wallace et al. |
| 9,463,102 B2 | 10/2016 | Kelly |
| 9,474,599 B2 | 10/2016 | Keränen |
| 9,474,638 B2 | 10/2016 | Robinson et al. |
| 9,480,559 B2 | 11/2016 | Vidlund et al. |
| 9,492,273 B2 | 11/2016 | Wallace et al. |
| 9,498,314 B2 | 11/2016 | Behan |
| 9,498,332 B2 | 11/2016 | Hacohen et al. |
| 9,532,870 B2 | 1/2017 | Cooper et al. |
| 9,554,897 B2 | 1/2017 | Lane et al. |
| 9,554,899 B2 | 1/2017 | Granada et al. |
| 9,561,103 B2 | 2/2017 | Granada et al. |
| 9,566,152 B2 | 2/2017 | Schweich et al. |
| 9,629,716 B2 | 4/2017 | Seguin |
| 9,662,203 B2 | 5/2017 | Sheahan et al. |
| 9,681,952 B2 | 6/2017 | Hacohen et al. |
| 9,717,591 B2 | 8/2017 | Chau et al. |
| 9,743,932 B2 | 8/2017 | Amplatz et al. |
| 9,763,657 B2 | 9/2017 | Hacohen et al. |
| 9,763,817 B2 | 9/2017 | Roeder |
| 9,770,256 B2 | 9/2017 | Cohen et al. |
| D800,908 S | 10/2017 | Hariton et al. |
| 9,788,941 B2 | 10/2017 | Hacohen |
| 9,895,226 B1 | 2/2018 | Harari et al. |
| 9,974,651 B2 | 5/2018 | Hariton et al. |
| 9,987,132 B1 | 6/2018 | Hariton et al. |
| 10,010,414 B2 | 7/2018 | Cooper et al. |
| 10,076,415 B1 | 9/2018 | Metchik et al. |
| 10,098,732 B1 | 10/2018 | Hariton et al. |
| 10,105,222 B1 | 10/2018 | Metchik et al. |
| 10,111,751 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,143,552 B2 | 12/2018 | Wallace et al. |
| 10,149,761 B2 | 12/2018 | Granada et al. |
| 10,154,906 B2 | 12/2018 | Granada et al. |

(56) References Cited

U.S. PATENT DOCUMENTS

| | | |
|---|---|---|
| 10,159,570 B1 | 12/2018 | Metchik et al. |
| 10,182,908 B2 | 1/2019 | Tubishevitz et al. |
| 10,226,341 B2 | 3/2019 | Gross et al. |
| 10,231,837 B1 | 3/2019 | Metchik et al. |
| 10,238,493 B1 | 3/2019 | Metchik et al. |
| 10,245,143 B2 | 4/2019 | Gross et al. |
| 10,245,144 B1 | 4/2019 | Metchik et al. |
| 10,258,471 B2 | 4/2019 | Lutter et al. |
| 10,321,995 B1 | 6/2019 | Christianson et al. |
| 10,322,020 B2 | 6/2019 | Lam et al. |
| 10,327,895 B2 | 6/2019 | Lozonschi et al. |
| 10,376,361 B2 | 8/2019 | Gross et al. |
| 10,449,047 B2 | 10/2019 | Hariton |
| 10,507,108 B2 | 12/2019 | Delgado et al. |
| 10,507,109 B2 | 12/2019 | Metchik et al. |
| 10,524,792 B2 | 1/2020 | Hernandez et al. |
| 10,531,866 B2 | 1/2020 | Hariton et al. |
| 10,531,872 B2 | 1/2020 | Hacohen et al. |
| 10,537,426 B2 | 1/2020 | Iamberger et al. |
| 10,548,731 B2 | 2/2020 | Lashinski et al. |
| 10,575,948 B2 | 3/2020 | Iamberger et al. |
| 10,595,992 B2 | 3/2020 | Chambers |
| 10,595,997 B2 | 3/2020 | Metchik et al. |
| 10,646,342 B1 | 5/2020 | Marr et al. |
| 10,813,760 B2 | 10/2020 | Metchik et al. |
| 10,820,998 B2 | 11/2020 | Marr et al. |
| 10,888,644 B2 | 1/2021 | Ratz |
| 10,905,554 B2 | 2/2021 | Cao |
| 2001/0002445 A1 | 5/2001 | Vesely |
| 2001/0005787 A1 | 6/2001 | Oz |
| 2001/0021872 A1 | 9/2001 | Bailey et al. |
| 2001/0056295 A1 | 12/2001 | Solem |
| 2002/0013571 A1 | 1/2002 | Goldfarb et al. |
| 2002/0032481 A1 | 3/2002 | Gabbay |
| 2002/0099436 A1 | 7/2002 | Thornton et al. |
| 2002/0151970 A1 | 10/2002 | Garrison et al. |
| 2002/0177894 A1 | 11/2002 | Acosta et al. |
| 2003/0009236 A1 | 1/2003 | Godin |
| 2003/0036791 A1 | 2/2003 | Bonhoeffer et al. |
| 2003/0060875 A1 | 3/2003 | Wittens |
| 2003/0069635 A1 | 4/2003 | Cartledge |
| 2003/0074052 A1 | 4/2003 | Besselink |
| 2003/0083742 A1 | 5/2003 | Spence et al. |
| 2003/0105519 A1 | 6/2003 | Fasol et al. |
| 2003/0158578 A1 | 8/2003 | Pantages et al. |
| 2004/0010272 A1 | 1/2004 | Manetakis et al. |
| 2004/0030382 A1 | 2/2004 | St. Goar et al. |
| 2004/0039414 A1 | 2/2004 | Carley et al. |
| 2004/0093060 A1 | 5/2004 | Seguin et al. |
| 2004/0122503 A1 | 6/2004 | Campbell et al. |
| 2004/0122514 A1 | 6/2004 | Fogarty et al. |
| 2004/0133267 A1 | 7/2004 | Lane |
| 2004/0143315 A1 | 7/2004 | Bruun et al. |
| 2004/0176839 A1 | 9/2004 | Huynh et al. |
| 2004/0186558 A1 | 9/2004 | Pavcnik et al. |
| 2004/0186565 A1 | 9/2004 | Schreck |
| 2004/0186566 A1 | 9/2004 | Hindrichs et al. |
| 2004/0210244 A1 | 10/2004 | Vargas et al. |
| 2004/0210304 A1 | 10/2004 | Seguin et al. |
| 2004/0220593 A1 | 11/2004 | Greenhalgh |
| 2004/0225354 A1 | 11/2004 | Allen et al. |
| 2004/0236354 A1 | 11/2004 | Seguin |
| 2004/0249433 A1 | 12/2004 | Freitag |
| 2004/0260389 A1 | 12/2004 | Case et al. |
| 2004/0260394 A1 | 12/2004 | Douk et al. |
| 2005/0004668 A1 | 1/2005 | Aklog et al. |
| 2005/0021056 A1 | 1/2005 | St. Goar et al. |
| 2005/0027305 A1 | 2/2005 | Shiu et al. |
| 2005/0027348 A1* | 2/2005 | Case .................. A61F 2/2475 623/1.24 |
| 2005/0038494 A1 | 2/2005 | Eidenschink |
| 2005/0055086 A1 | 3/2005 | Stobie |
| 2005/0075731 A1 | 4/2005 | Artof et al. |
| 2005/0080430 A1 | 4/2005 | Wright et al. |
| 2005/0085900 A1 | 4/2005 | Case et al. |
| 2005/0137686 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137692 A1* | 6/2005 | Haug .................. A61F 2/2436 623/2.11 |
| 2005/0137695 A1 | 6/2005 | Salahieh et al. |
| 2005/0137697 A1 | 6/2005 | Salahieh et al. |
| 2005/0143809 A1 | 6/2005 | Salahieh et al. |
| 2005/0149160 A1 | 7/2005 | McFerran |
| 2005/0154443 A1 | 7/2005 | Linder et al. |
| 2005/0182483 A1 | 8/2005 | Osborne et al. |
| 2005/0182486 A1 | 8/2005 | Gabbay |
| 2005/0197695 A1 | 9/2005 | Stacchino et al. |
| 2005/0203549 A1 | 9/2005 | Realyvasquez |
| 2005/0203618 A1 | 9/2005 | Sharkawy et al. |
| 2005/0216079 A1 | 9/2005 | MaCoviak |
| 2005/0234508 A1 | 10/2005 | Cummins et al. |
| 2005/0240200 A1 | 10/2005 | Bergheim |
| 2005/0251251 A1 | 11/2005 | Cribier |
| 2005/0256566 A1 | 11/2005 | Gabbay |
| 2005/0267573 A9 | 12/2005 | Macoviak et al. |
| 2006/0004439 A1 | 1/2006 | Spenser et al. |
| 2006/0004469 A1 | 1/2006 | Sokel |
| 2006/0015171 A1 | 1/2006 | Armstrong |
| 2006/0020275 A1 | 1/2006 | Goldfarb et al. |
| 2006/0020327 A1 | 1/2006 | Lashinski et al. |
| 2006/0020333 A1 | 1/2006 | Lashinski et al. |
| 2006/0041189 A1 | 2/2006 | Vancaillie |
| 2006/0052867 A1 | 3/2006 | Revuelta et al. |
| 2006/0089627 A1 | 4/2006 | Burnett et al. |
| 2006/0111773 A1 | 5/2006 | Rittgers et al. |
| 2006/0116750 A1 | 6/2006 | Herbert et al. |
| 2006/0135964 A1 | 6/2006 | Vesley |
| 2006/0155357 A1 | 7/2006 | Melsheimer |
| 2006/0161250 A1 | 7/2006 | Shaw |
| 2006/0047297 A1 | 8/2006 | Case |
| 2006/0178700 A1 | 8/2006 | Quinn |
| 2006/0178740 A1 | 8/2006 | Stacchino et al. |
| 2006/0184203 A1 | 8/2006 | Martin et al. |
| 2006/0190036 A1 | 8/2006 | Wendel et al. |
| 2006/0190038 A1 | 8/2006 | Carley et al. |
| 2006/0195183 A1 | 8/2006 | Navia et al. |
| 2006/0195184 A1 | 8/2006 | Lane et al. |
| 2006/0201519 A1 | 9/2006 | Frazier et al. |
| 2006/0212111 A1 | 9/2006 | Case et al. |
| 2006/0229708 A1 | 10/2006 | Powell et al. |
| 2006/0241656 A1 | 10/2006 | Starksen et al. |
| 2006/0241745 A1 | 10/2006 | Solem |
| 2006/0241748 A1 | 10/2006 | Lee et al. |
| 2006/0247680 A1 | 11/2006 | Amplatz et al. |
| 2006/0253191 A1 | 11/2006 | Salahieh et al. |
| 2006/0259136 A1 | 11/2006 | Nguyen et al. |
| 2006/0259137 A1 | 11/2006 | Artof et al. |
| 2006/0271166 A1 | 11/2006 | Thill et al. |
| 2006/0271171 A1 | 11/2006 | McQuinn et al. |
| 2006/0282150 A1 | 12/2006 | Olson et al. |
| 2006/0287719 A1 | 12/2006 | Rowe et al. |
| 2007/0016288 A1 | 1/2007 | Gurskis et al. |
| 2007/0027528 A1 | 2/2007 | Agnew |
| 2007/0027549 A1 | 2/2007 | Godin |
| 2007/0038293 A1 | 2/2007 | St Goar et al. |
| 2007/0038295 A1 | 2/2007 | Case et al. |
| 2007/0043435 A1 | 2/2007 | Seguin et al. |
| 2007/0055340 A1 | 3/2007 | Pryor |
| 2007/0056346 A1 | 3/2007 | Spenser et al. |
| 2007/0078510 A1 | 4/2007 | Ryan |
| 2007/0112422 A1 | 5/2007 | Dehdashtian |
| 2007/0118151 A1 | 5/2007 | Davidson |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0173932 A1 | 7/2007 | Cali et al. |
| 2007/0197858 A1 | 8/2007 | Goldfarb et al. |
| 2007/0198077 A1 | 8/2007 | Cully et al. |
| 2007/0198097 A1 | 8/2007 | Zegdi |
| 2007/0213810 A1 | 9/2007 | Newhauser et al. |
| 2007/0213813 A1 | 9/2007 | Von Segesser et al. |
| 2007/0219630 A1 | 9/2007 | Chu |

(56) References Cited

U.S. PATENT DOCUMENTS

| | | |
|---|---|---|
| 2007/0225759 A1 | 9/2007 | Thommen et al. |
| 2007/0225760 A1 | 9/2007 | Moszner et al. |
| 2007/0233186 A1 | 10/2007 | Meng |
| 2007/0233237 A1 | 10/2007 | Krivoruchko |
| 2007/0239272 A1 | 10/2007 | Navia et al. |
| 2007/0239273 A1 | 10/2007 | Allen |
| 2007/0244546 A1 | 10/2007 | Francis |
| 2007/0255400 A1 | 11/2007 | Parravicini et al. |
| 2008/0004688 A1 | 1/2008 | Spenser et al. |
| 2008/0004697 A1 | 1/2008 | Lichtenstein et al. |
| 2008/0051703 A1 | 2/2008 | Thornton et al. |
| 2008/0071361 A1 | 3/2008 | Tuval et al. |
| 2008/0071363 A1 | 3/2008 | Tuval et al. |
| 2008/0071366 A1 | 3/2008 | Tuval et al. |
| 2008/0071369 A1 | 3/2008 | Tuval et al. |
| 2008/0077235 A1 | 3/2008 | Kirson |
| 2008/0082083 A1 | 4/2008 | Forde et al. |
| 2008/0082159 A1 | 4/2008 | Tseng et al. |
| 2008/0082166 A1 | 4/2008 | Styrc et al. |
| 2008/0086164 A1 | 4/2008 | Rowe et al. |
| 2008/0086204 A1 | 4/2008 | Rankin |
| 2008/0091261 A1 | 4/2008 | Long et al. |
| 2008/0097595 A1 | 4/2008 | Gabbay |
| 2008/0132989 A1 | 6/2008 | Snow et al. |
| 2008/0140003 A1 | 6/2008 | Bei et al. |
| 2008/0147182 A1 | 6/2008 | Righini et al. |
| 2008/0161910 A1 | 7/2008 | Revuelta et al. |
| 2008/0167705 A1 | 7/2008 | Agnew |
| 2008/0167714 A1 | 7/2008 | St. Goar et al. |
| 2008/0188929 A1 | 8/2008 | Schreck |
| 2008/0195200 A1 | 8/2008 | Vidlund et al. |
| 2008/0200980 A1 | 8/2008 | Robin et al. |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0243245 A1 | 10/2008 | Thambar et al. |
| 2008/0255580 A1 | 10/2008 | Hoffman et al. |
| 2008/0262609 A1 | 10/2008 | Gross et al. |
| 2008/0269879 A1 | 10/2008 | Sathe et al. |
| 2008/0281411 A1 | 11/2008 | Berreklouw |
| 2008/0294234 A1 | 11/2008 | Hartley et al. |
| 2009/0005863 A1 | 1/2009 | Goetz et al. |
| 2009/0036966 A1 | 2/2009 | O'Connor et al. |
| 2009/0054969 A1 | 2/2009 | Salahieh et al. |
| 2009/0088836 A1 | 4/2009 | Bishop et al. |
| 2009/0099554 A1 | 4/2009 | Forster et al. |
| 2009/0099650 A1 | 4/2009 | Bolduc et al. |
| 2009/0112159 A1 | 4/2009 | Slattery et al. |
| 2009/0125098 A1 | 5/2009 | Chuter |
| 2009/0157175 A1 | 6/2009 | Benichou |
| 2009/0171363 A1 | 7/2009 | Chocron |
| 2009/0177278 A1 | 7/2009 | Spence |
| 2009/0210052 A1 | 8/2009 | Forster et al. |
| 2009/0222081 A1 | 9/2009 | Linder et al. |
| 2009/0240320 A1 | 9/2009 | Tuval et al. |
| 2009/0241656 A1 | 10/2009 | Jacquemin |
| 2009/0248143 A1 | 10/2009 | Laham |
| 2009/0259306 A1 | 10/2009 | Rowe |
| 2009/0264859 A1 | 10/2009 | Mas |
| 2009/0264994 A1 | 10/2009 | Saadat |
| 2009/0276040 A1 | 11/2009 | Rowe et al. |
| 2009/0281619 A1 | 11/2009 | Le et al. |
| 2009/0287304 A1 | 11/2009 | Dahlgren et al. |
| 2009/0299449 A1 | 12/2009 | Styrc |
| 2009/0306768 A1 | 12/2009 | Quardi |
| 2009/0319037 A1 | 12/2009 | Rowe et al. |
| 2010/0022823 A1 | 1/2010 | Goldfarb |
| 2010/0023117 A1 | 1/2010 | Yoganathan et al. |
| 2010/0023120 A1 | 1/2010 | Holecek et al. |
| 2010/0036479 A1 | 2/2010 | Hill et al. |
| 2010/0049313 A1 | 2/2010 | Alon et al. |
| 2010/0069852 A1 | 3/2010 | Kelley |
| 2010/0076548 A1 | 3/2010 | Konno |
| 2010/0100167 A1 | 4/2010 | Bortlein et al. |
| 2010/0114299 A1 | 5/2010 | Ben Muvhar et al. |
| 2010/0131054 A1 | 5/2010 | Tuval et al. |
| 2010/0137979 A1 | 6/2010 | Tuval et al. |
| 2010/0160958 A1 | 6/2010 | Clark |
| 2010/0161036 A1 | 6/2010 | Pintor et al. |
| 2010/0161042 A1 | 6/2010 | Maisano et al. |
| 2010/0174363 A1 | 7/2010 | Castro |
| 2010/0179643 A1 | 7/2010 | Shalev |
| 2010/0179648 A1 | 7/2010 | Richter et al. |
| 2010/0179649 A1 | 7/2010 | Richter et al. |
| 2010/0217382 A1 | 8/2010 | Chau et al. |
| 2010/0222810 A1 | 9/2010 | DeBeer et al. |
| 2010/0228285 A1 | 9/2010 | Miles et al. |
| 2010/0234940 A1 | 9/2010 | Dolan |
| 2010/0249908 A1 | 9/2010 | Chau et al. |
| 2010/0249917 A1 | 9/2010 | Zhang |
| 2010/0256737 A1 | 10/2010 | Pollock et al. |
| 2010/0262232 A1 | 10/2010 | Annest |
| 2010/0280603 A1 | 11/2010 | Maisano et al. |
| 2010/0280606 A1 | 11/2010 | Naor |
| 2010/0312333 A1 | 12/2010 | Navia et al. |
| 2010/0324595 A1 | 12/2010 | Linder et al. |
| 2010/0331971 A1 | 12/2010 | Keranen et al. |
| 2011/0004227 A1 | 1/2011 | Goldfarb et al. |
| 2011/0004296 A1 | 1/2011 | Lutter et al. |
| 2011/0004299 A1 | 1/2011 | Navia et al. |
| 2011/0015729 A1 | 1/2011 | Jimenez et al. |
| 2011/0015731 A1 | 1/2011 | Carpentier et al. |
| 2011/0015739 A1 | 1/2011 | Cheung et al. |
| 2011/0021985 A1 | 1/2011 | Spargias |
| 2011/0022165 A1 | 1/2011 | Oba et al. |
| 2011/0178597 A9 | 1/2011 | Navia et al. |
| 2011/0029072 A1 | 2/2011 | Gabbay |
| 2011/0040374 A1 | 2/2011 | Goetz et al. |
| 2011/0040375 A1 | 2/2011 | Letac et al. |
| 2011/0046662 A1 | 2/2011 | Moszner et al. |
| 2011/0054466 A1 | 3/2011 | Rothstein et al. |
| 2011/0054596 A1 | 3/2011 | Taylor |
| 2011/0054598 A1 | 3/2011 | Johnson |
| 2011/0066233 A1 | 3/2011 | Thornton et al. |
| 2011/0071626 A1 | 3/2011 | Wright et al. |
| 2011/0077730 A1 | 3/2011 | Fentster |
| 2011/0082538 A1 | 4/2011 | Dahlgren et al. |
| 2011/0087322 A1 | 4/2011 | Letac et al. |
| 2011/0093063 A1 | 4/2011 | Schreck |
| 2011/0098525 A1 | 4/2011 | Kermode et al. |
| 2011/0106247 A1 | 5/2011 | Miller et al. |
| 2011/0112625 A1 | 5/2011 | Ben-Muvhar et al. |
| 2011/0112632 A1 | 5/2011 | Chau et al. |
| 2011/0113768 A1 | 5/2011 | Bauer et al. |
| 2011/0118830 A1 | 5/2011 | Liddicoat et al. |
| 2011/0125257 A1 | 5/2011 | Seguin et al. |
| 2011/0125258 A1 | 5/2011 | Centola |
| 2011/0137326 A1 | 6/2011 | Bachman |
| 2011/0137397 A1 | 6/2011 | Chau et al. |
| 2011/0137409 A1 | 6/2011 | Yang et al. |
| 2011/0137410 A1 | 6/2011 | Hacohen |
| 2011/0144742 A1 | 6/2011 | Madrid et al. |
| 2011/0166636 A1 | 7/2011 | Rowe |
| 2011/0172784 A1 | 7/2011 | Richter |
| 2011/0184510 A1 | 7/2011 | Maisano et al. |
| 2011/0190877 A1 | 8/2011 | Lane et al. |
| 2011/0190879 A1 | 8/2011 | Bobo et al. |
| 2011/0202076 A1 | 8/2011 | Richter |
| 2011/0208283 A1 | 8/2011 | Rust |
| 2011/0208293 A1 | 8/2011 | Tabor |
| 2011/0208298 A1 | 8/2011 | Tuval et al. |
| 2011/0213459 A1 | 9/2011 | Garrison et al. |
| 2011/0213461 A1 | 9/2011 | Seguin et al. |
| 2011/0218619 A1 | 9/2011 | Benichou et al. |
| 2011/0218620 A1 | 9/2011 | Meiri et al. |
| 2011/0224785 A1 | 9/2011 | Hacohen |
| 2011/0238159 A1 | 9/2011 | Guyenot et al. |
| 2011/0245911 A1 | 10/2011 | Quill et al. |
| 2011/0245917 A1 | 10/2011 | Savage et al. |
| 2011/0251675 A1 | 10/2011 | Dwork |
| 2011/0251676 A1 | 10/2011 | Sweeney et al. |
| 2011/0251678 A1 | 10/2011 | Eidenschink et al. |
| 2011/0251679 A1 | 10/2011 | Wiemeyer et al. |
| 2011/0251680 A1 | 10/2011 | Tran et al. |

(56) References Cited

U.S. PATENT DOCUMENTS

| | | |
|---|---|---|
| 2011/0251682 A1 | 10/2011 | Murray, III et al. |
| 2011/0251683 A1 | 10/2011 | Tabor |
| 2011/0257721 A1 | 10/2011 | Tabor |
| 2011/0257729 A1 | 10/2011 | Spenser et al. |
| 2011/0257736 A1 | 10/2011 | Marquez et al. |
| 2011/0257737 A1 | 10/2011 | Fogarty et al. |
| 2011/0264191 A1 | 10/2011 | Rothstein |
| 2011/0264196 A1 | 10/2011 | Savage et al. |
| 2011/0264198 A1 | 10/2011 | Murray, III et al. |
| 2011/0264199 A1 | 10/2011 | Tran et al. |
| 2011/0264200 A1 | 10/2011 | Tran et al. |
| 2011/0264201 A1 | 10/2011 | Yeung |
| 2011/0264202 A1 | 10/2011 | Murray, III et al. |
| 2011/0264203 A1 | 10/2011 | Dwork et al. |
| 2011/0264206 A1 | 10/2011 | Tabor |
| 2011/0264208 A1 | 10/2011 | Duffy et al. |
| 2011/0270276 A1 | 11/2011 | Rothstein et al. |
| 2011/0271967 A1 | 11/2011 | Mortier et al. |
| 2011/0282438 A1 | 11/2011 | Drews et al. |
| 2011/0282439 A1 | 11/2011 | Thill et al. |
| 2011/0282440 A1 | 11/2011 | Cao |
| 2011/0283514 A1 | 11/2011 | Fogarty et al. |
| 2011/0288632 A1 | 11/2011 | White |
| 2011/0288634 A1 | 11/2011 | Tuval et al. |
| 2011/0295354 A1 | 12/2011 | Bueche et al. |
| 2011/0295363 A1 | 12/2011 | Girard et al. |
| 2011/0301688 A1 | 12/2011 | Dolan |
| 2011/0301698 A1 | 12/2011 | Miller et al. |
| 2011/0301701 A1 | 12/2011 | Padala et al. |
| 2011/0301702 A1 | 12/2011 | Rust et al. |
| 2011/0306916 A1 | 12/2011 | Nitzan et al. |
| 2011/0307049 A1 | 12/2011 | Kao |
| 2011/0313452 A1 | 12/2011 | Carley et al. |
| 2011/0313515 A1 | 12/2011 | Quadri et al. |
| 2011/0319989 A1 | 12/2011 | Lane et al. |
| 2011/0319991 A1 | 12/2011 | Hariton et al. |
| 2012/0010694 A1 | 1/2012 | Lutter et al. |
| 2012/0016468 A1 | 1/2012 | Robin et al. |
| 2012/0022629 A1 | 1/2012 | Perera et al. |
| 2012/0022633 A1 | 1/2012 | Olson et al. |
| 2012/0022637 A1 | 1/2012 | Ben-Muvhar |
| 2012/0022639 A1 | 1/2012 | Hacohen et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval et al. |
| 2012/0041547 A1 | 2/2012 | Duffy et al. |
| 2012/0041551 A1 | 2/2012 | Spenser et al. |
| 2012/0046738 A1 | 2/2012 | Lau et al. |
| 2012/0046742 A1 | 2/2012 | Tuval et al. |
| 2012/0053676 A1 | 3/2012 | Ku et al. |
| 2012/0053682 A1 | 3/2012 | Kovalsky et al. |
| 2012/0053688 A1 | 3/2012 | Fogarty et al. |
| 2012/0059454 A1 | 3/2012 | Millwee et al. |
| 2012/0059458 A1 | 3/2012 | Buchbinder et al. |
| 2012/0065464 A1 | 3/2012 | Ellis et al. |
| 2012/0078237 A1 | 3/2012 | Wang et al. |
| 2012/0078353 A1 | 3/2012 | Quadri et al. |
| 2012/0078357 A1 | 3/2012 | Conklin |
| 2012/0083832 A1 | 4/2012 | Delaloye et al. |
| 2012/0083839 A1 | 4/2012 | Letac et al. |
| 2012/0083879 A1 | 4/2012 | Eberhardt et al. |
| 2012/0089223 A1 | 4/2012 | Nguyen et al. |
| 2012/0101570 A1 | 4/2012 | Tuval et al. |
| 2012/0101571 A1 | 4/2012 | Thambar et al. |
| 2012/0101572 A1 | 4/2012 | Kovalsky et al. |
| 2012/0123511 A1 | 5/2012 | Brown |
| 2012/0123530 A1 | 5/2012 | Carpentier et al. |
| 2012/0130473 A1 | 5/2012 | Norris et al. |
| 2012/0130474 A1 | 5/2012 | Buckley |
| 2012/0130475 A1 | 5/2012 | Shaw |
| 2012/0136434 A1 | 5/2012 | Carpentier et al. |
| 2012/0150218 A1 | 6/2012 | Sandgren et al. |
| 2012/0165915 A1 | 6/2012 | Melsheimer et al. |
| 2012/0165930 A1 | 6/2012 | Gifford, III |
| 2012/0179244 A1 | 7/2012 | Schankereli et al. |
| 2012/0197292 A1 | 8/2012 | Chin-Chen et al. |
| 2012/0283824 A1 | 11/2012 | Lutter et al. |
| 2012/0290062 A1 | 11/2012 | McNamara et al. |
| 2012/0296360 A1 | 11/2012 | Norris et al. |
| 2012/0296418 A1 | 11/2012 | Bonyuet et al. |
| 2012/0300063 A1 | 11/2012 | Majkrzak et al. |
| 2012/0310328 A1 | 12/2012 | Olson et al. |
| 2012/0323316 A1 | 12/2012 | Chau et al. |
| 2012/0330408 A1 | 12/2012 | Hillukka et al. |
| 2013/0006347 A1 | 1/2013 | McHugo |
| 2013/0018450 A1 | 1/2013 | Hunt |
| 2013/0018458 A1 | 1/2013 | Yohanan et al. |
| 2013/0035759 A1 | 2/2013 | Gross et al. |
| 2013/0041204 A1 | 2/2013 | Heilman et al. |
| 2013/0041451 A1 | 2/2013 | Patterson et al. |
| 2013/0046373 A1 | 2/2013 | Cartledge et al. |
| 2013/0066342 A1 | 3/2013 | Dell |
| 2013/0079872 A1 | 3/2013 | Gallagher |
| 2013/0116780 A1 | 5/2013 | Miller et al. |
| 2013/0123896 A1 | 5/2013 | Bloss et al. |
| 2013/0123900 A1 | 5/2013 | Eblacas et al. |
| 2013/0150945 A1 | 6/2013 | Crawford et al. |
| 2013/0150956 A1 | 6/2013 | Yohanan et al. |
| 2013/0158647 A1 | 6/2013 | Norris et al. |
| 2013/0166017 A1 | 6/2013 | Cartledge et al. |
| 2013/0166022 A1 | 6/2013 | Conklin |
| 2013/0172978 A1 | 7/2013 | Vidlund et al. |
| 2013/0172992 A1 | 7/2013 | Gross et al. |
| 2013/0190861 A1 | 7/2013 | Chau et al. |
| 2013/0211501 A1 | 8/2013 | Buckley et al. |
| 2013/0245742 A1 | 9/2013 | Norris |
| 2013/0261737 A1 | 10/2013 | Costello |
| 2013/0261738 A1 | 10/2013 | Clague et al. |
| 2013/0274870 A1 | 10/2013 | Lombardi et al. |
| 2013/0282059 A1 | 10/2013 | Ketai et al. |
| 2013/0289711 A1* | 10/2013 | Liddy ................. A61F 2/06 623/1.24 |
| 2013/0289740 A1* | 10/2013 | Liddy ................. B05D 1/18 623/23.68 |
| 2013/0297013 A1 | 11/2013 | Klima et al. |
| 2013/0304197 A1 | 11/2013 | Buchbinder et al. |
| 2013/0304200 A1 | 11/2013 | McLean et al. |
| 2013/0310928 A1 | 11/2013 | Morriss et al. |
| 2013/0325114 A1 | 12/2013 | McLean et al. |
| 2013/0331929 A1 | 12/2013 | Mitra et al. |
| 2014/0000112 A1 | 1/2014 | Braid et al. |
| 2014/0005778 A1 | 1/2014 | Buchbinder et al. |
| 2014/0018911 A1 | 1/2014 | Zhou et al. |
| 2014/0018915 A1 | 1/2014 | Biadillah et al. |
| 2014/0031928 A1 | 1/2014 | Murphy et al. |
| 2014/0046430 A1 | 2/2014 | Shaw |
| 2014/0052237 A1 | 2/2014 | Lane et al. |
| 2014/0067050 A1 | 3/2014 | Costello et al. |
| 2014/0067054 A1 | 3/2014 | Chau et al. |
| 2014/0081376 A1 | 3/2014 | Burkart et al. |
| 2014/0106951 A1 | 4/2014 | Brandon |
| 2014/0120287 A1 | 5/2014 | Jacoby et al. |
| 2014/0121749 A1 | 5/2014 | Roeder |
| 2014/0121763 A1 | 5/2014 | Duffy et al. |
| 2014/0135894 A1 | 5/2014 | Norris et al. |
| 2014/0135895 A1 | 5/2014 | Andress et al. |
| 2014/0142681 A1 | 5/2014 | Norris |
| 2014/0142688 A1 | 5/2014 | Duffy et al. |
| 2014/0148891 A1 | 5/2014 | Johnson |
| 2014/0163690 A1 | 6/2014 | White |
| 2014/0172069 A1 | 6/2014 | Roeder et al. |
| 2014/0172077 A1 | 6/2014 | Bruchman et al. |
| 2014/0172082 A1 | 6/2014 | Bruchman et al. |
| 2014/0188210 A1 | 7/2014 | Beard et al. |
| 2014/0188221 A1 | 7/2014 | Chung et al. |
| 2014/0194981 A1 | 7/2014 | Menk et al. |
| 2014/0194983 A1 | 7/2014 | Kovalsky et al. |
| 2014/0207231 A1 | 7/2014 | Hacohen et al. |
| 2014/0214159 A1 | 7/2014 | Vidlund et al. |
| 2014/0222136 A1 | 8/2014 | Geist et al. |
| 2014/0222142 A1 | 8/2014 | Kovalsky et al. |
| 2014/0236287 A1 | 8/2014 | Clague et al. |
| 2014/0236289 A1 | 8/2014 | Alkhatib |

(56) References Cited

U.S. PATENT DOCUMENTS

| | | |
|---|---|---|
| 2014/0249622 A1 | 9/2014 | Carmi et al. |
| 2014/0257461 A1 | 9/2014 | Robinson et al. |
| 2014/0257467 A1 | 9/2014 | Lane et al. |
| 2014/0257475 A1 | 9/2014 | Gross et al. |
| 2014/0257476 A1 | 9/2014 | Montorfano et al. |
| 2014/0277358 A1 | 9/2014 | Slazas |
| 2014/0277409 A1 | 9/2014 | Börtlein et al. |
| 2014/0277411 A1 | 9/2014 | Börtlein et al. |
| 2014/0277418 A1 | 9/2014 | Miller |
| 2014/0277422 A1 | 9/2014 | Ratz et al. |
| 2014/0277427 A1 | 9/2014 | Ratz et al. |
| 2014/0296962 A1 | 10/2014 | Cartledge et al. |
| 2014/0296969 A1 | 10/2014 | Tegels et al. |
| 2014/0324164 A1 | 10/2014 | Gross et al. |
| 2014/0336744 A1 | 11/2014 | Tani et al. |
| 2014/0343670 A1 | 11/2014 | Bakis et al. |
| 2014/0358222 A1 | 12/2014 | Gorman, III et al. |
| 2014/0358224 A1 | 12/2014 | Tegels et al. |
| 2014/0379065 A1 | 12/2014 | Johnson et al. |
| 2014/0379074 A1 | 12/2014 | Spence et al. |
| 2014/0379076 A1 | 12/2014 | Vidlund et al. |
| 2015/0018944 A1 | 1/2015 | O'Connor et al. |
| 2015/0032205 A1* | 1/2015 | Matheny ............... A61F 2/2415 623/2.15 |
| 2015/0045880 A1 | 2/2015 | Hacohen |
| 2015/0045881 A1 | 2/2015 | Lim |
| 2015/0094802 A1 | 4/2015 | Buchbinder et al. |
| 2015/0119970 A1 | 4/2015 | Nakayama et al. |
| 2015/0127097 A1 | 5/2015 | Neumann et al. |
| 2015/0142100 A1 | 5/2015 | Morriss et al. |
| 2015/0142103 A1 | 5/2015 | Vidlund |
| 2015/0157457 A1 | 6/2015 | Hacohen |
| 2015/0157458 A1 | 6/2015 | Thambar et al. |
| 2015/0173896 A1 | 6/2015 | Richter et al. |
| 2015/0173897 A1 | 6/2015 | Raanani et al. |
| 2015/0196390 A1 | 7/2015 | Ma |
| 2015/0196393 A1 | 7/2015 | Vidlund et al. |
| 2015/0216661 A1 | 8/2015 | Hacohen et al. |
| 2015/0238313 A1 | 8/2015 | Spence et al. |
| 2015/0245934 A1 | 9/2015 | Lombardi et al. |
| 2015/0272730 A1 | 10/2015 | Melnick et al. |
| 2015/0272734 A1 | 10/2015 | Sheps et al. |
| 2015/0282964 A1 | 10/2015 | Beard et al. |
| 2015/0320556 A1 | 11/2015 | Levi et al. |
| 2015/0327994 A1 | 11/2015 | Morriss et al. |
| 2015/0328000 A1 | 11/2015 | Ratz et al. |
| 2015/0335429 A1 | 11/2015 | Morriss et al. |
| 2015/0342736 A1 | 12/2015 | Rabito et al. |
| 2015/0351903 A1 | 12/2015 | Morriss et al. |
| 2015/0351904 A1 | 12/2015 | Cooper et al. |
| 2015/0351906 A1 | 12/2015 | Hammer et al. |
| 2015/0359629 A1 | 12/2015 | Ganesan et al. |
| 2016/0030169 A1 | 2/2016 | Shahriari |
| 2016/0030171 A1 | 2/2016 | Quijano et al. |
| 2016/0089482 A1 | 3/2016 | Siegenthaler |
| 2016/0095700 A1 | 4/2016 | Righini |
| 2016/0100939 A1* | 4/2016 | Armstrong ............ A61F 2/2409 623/2.12 |
| 2016/0106539 A1 | 4/2016 | Buchbinder et al. |
| 2016/0113766 A1 | 4/2016 | Ganesan et al. |
| 2016/0113768 A1 | 4/2016 | Ganesan et al. |
| 2016/0125160 A1 | 5/2016 | Heneghan et al. |
| 2016/0175095 A1* | 6/2016 | Dienno ................ A61F 2/2415 623/2.17 |
| 2016/0213473 A1 | 7/2016 | Hacohen et al. |
| 2016/0220367 A1 | 8/2016 | Barrett |
| 2016/0228247 A1 | 8/2016 | Maimon et al. |
| 2016/0242902 A1 | 8/2016 | Morriss et al. |
| 2016/0270911 A1 | 9/2016 | Ganesan et al. |
| 2016/0296330 A1 | 10/2016 | Hacohen |
| 2016/0310268 A1 | 10/2016 | Oba et al. |
| 2016/0310274 A1 | 10/2016 | Gross et al. |
| 2016/0317301 A1 | 11/2016 | Quadri et al. |
| 2016/0317305 A1 | 11/2016 | Pelled et al. |
| 2016/0324633 A1 | 11/2016 | Gross et al. |
| 2016/0324635 A1 | 11/2016 | Vidlund et al. |
| 2016/0324640 A1 | 11/2016 | Gifford et al. |
| 2016/0331526 A1 | 11/2016 | Schweich et al. |
| 2016/0331527 A1 | 11/2016 | Vidlund et al. |
| 2016/0338706 A1 | 11/2016 | Rowe |
| 2016/0367360 A1 | 12/2016 | Cartledge et al. |
| 2016/0367368 A1 | 12/2016 | Vidlund et al. |
| 2016/0374801 A1 | 12/2016 | Jimenez et al. |
| 2016/0374802 A1 | 12/2016 | Levi et al. |
| 2017/0042678 A1 | 2/2017 | Ganesan et al. |
| 2017/0049435 A1 | 2/2017 | Sauer |
| 2017/0056166 A1 | 3/2017 | Ratz et al. |
| 2017/0056171 A1 | 3/2017 | Cooper et al. |
| 2017/0065407 A1 | 3/2017 | Hacohen et al. |
| 2017/0065411 A1* | 3/2017 | Grundeman .......... A61F 2/2418 |
| 2017/0128205 A1 | 5/2017 | Tamir et al. |
| 2017/0135816 A1 | 5/2017 | Lashinski et al. |
| 2017/0189174 A1 | 7/2017 | Braido et al. |
| 2017/0196688 A1 | 7/2017 | Christianson et al. |
| 2017/0196692 A1 | 7/2017 | Kirk et al. |
| 2017/0209264 A1 | 7/2017 | Chau et al. |
| 2017/0216026 A1 | 8/2017 | Quill et al. |
| 2017/0224323 A1 | 8/2017 | Rowe et al. |
| 2017/0231757 A1* | 8/2017 | Gassier ................ A61F 2/2409 623/2.17 |
| 2017/0231759 A1 | 8/2017 | Geist et al. |
| 2017/0231760 A1 | 8/2017 | Lane et al. |
| 2017/0231766 A1 | 8/2017 | Hariton et al. |
| 2017/0239048 A1 | 8/2017 | Goldfarb et al. |
| 2017/0252159 A1 | 9/2017 | Hacohen et al. |
| 2017/0266003 A1 | 9/2017 | Hammer et al. |
| 2017/0333183 A1* | 11/2017 | Backus ................. A61F 2/2415 |
| 2017/0333187 A1 | 11/2017 | Hariton et al. |
| 2017/0360426 A1 | 12/2017 | Hacohen et al. |
| 2017/0367823 A1 | 12/2017 | Hariton et al. |
| 2018/0000580 A1 | 1/2018 | Wallace et al. |
| 2018/0014930 A1 | 1/2018 | Hariton et al. |
| 2018/0014932 A1 | 1/2018 | Hammer et al. |
| 2018/0021129 A1 | 1/2018 | Peterson et al. |
| 2018/0028215 A1 | 2/2018 | Cohen |
| 2018/0049873 A1 | 2/2018 | Manash et al. |
| 2018/0055628 A1 | 3/2018 | Patel et al. |
| 2018/0055630 A1 | 3/2018 | Patel et al. |
| 2018/0098850 A1 | 4/2018 | Rafiee |
| 2018/0125644 A1 | 5/2018 | Conklin |
| 2018/0147059 A1 | 5/2018 | Hammer et al. |
| 2018/0153687 A1 | 6/2018 | Hariton |
| 2018/0153689 A1 | 6/2018 | Maimon et al. |
| 2018/0177594 A1 | 6/2018 | Patel et al. |
| 2018/0206983 A1 | 7/2018 | Noe et al. |
| 2018/0214263 A1* | 8/2018 | Rolando ............... A61F 2/2418 |
| 2018/0250126 A1 | 9/2018 | O'connor et al. |
| 2018/0250147 A1 | 9/2018 | Syed |
| 2018/0280136 A1 | 10/2018 | Hariton et al. |
| 2018/0296336 A1 | 10/2018 | Cooper et al. |
| 2018/0296341 A1 | 10/2018 | Noe et al. |
| 2018/0344457 A1 | 12/2018 | Gross et al. |
| 2018/0353294 A1 | 12/2018 | Calomeni et al. |
| 2018/0360457 A1 | 12/2018 | Ellis et al. |
| 2019/0038404 A1 | 2/2019 | Iamberger et al. |
| 2019/0038405 A1 | 2/2019 | Iamberger et al. |
| 2019/0053896 A1 | 2/2019 | Adamek-Bowers et al. |
| 2019/0060060 A1 | 2/2019 | Chau et al. |
| 2019/0060068 A1 | 2/2019 | Cope et al. |
| 2019/0060070 A1 | 2/2019 | Groothuis et al. |
| 2019/0069997 A1 | 3/2019 | Ratz et al. |
| 2019/0105153 A1 | 4/2019 | Barash et al. |
| 2019/0117391 A1 | 4/2019 | Humair |
| 2019/0167423 A1 | 6/2019 | Hariton et al. |
| 2019/0175339 A1 | 6/2019 | Vidlund |
| 2019/0183639 A1 | 6/2019 | Moore |
| 2019/0192295 A1 | 6/2019 | Spence |
| 2019/0216602 A1 | 7/2019 | Lozonschi |
| 2019/0336280 A1* | 11/2019 | Naor .................... A61F 2/2445 |
| 2019/0350701 A1 | 11/2019 | Adamek-Bowers et al. |
| 2019/0365530 A1 | 12/2019 | Hoang et al. |
| 2019/0388218 A1 | 12/2019 | Vidlund et al. |
| 2019/0388220 A1 | 12/2019 | Vidlund et al. |
| 2020/0000449 A1 | 1/2020 | Goldfarb et al. |

(56) References Cited

U.S. PATENT DOCUMENTS

| | | | |
|---|---|---|---|
| 2020/0000579 A1 | 1/2020 | Manash et al. |
| 2020/0015964 A1 | 1/2020 | Noe et al. |
| 2020/0030098 A1 | 1/2020 | Delgado et al. |
| 2020/0038181 A1 | 2/2020 | Hariton |
| 2020/0054335 A1 | 2/2020 | Hernandez et al. |
| 2020/0060818 A1 | 2/2020 | Geist et al. |
| 2020/0113677 A1 | 4/2020 | McCann et al. |
| 2020/0113689 A1 | 4/2020 | McCann et al. |
| 2020/0113692 A1 | 4/2020 | McCann et al. |
| 2020/0138567 A1 | 5/2020 | Marr et al. |
| 2020/0163761 A1* | 5/2020 | Hariton ................ A61F 2/243 |
| 2020/0214832 A1 | 7/2020 | Metchik et al. |
| 2020/0237512 A1 | 7/2020 | McCann et al. |
| 2020/0246136 A1 | 8/2020 | Marr et al. |
| 2020/0246140 A1* | 8/2020 | Hariton ............... A61F 2/2418 |
| 2020/0253600 A1 | 8/2020 | Darabian |
| 2020/0261094 A1 | 8/2020 | Goldfarb et al. |
| 2020/0315786 A1 | 10/2020 | Metchik et al. |
| 2020/0337842 A1 | 10/2020 | Metchik et al. |
| 2021/0093449 A1* | 4/2021 | Hariton ................. A61F 2/24 |
| 2021/0113331 A1 | 4/2021 | Quadri |

FOREIGN PATENT DOCUMENTS

| | | |
|---|---|---|
| CN | 103997990 | 8/2014 |
| EP | 0170262 | 2/1986 |
| EP | 1264582 | 12/2002 |
| EP | 1768630 | 1/2015 |
| JP | 53152790 | 12/1978 |
| WO | 1998/043557 | 10/1998 |
| WO | 1999/030647 | 6/1999 |
| WO | 2000-047139 | 8/2000 |
| WO | 20010046894 | 6/2001 |
| WO | 2001-062189 | 8/2001 |
| WO | 01/82832 | 11/2001 |
| WO | 2003/020179 | 3/2003 |
| WO | 2003/028558 | 4/2003 |
| WO | 2004/108191 | 12/2004 |
| WO | 2005/107650 | 11/2005 |
| WO | 2006/007401 | 1/2006 |
| WO | 06/054930 | 5/2006 |
| WO | 2006/070372 | 7/2006 |
| WO | 2006/086434 | 8/2006 |
| WO | 2006/089236 | 8/2006 |
| WO | 2006/116558 | 11/2006 |
| WO | 2007/059252 | 5/2007 |
| WO | 08/013915 | 1/2008 |
| WO | 2008/029296 | 3/2008 |
| WO | 2008/070797 | 6/2008 |
| WO | 2008/103722 | 8/2008 |
| WO | 09/033469 | 3/2009 |
| WO | 09/053497 | 4/2009 |
| WO | 2009/091509 | 7/2009 |
| WO | 2010/006627 | 1/2010 |
| WO | 2010/037141 | 4/2010 |
| WO | 2010/045297 | 4/2010 |
| WO | 2010/057262 | 5/2010 |
| WO | 2010/073246 | 7/2010 |
| WO | 2010/081033 | 7/2010 |
| WO | 2010/121076 | 10/2010 |
| WO | 2011/025972 | 3/2011 |
| WO | 2011/069048 | 6/2011 |
| WO | 2011/089601 | 7/2011 |
| WO | 2011/106137 | 9/2011 |
| WO | 2011/111047 | 9/2011 |
| WO | 01/87190 | 11/2011 |
| WO | 2011/137531 | 11/2011 |
| WO | 2011-143263 | 11/2011 |
| WO | 2011/154942 | 12/2011 |
| WO | 2012/011108 | 1/2012 |
| WO | 2012/024428 | 2/2012 |
| WO | 2012/036740 | 3/2012 |
| WO | 2012/048035 | 4/2012 |
| WO | 2012/127309 | 9/2012 |
| WO | 2012/177942 | 12/2012 |
| WO | 2013/021374 | 2/2013 |
| WO | 2013/021375 | 2/2013 |
| WO | 2013/021384 | 2/2013 |
| WO | 2013/059747 | 4/2013 |
| WO | 2013/072496 | 5/2013 |
| WO | 2013/078497 | 6/2013 |
| WO | 2013114214 | 8/2013 |
| WO | 2013/128436 | 9/2013 |
| WO | 2013/175468 | 11/2013 |
| WO | 2014/022124 | 2/2014 |
| WO | 2014/076696 | 5/2014 |
| WO | 2014/115149 | 7/2014 |
| WO | 2014/145338 | 9/2014 |
| WO | 2014/164364 | 10/2014 |
| WO | 2014/194178 | 12/2014 |
| WO | 2015/173794 | 11/2015 |
| WO | 2016/016899 | 2/2016 |
| WO | 2016/093877 | 6/2016 |
| WO | 2016/125160 | 8/2016 |
| WO | 2017/223486 | 12/2017 |
| WO | 2018/025260 | 2/2018 |
| WO | 2018/025263 | 2/2018 |
| WO | 2018/029680 | 2/2018 |
| WO | 2018/039631 | 3/2018 |
| WO | 2018/106837 | 6/2018 |
| WO | 2018/112429 | 6/2018 |
| WO | 2018/118717 | 6/2018 |
| WO | 2018/131042 | 7/2018 |
| WO | 2018/131043 | 7/2018 |
| WO | 2739214 | 10/2018 |
| WO | 2019/026059 | 2/2019 |
| WO | 2019/030753 | 2/2019 |
| WO | 2019027507 | 2/2019 |
| WO | 2019/077595 | 4/2019 |
| WO | 2019/116369 | 6/2019 |
| WO | 2019/138400 | 7/2019 |
| WO | 2019/195860 | 10/2019 |
| WO | 2019/202579 | 10/2019 |
| WO | 2020/058972 | 3/2020 |
| WO | 2020/167677 | 8/2020 |

OTHER PUBLICATIONS

Sündermann, Simon H., et al. "Feasibility of the Engager™ aortic transcatheter valve system using a flexible over-the-wire design." European Journal of Cardio-Thoracic Surgery 42.4 (2012): e48-e52.

An Office Action summarized English translation and Search Report dated Jul. 3, 2020, which issued during the prosecution of Chinese Patent Application No. 201780061210.3.

Serruys, P. W., Piazza, N., Cribier, A., Webb, J., Laborde, J. C., & de Jaegere, P. (Eds). (2009). Transcatheter aortic valve implantation: tips and tricks to avoid failure. CRC Press.—Screenshots from Google Books downloaded from: https://books.google.co.il/books?id=FLzLBQAAQBAJ&lpg=PA198&ots=soqWrDH-y_&dq=%20%22Edwards%20SAPIEN%22&lr&pg=PA20#v=onepage&q=%22Edwards%20SAPIEN%22&f=false ; Downloaded on Jun. 18, 2020.

An International Search Report and a Written Opinion both dated Jun. 24, 2020, which issued during the Prosecution of Applicant's PCT/IL2019/051398.

An Office Action dated Jul. 14, 2020, which issued during the prosecution of U.S. Appl. No. 16/324,339.

Notice of Allowance dated Aug. 28, 2020, which issued during the prosecution of U.S. Appl. No. 16/324,339.

Notice of Allowance dated Jul. 29, 2020, which issued during the prosecution of U.S. Appl. No. 16/132,937.

An Office Action dated Jul. 29, 2020, which issued during the prosecution of U.S. Appl. No. 16/269,328.

Notice of Allowance dated Aug. 26, 2020, which issued during the prosecution of U.S. Appl. No. 16/269,328.

An Office Action dated Aug. 7, 2020, which issued during the prosecution of U.S. Appl. No. 15/668,659.

Tchetche, D. and Nicolas M. Van Mieghem: "New-generation TAVI devices: description and specifications" EuroIntervention, 2014, No. 10:U90-U100.

(56) References Cited

OTHER PUBLICATIONS

Symetis S.A.: "Acurate neo™ Aortic Bioprosthesis for Implantation using the Acurate neo™ TA Transapical Delivery System in Patients with Severe Aortic Stenosis," Clinical Investigation Plan, Protocol No. 2015-01, Vs. No. 2, 2015:1-76.
Notice of Allowance dated Sep. 10, 2020, which issued during the prosecution on U.S. Appl. No. 15/600,190.
An International Preliminary Report on Patentability dated Oct. 20, 2020, which issued during the prosecution of Applicant's PCT/IL2019/050142.
An Office Action dated Oct. 5, 2020, which issued during the prosecution of Canadian Patent Application No. 2,973,940.
Notice of Allowance dated Nov. 19, 2020, which issued during the prosecution of U.S. Appl. No. 16/318,025.
An Office Action dated Sep. 24, 2020, which issued during the prosecution of U.S. Appl. No. 16/811,732.
An Office Action summarized English translation and Search Report dated Nov. 25, 2020, which issued during the prosecution of Chinese Patent Application No. 201910449820.1.
An Office Action dated Nov. 30, 2020, which issued during the prosecution of U.S. Appl. No. 16/138,129.
An Office Action dated Nov. 23, 2012, which issued during the prosecution of U.S. Appl. No. 13/033,852.
An Office Action dated Dec. 31, 2012, which issued during the prosecution of U.S. Appl. No. 13/044,694.
An Office Action dated Feb. 6, 2013, which issued during the prosecution of U.S. Appl. No. 13/412,814.
Langer F et al., "Ring plus String: Papillary muscle repositioning as an adjunctive repair technique for ischemic mitral regurgitation," J Thorac Cardiovasc Surg 133:247-9, Jan. 2007.
Langer F et al., "Ring=String: Successful repair technique for ischemic mitral regurgitation with severe leaflet tethering," Circulation 120[suppl 1]: S85-S91, Sep. 2009.
"Transcatheter Valve-in-Valve Implantation for Failed Bioprosthetic Heart Valves", J Webb et al., Circulation. Apr. 2010; 121: 1848-1857.
Jansen, J., Willeke, S., Reul, H. and Rum, G. (1992), Detachable Shape-Memory Sewing Ring for Heart Valves. Artificial Organs, 16:294-297. 1992 (an abstract).
Alexander S. Geha, et al., Replacement of degenerated mitral and aortic bioprostheses without explanation Ann Thorac Surg. Jun. 2001; 72:1509-1514.
An International Search Report and a Written Opinion both dated Oct. 13, 2011 which issued during the prosecution of Applicant's PCT/IL11/00231.
An Office Action dated Jul. 1, 2016, which issued during the prosecution of U.S. Appl. No. 14/161,921.
An International Search Report and a Written Opinion both dated Dec. 5, 2011, which issued during the prosecution of Applicant's PCT/IL11/00582.
An Office Action dated May 29, 2012, which issued during the prosecution of U.S. Appl. No. 12/840,463.
U.S. Appl. No. 61/555,160, filed Nov. 3, 2011.
U.S. Appl. No. 61/525,281, filed Aug. 19, 2011.
U.S. Appl. No. 61/537,276, filed Sep. 21, 2011.
U.S. Appl. No. 61/515,372, filed Aug. 5, 2011.
U.S. Appl. No. 61/492,449, filed Jun. 2, 2011.
U.S. Appl. No. 61/588,892, filed Jan. 20, 2012.
An International Search Report and a Written Opinion both dated Feb. 6, 2013, which issued during the prosecution of Applicant's PCT/IL12/00292.
An International Search Report and a Written Opinion both dated Feb. 6, 2013, which issued during the prosecution of Applicant's PCT/IL12/00293.
An Office Action dated Nov. 28, 2012, which issued during the prosecution of U.S. Appl. No. 12/961,721.
An Office Action dated Feb. 15, 2013, which issued during the prosecution of U.S. Appl. No. 12/840,463.
An Office Action dated Feb. 10, 2014, which issued during the prosecution of U.S. Appl. No. 13/033,852.
An Office Action dated Sep. 19, 2014, which issued during the prosecution of U.S. Appl. No. 13/044,694.
An International Search Report and a Written Opinion both dated Sep. 4, 2014 which issued during the prosecution of Applicant's PCT/IL2014/050087.
Invitation to Pay Additional Fees dated Jun. 12, 2014 PCT/IL2014/050087.
An Office Action dated Jun. 17, 2014, which issued during the prosecution of U.S. Appl. No. 12/961,721.
An Office Action dated Jul. 3, 2014, which issued during the prosecution of U.S. Appl. No. 13/033,852.
An Office Action dated May 23, 2014, which issued during the prosecution of U.S. Appl. No. 13/412,814.
Dominique Himbert; Mitral Regurgitation and Stenosis from Bioprosthesis and Annuloplasty Failure: Transcatheter approaches and outcomes, 24 pages Oct. 28, 2013.
An International Search Report and a Written Opinion both dated Mar. 17, 2014 which issued during the prosecution of Applicant's PCT/IL2013/050937.
An International Preliminary Report on patentabilty dated Dec. 2, 2013, which issued during the prosecution of Applicant's PCT/IL11/00582.
An Office Action dated Sep. 12, 2013, which issued during the prosecution of U.S. Appl. No. 13/412,814.
An Office Action dated Aug. 2, 2013, which issued during the prosecution of U.S. Appl. No. 13/033,852.
An International Preliminary Report on patentabilty dated Sep. 11, 2012, which issued during the prosecution of Applicant's PCT/IL2011/000231.
An Office Action dated Jul. 2, 2014, which issued during the prosecution of U.S. Appl. No. 13/811,308.
An Office Action dated Jan. 20, 2016, which issued during the prosecution of U.S. Appl. No. 14/161,921.
An Office Action dated Jul. 23, 2013, which issued during the prosecution of U.S. Appl. No. 12/961,721.
An Office Action dated Jul. 18, 2013, which issued during the prosecution of U.S. Appl. No. 13/044,694.
An Office Action dated Nov. 8, 2013, which issued during the prosecution of U.S. Appl. No. 12/840,463.
An Office Action dated Jun. 4 2014, which issued during the prosecution of U.S. Appl. No. 12/840,463.
An Office Action dated Aug. 13, 2012, which issued during the prosecution of U.S. Appl. No. 13/044,694.
An Office Action dated Jul. 2, 2012 which issued during the prosecution of U.S. Appl. No. 13/033,852.
An Office Action dated Feb. 3, 2014, which issued during the prosecution of U.S. Appl. No. 13/811,308.
An International Preliminary Report on patentabilty dated Feb. 11, 2014, which issued during the prosecution of Applicant's PCT/IL12/00292.
An International Preliminary Report on patentabilty dated Feb. 11, 2014, which issued during the prosecution of Applicant's PCT/IL12/00293.
A Notice of Allowance dated Aug. 15, 2014, which issued during the prosecution of U.S. Appl. No. 13/412,814.
An Office Action dated Aug. 14, 2012, which issued during the prosecution of U.S. Appl. No. 12/961,721.
U.S. Appl. No. 61/283,819, filed Dec. 8, 2009.
Notice of Allowance dated U.S. Appl. No. Apr. 8, 2016, which issued during the prosecution of U.S. Appl. No. 14/237,258.
U.S. Appl. No. 61/756,034, filed Jan. 24, 2013.
U.S. Appl. No. 61/756,049, filed Jan. 24, 2013.
An International Preliminary Report on Patentability dated Jan. 31, 2017, which issued during the prosecution of Applicant's PCT/IL2015/050792.
U.S. Appl. No. 62/372,861, filed Aug. 10, 2016.
Notice of Allowance dated Aug. 13, 2018, which issued during the prosecution of U.S. Appl. No. 15/995,597.
Notice of Allowance dated Apr. 20, 2018, which issued during the prosecution of U.S. Appl. No. 15/878,206.
An Office Action dated Dec. 10, 2015, which issued during the prosecution of U.S. Appl. No. 14/237,258.

(56) References Cited

OTHER PUBLICATIONS

An International Preliminary Report on Patentability dated Jul. 28, 2015, which issued during the prosecution of Applicant's PCT/IL2014/050087.
An Office Action dated Nov. 27, 2015, which issued during the prosecution of U.S. Appl. No. 14/626,267.
An Office Action dated Jan. 21, 2016, which issued during the prosecution of U.S. Appl. No. 14/237,264.
An Office Action dated Jan. 30, 2015, which issued during the prosecution of UK Patent Application No. 1413474.6.
An International Search Report and a Written Opinion both dated May 30, 2016, which issued during the prosecution of Applicant's PCT/IL2016/050125.
An Office Action dated Sep. 26, 2016, which issued during the prosecution of U.S. Appl. No. 14/763,004.
An Office Action dated Jan. 18, 2017, which issued during the prosecution of U.S. Appl. No. 14/626,267.
An Office Action dated Feb. 7, 2017, which issued during the prosecution of U.S. Appl. No. 14/689,608.
An Office Action dated Feb. 8, 2017, which issued during the prosecution of UK Patent Application No. 1613219.3.
An Office Action together dated Feb. 10, 2017, which issued during the prosecution of European Patent Application No. 12821522.5.
An International Search Report and a Written Opinion both dated Oct. 27, 2015, which issued during the prosecution of Applicant's PCT/IL2015/050792.
European Search Report dated Feb. 18, 2015, which issued during the prosecution of Applicant's European App No. 12821522.5.
Saturn Project—a novel solution for transcatheter heart valve replacement specifically designed to address clinical therapeutic needs on mitral valve: Dec. 2016.
Righini presentation EuroPCR May 2015 (Saturn)—(downloaded from: https://www.pcronline.com/Cases-resourcesimages/Resources/Course-videos-slides/2015/Cardiovascularinnovation-pipeline-Mitral-and-tricuspid-valve-interventions).
An Advisory Action dated Apr. 2, 2018, which issued during the prosecution of U.S. Appl. No. 14/763,004.
An Office Action dated Jul. 26, 2018, which issued during the prosecution of U.S. Appl. No. 15/872,501.
An Office Action dated May 4, 2018, which issued during the prosecution of U.S. Appl. No. 15/872,501.
An Office Action dated Apr. 20, 2018, which issued during the prosecution of U.S. Appl. No. 15/886,517.
An Office Action dated Aug. 9, 2018, which issued during the prosecution of U.S. Appl. No. 15/899,858.
An Office Action dated Aug. 9, 2018, which issued during the prosecution of U.S. Appl. No. 15/902,403.
An Office Action dated Jun. 28, 2018, which issued during the prosecution of U.S. Appl. No. 29/635,658.
An Office Action dated Jun. 28, 2018, which issued during the prosecution of U.S. Appl. No. 29/635,661.
Georg Lutter, MD, et al; "Percutaneous Valve Replacement: Current State and Future Prospects", The Annals of Thoracic Surgery ; vol. 78, pp. 2199-2206; Dec. 2004.
An Office Action dated Jun. 6, 2018, which issued during the prosecution of UK Patent Application No. 1720803.4.
An International Search Report and a Written Opinion both dated Jun. 20, 2018, which issued during the prosecution of Applicant's PCT/IL2018/050024.
An Office Action dated Jun. 18, 2018, which issued during the prosecution of UK Patent Application No. 1800399.6.
An Office Action dated Oct. 23, 2017, which issued during the prosecution of U.S. Appl. No. 14/763,004.
An Office Action dated Dec. 7, 2017, which issued during the prosecution of U.S. Appl. No. 15/213,791.
Interview Summary dated Feb. 8, 2018, which issued during the prosecution of U.S. Appl. No. 15/213,791.
An Office Action dated Feb. 7, 2018, which issued during the prosecution of U.S. Appl. No. 15/197,069.
An International Search Report and a Written Opinion both dated Nov. 24, 2017, which issued during the prosecution of Applicant's PCT/IL2017/050873.
An Office Action dated Jan. 5, 2018, which issued during the prosecution of U.S. Appl. No. 15/541,783.
An Office Action dated Feb. 2, 2018, which issued during the prosecution of U.S. Appl. No. 15/329,920.
An Invitation to pay additional fees dated Jan. 2, 2018, which issued during the prosecution of Applicant's PCT/IL2017/050849.
An Invitation to pay additional fees dated Sep. 29, 2017, which issued during the prosecution of Applicant's PCT/IL2017/050873.
European Search Report dated Jun. 29, 2017, which issued during the prosecution of Applicant's European App No. 11809374.9.
An Invitation to pay additional fees dated Oct. 11, 2018, which issued during the prosecution of Applicant's PCT/IL2018/050725.
An Office Action dated Dec. 4, 2018, which issued during the prosecution of U.S. Appl. No. 16/045,059.
An Office Action together with the English translation dated Nov. 5, 2018 which issued during the prosecution of Chinese Patent Application No. 201680008328.5.
Notice of Allowance dated Sep. 25, 2018, which issued during the prosecution of U.S. Appl. No. 15/188,2507.
European Search Report dated Sep. 26, 2018 which issued during the prosecution of Agglicant's European App No. 181867841.7.
An Office Action dated Jun. 30, 2015, which issued during the prosecution of U.S. Appl. No. 14/522,987.
Notice of Allowance dated Dec. 13, 2013, which issued during the U.S. Appl. No. 13/675,119.
An International Preliminary Report on Patentability dated Aug. 8, 2017, which issued during the prosecution of Applicant's PCT/IL2016/050125.
An Office Action dated Jan. 17, 2018, which issued during the prosecution of U.S. Appl. No. 14/763,004.
An Office Action dated Mar. 25, 2015, which issued during the prosecution of U.S. Appl. No. 12/840,463.
An Office Action dated Feb. 25, 2016, which issued during the prosecution of U.S. Appl. No. 14/522,987.
An Office Action dated Apr. 13, 2016, which issued during the prosecution of U.S. Appl. No. 14/626,267.
An Office Action dated Aug. 28, 2015, which issued during the prosecution of U.S. Appl. No. 14/237,264.
Maisano (2015) TCR presentation re Cardiovalve.
Notice of Allowance dated Sep. 29, 2016, which issued during the prosecution of U.S. Appl. No. 14/442,541.
Notice of Allowance dated May 10, 2016, which issued during the prosecution of U.S. Appl. No. 14/237,258.
Notice of Allowance dated May 20, 2016, which issued during the prosecution of U.S. Appl. No. 14/237,958.
An International Preliminary Report on Patentability dated May 19, 2015, which issued during the prosecution of Applicant's PCT/IL2013/050937.
Dusan Pavcnik, MD, PhD2, et al; "Development and Initial Experimental Evaluation of a Prosthetic Aortic Valve for Transcatheter Placement", Cardiovascular Radiology. Radiology Apr. 1992, vol. 183, pp. 151-154.
Notice of Allowance dated Oct. 16, 2013, which issued during the prosecution of U.S. Appl. No. 13/675,119.
Notice of Allowance dated Feb. 11, 2015, which issued during the prosecution of U.S. Appl. No. 13/033,852.
Notice of Allowance dated May 5, 2015, which issued during the prosecution of U.S. Appl. No. 12/840,463.
Notice of Allowance dated Mar. 10, 2015, which issued during the prosecution of U.S. Appl. No. 13/811,308.
Notice of Allowance dated Jul. 1, 2016, which issued during the prosecution of U.S. Appl. No. 14/442,541.
An Office Action dated Mar. 25, 2019, which issued during the prosecution of European Patent Application No. 14710060.6.
An International Search Report and a Written Opinion both dated Nov. 9, 2018, which issued during the prosecution of Applicant's PCT/IL2018/050869.
An International Search Report and a Written Opinion both dated Dec. 5, 2018, which issued during the prosecution of Applicant's PCT/IL2018/050725.

(56) References Cited

OTHER PUBLICATIONS

An International Search Report and a Written Opinion both dated Apr. 25, 2019, which issued during the prosecution of Applicant's PCT/IL2019/050142.
An International Preliminary Report on Patentability dated Feb. 12, 2019, which issued during the prosecution of Applicant's PCT/IL2017/050873.
An Office Action dated Sep. 13, 2019, which issued during the prosecution of U.S. Appl. No. 16/460,313.
An Office Action dated Nov. 26, 2019, which issued during the prosecution of U.S. Appl. No. 16/532,945.
An Office Action dated Aug. 16, 2019, which issued during the prosecution of U.S. Appl. No. 15/668,659.
An Office Action dated Nov. 1, 2019, which issued during the prosecution of U.S. Appl. No. 15/872,501.
An Office Action dated Jun. 14, 2019, which issued during the prosecution of U.S. Appl. No. 15/703,385.
An Office Action dated Oct. 4, 2019, which issued during the prosecution of U.S. Appl. No. 16/183,140.
An Office Action dated Jun. 13, 2019, which issued during the prosecution of U.S. Appl. No. 16/388,038.
An International Preliminary Report on Patentability dated Feb. 4, 2020, which issued during the prosecution of Applicant's PCT/IL2018/050725.
An International Search Report and a Written Opinion both dated Jan. 25, 2019, which issued during the prosecution of Applicant's PCT/IL2018/051122.
An International Search Report and a Written Opinion both dated May 13, 2019, which issued during the prosecution of Applicant's PCT/IL2018/051350.
An International Preliminary Report on Patentability dated Feb. 5, 2019, which issued during the prosecution of Applicant's PCT/IL2017/050849.
An Office Action dated Oct. 25, 2018, which issued during the prosecution of U.S. Appl. No. 14/763,004.
An Office Action dated Mar. 4, 2019, which issued during the prosecution of U.S. Appl. No. 14/763,004.
An Office Action dated Jan. 9, 2019, which issued during the prosecution of U.S. Appl. No. 15/329,920.
An Office Action dated Jan. 30, 2019, which issued during the prosecution of U.S. Appl. No. 15/872,501.
An Office Action dated Feb. 5, 2019, which issued during the prosecution of U.S. Appl. No. 15/899,858.
An Office Action dated May 23, 2019, which issued during the prosecution of U.S. Appl. No. 15/668,659.
An Office Action dated May 1, 2019, which issued during the prosecution of U.S. Appl. No. 15/691,032.
An Office Action dated Aug. 1, 2019, which issued during the prosecution of U.S. Appl. No. 15/668,559.
An Office Action dated Jun. 19, 2019, which issued during the prosecution of U.S. Appl. No. 15/682,789.
Notice of Allowance dated Jan. 13, 2020, which issued during the prosecution of U.S. Appl. No. 15/956,956.
An Office Action dated Jun. 25, 2019, which issued during the prosecution of U.S. Appl. No. 15/329,920.
An Office Action dated May 16, 2019, which issued during the prosecution of U.S. Appl. No. 15/433,547.
U.S. Appl. No. 62/560,384, filed Sep. 19, 2017.
U.S. Appl. No. 62/112,343, filed Feb. 5, 2015.
An Office Action dated Jan. 6, 2020, which issued during the prosecution of U.S. Appl. No. 16/660,231.
An Office Action dated Dec. 31, 2019, which issued during the prosecution of U.S. Appl. No. 16/183,140.
An Office Action dated Jan. 14, 2020, which issued during the prosecution of U.S. Appl. No. 16/284,331.
European Search Report dated Mar. 5, 2020 which issued during the prosecution of Applicant's European App No. 17752184.6.
European Search Report dated Mar. 4, 2020 which issued during the prosecution of Applicant's European App No. 16706913.7.

Notice of Allowance dated Mar. 12, 2020, which issued during the prosecution of U.S. Appl. No. 16/460,313.
An Office Action dated Jan. 9, 2020, which issued during the prosecution of U.S. Appl. No. 15/600,190.
An Office Action dated Jan. 3, 2020, which issued during the prosecution of U.S. Appl. No. 16/678,355.
An Office Action dated Feb. 6, 2020, which issued during the prosecution of U.S. Appl. No. 15/668,659.
An Office Action dated Dec. 24, 2020, which issued during the prosecution of U.S. Appl. No. 16/144,054.
An Office Action dated Feb. 2, 2021, which issued during the prosecution of U.S. Appl. No. 16/811,732.
An Office Action dated Jan. 13, 2021, which issued during the prosecution of European Patent Application No. 15751089.2.
Maisano, F., et al. "The edge-to-edge technique: a simplified method to correct mitral insufficiency." European journal of cardio-thoracic surgery 13.3 (1998): 240-246.
Declaration of Dr. Ivan Vesely, Ph.D. in Support of Petition for Inter Partes Review of U.S. Pat. No. 10,226,341—dated Dec. 17, 2020.
Petition for Inter Partes Review of U.S. Pat. No. 10,226,341 and Exhibits 1001-1013—dated Dec. 29, 2020.
An Office Action together with an English summary dated March 3, 2021, which issued during the prosecution of Chinese Patent Application No. 201780047391.4.
Fucci, C., et al. "Improved results with mitral valve repair using new surgical techniques." European journal of cardio-thoracic surgery 9.11 (1995): 621-627.
Declaration of Wan Vesely, Ph.D., in Support of Petition for Inter Partesreview of U.S. Pat. No. 7,563,267—dated May 29, 2019.
U.S. Appl. No. 60/128,690, filed Apr. 9, 1999.
Batista, Randas JV, et al. "Partial left ventriculectomy to treat end-stage heart disease." The Annals of thoracic surgery 64.3 (1997): 634-638.
Beall Jr, Arthur C., et al. "Clinical experience with a dacron velour-covered teflon-disc mitral-valve prosthesis." The Annals of thoracic surgery 5.5 (1968): 402-410.
Mitral Valve Academic Research Consortium. "Clinical Trial Design Principles and Endpoint Definitions for Transcatheter Mitral Valve Repair and Replacement: Part 1: Clinical Trial Design Principles a Consensus Document from the Mitral Valve Academic Research Consortium." Journal of the American College of Cardiology 66.3 (2015): 278-307.
Kalbacher, D., et al. "1000 MitraClip™ procedures: Lessons learnt from the largest single-centre experience worldwide." (2019): 3137-3139.
U.S. Appl. No. 60/613,867, filed Sep. 27, 2004.
European Search Report dated Jun. 10, 2021 which issued during the prosecution of Applicant's European App No. 21157988.3.
An Invitation to pay additional fees dated May 19, 2021, which issued during the prosecution of Applicant's PCT/IL2021/050132.
An International Search Report and a Written Opinion both dated Jul. 12, 2021, which issued during the prosecution of Applicant's PCT/IL2021/050132.
IPR2021-00383 Petitioners' Authorized Reply to Patent Owner's Preliminary Response dated May 27, 2021.
Exhibit 1014—Transcript of proceedings held May 20, 2021 (*Edwards Lifesciences* vs. *Cardiovalve*).
Exhibit 1015—Facilitate, Meriam-Webster.com, https://www.merriamwebster.com/dictionary/facilitate (visited May 26, 2021).
Patent Owner's Authorized Surreply to Petitioner's Reply to Patent Owner's Preliminary Response dated Jun. 4, 2021 (Edwards *Lifesciences* vs. *Cardiovalve*).
An Office Action dated Aug. 18, 2021, which issued during the prosecution of U.S. Appl. No. 17/210,183.
Institution decision dated Jul. 20, 2021 (*Edwards Lifesciences* vs. *Cardiovalve*).
Poirier, Nancy C., et al. "A novel repair for patients with atrioventricular septal defect requiring reoperation for left atrioventricular valve regurgitation." European journal of cardio-thoracic surgery 18.1 (2000): 54-61.
An Office Action dated Mar. 29, 2021, which issued during the prosecution of U.S. Appl. No. 16/738,516.

(56) References Cited

OTHER PUBLICATIONS

Ando, Tomo, et al. "Iatrogenic ventricular septal defect following transcatheter aortic valve replacement: a systematic review." Heart, Lung and Circulation 25.10 (2016): 968-974.

Urena, Marina, et al. "Transseptal transcatheter mitral valve replacement using balloon-expandable transcatheter heart valves: a step-by-step approach." JACC: Cardiovascular Interventions 10.19 (2017): 1905-1919.

An English summary of an Official Action dated Mar. 29, 2021, which issued during the prosecution of Chinese Patent Application No. 201780061210.3.

Petition for Inter Partes Review of U.S. Pat. No. 10,702,385—dated Jun. 4, 2021.

Declaration of Ivan Vesely, Ph.D. In Support of Petition for Inter Partes Review of U.S. Pat. No. 10,702,385—dated Jun. 4, 2021.

Notice of Allowance dated Jun. 4, 2021, which issued during the prosecution of U.S. Appl. No. 16/802,353.

An Office Action dated May 12, 2021, which issued during the prosecution of Canadian Patent Application No. 2,973,940.

Notice of Allowance dated May 17, 2021, which issued during the prosecution of US Patent Application No. 16/138,129.

An International Search Report and a Written Opinion both dated Jan. 28, 2020, which issued during the prosecution of Applicant's PCT/IL2019/051031.

An International Preliminary Report on Patentability dated Mar. 9, 2021, which issued during the prosecution of Applicant's PCT/IL2019/051031.

\* cited by examiner

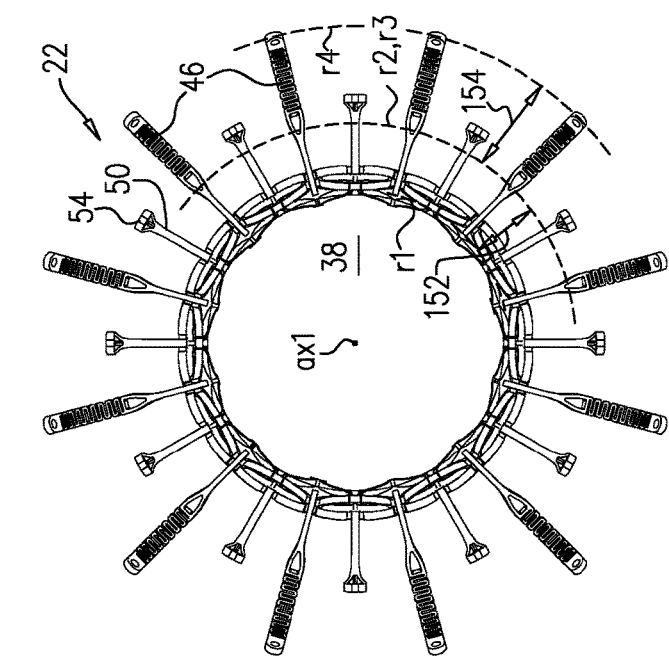
FIG. 1D
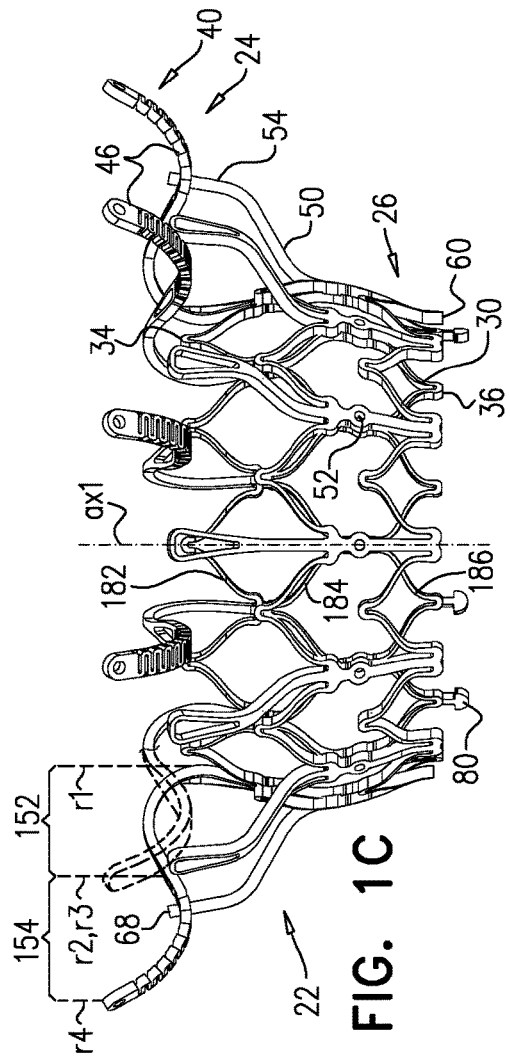
FIG. 1C
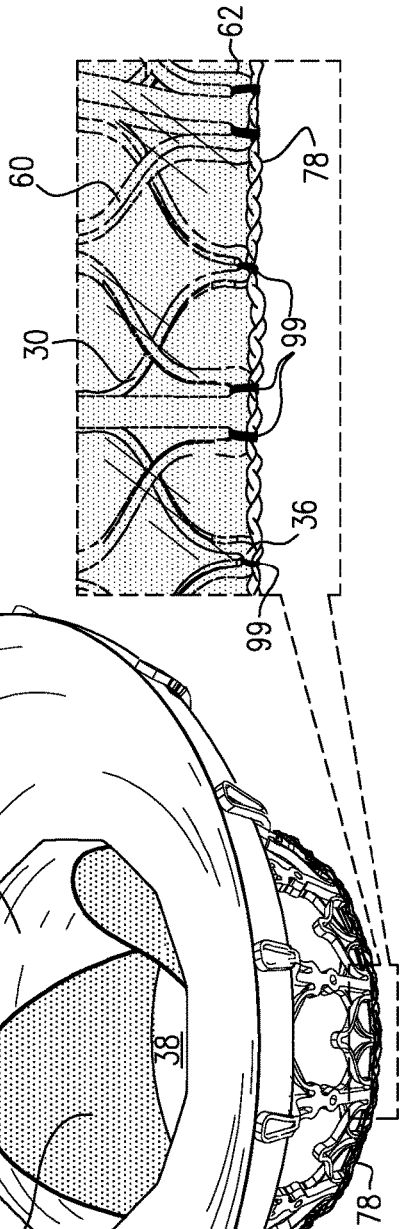
FIG. 1E
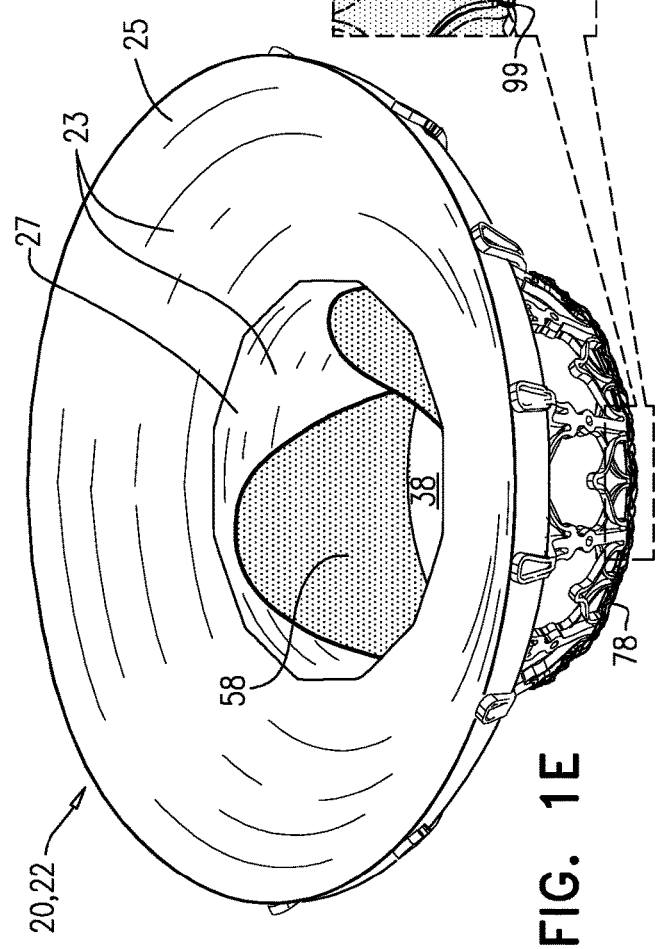

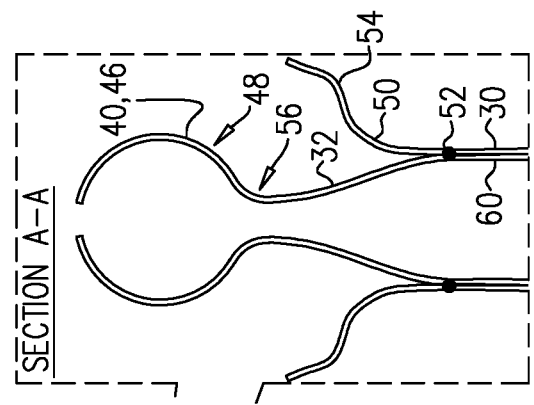
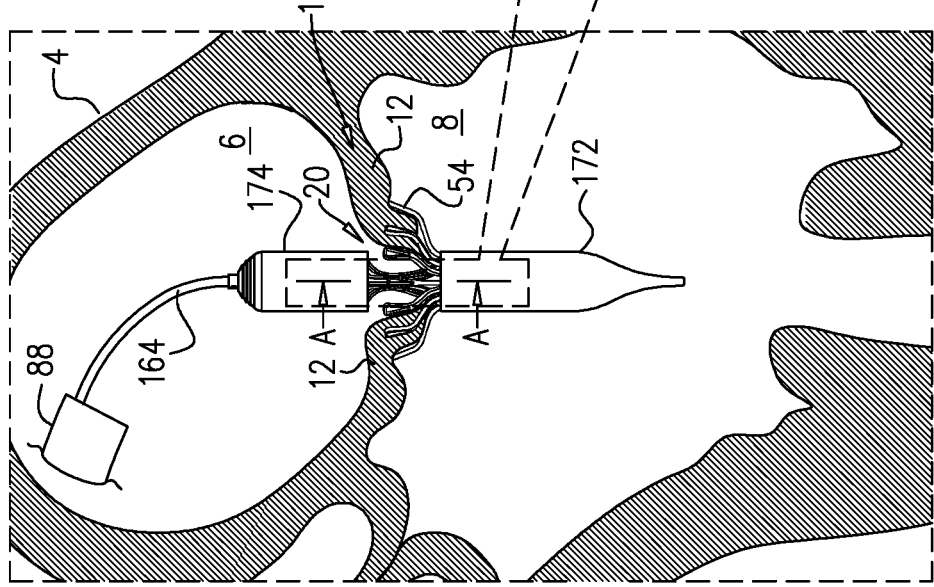
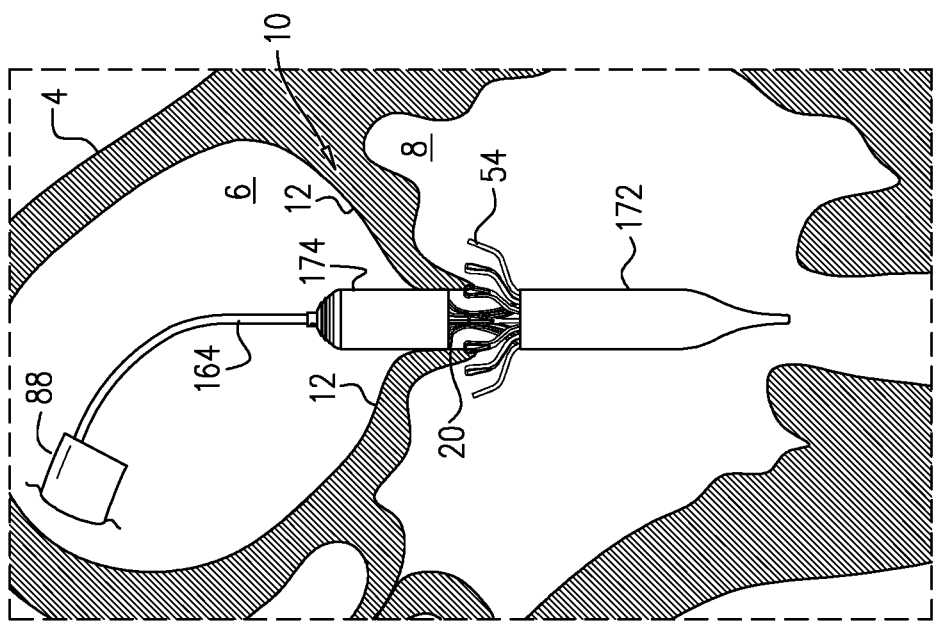

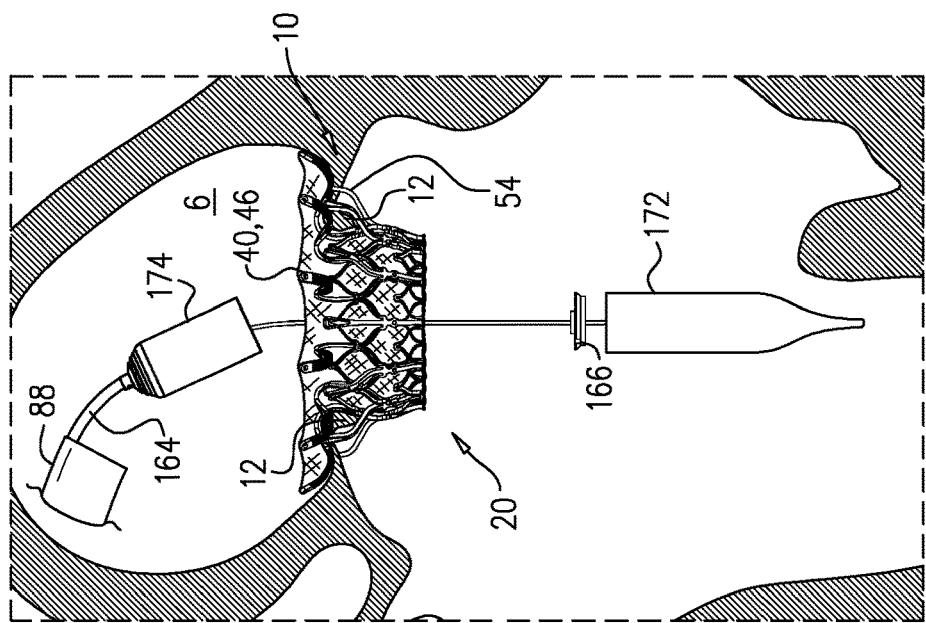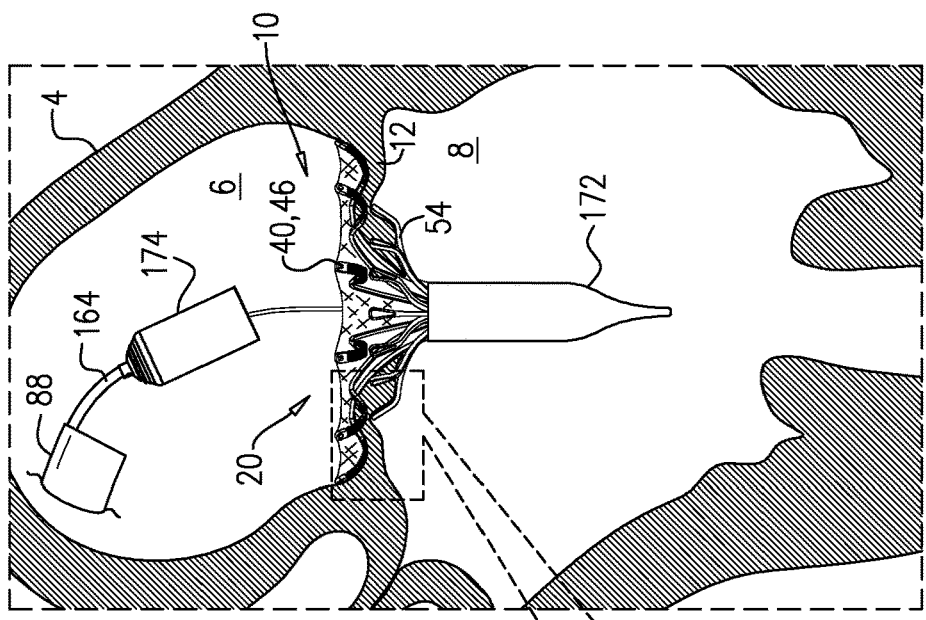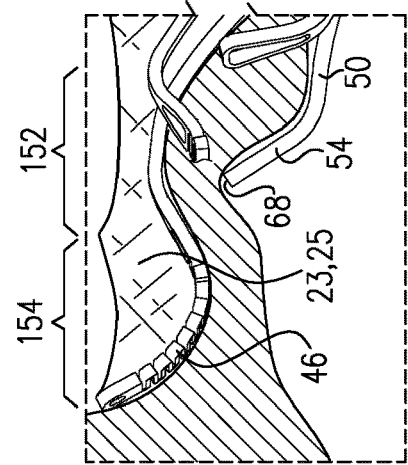

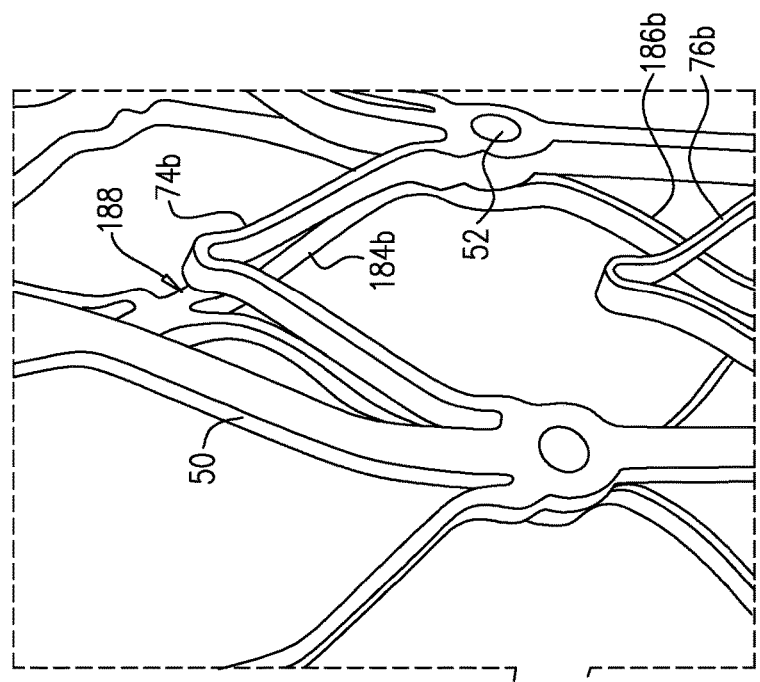
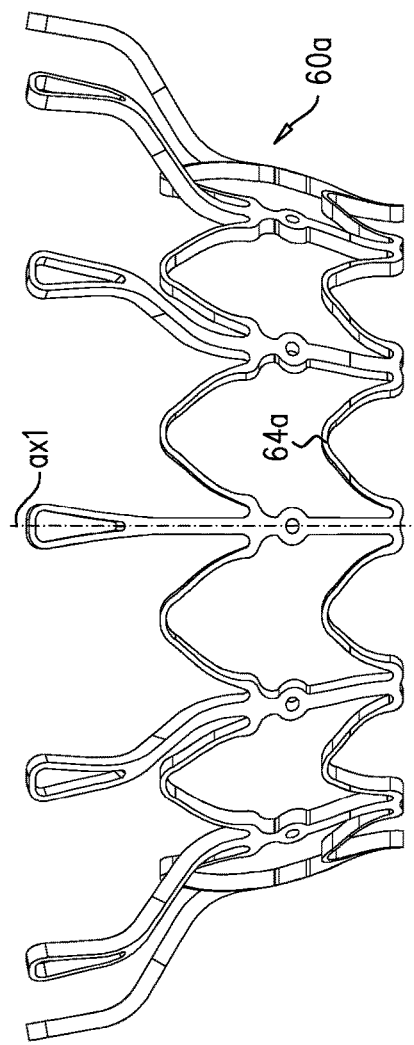
FIG. 7
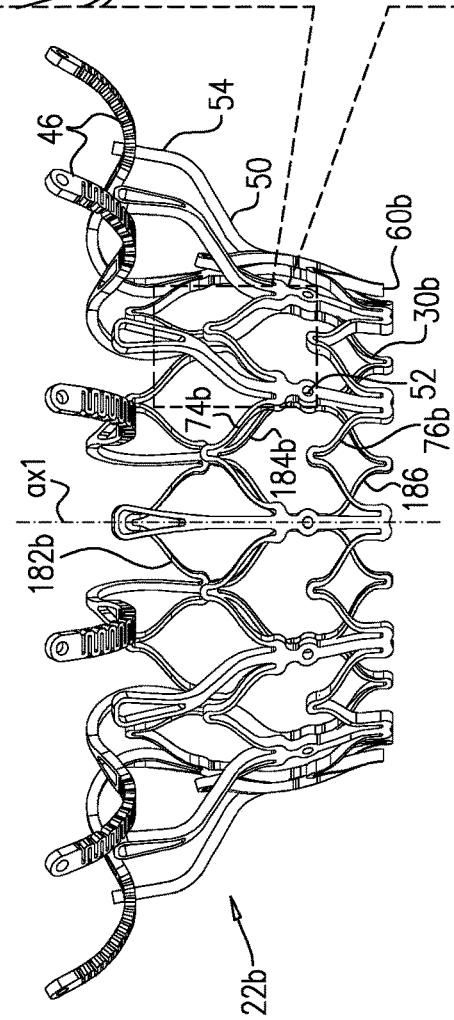
FIG. 8

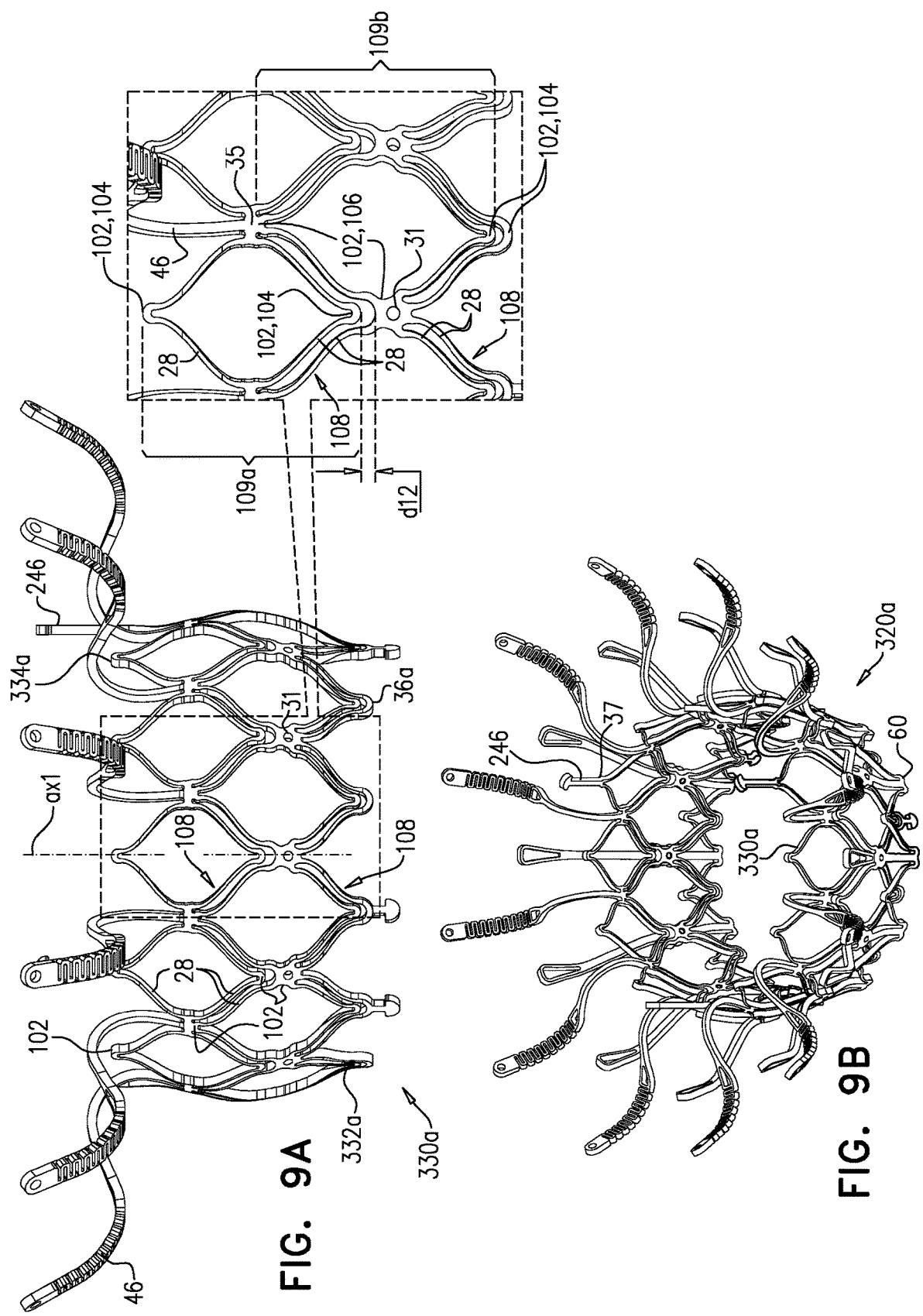

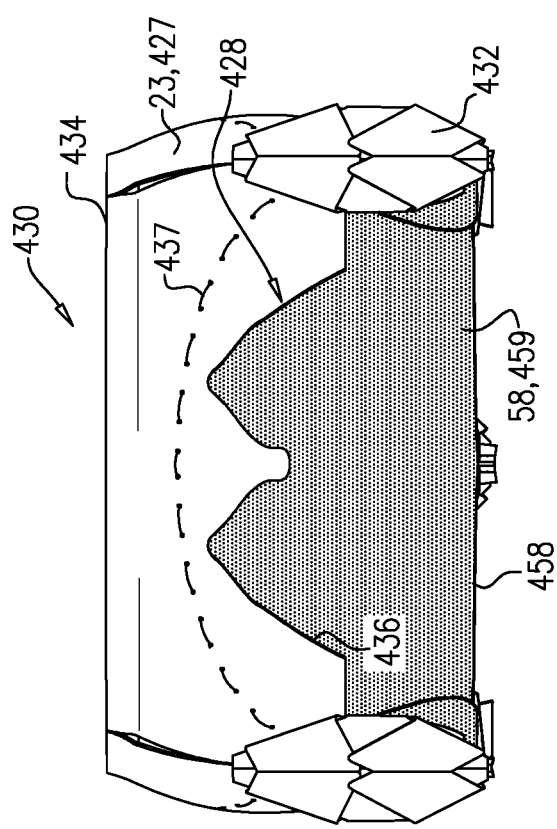
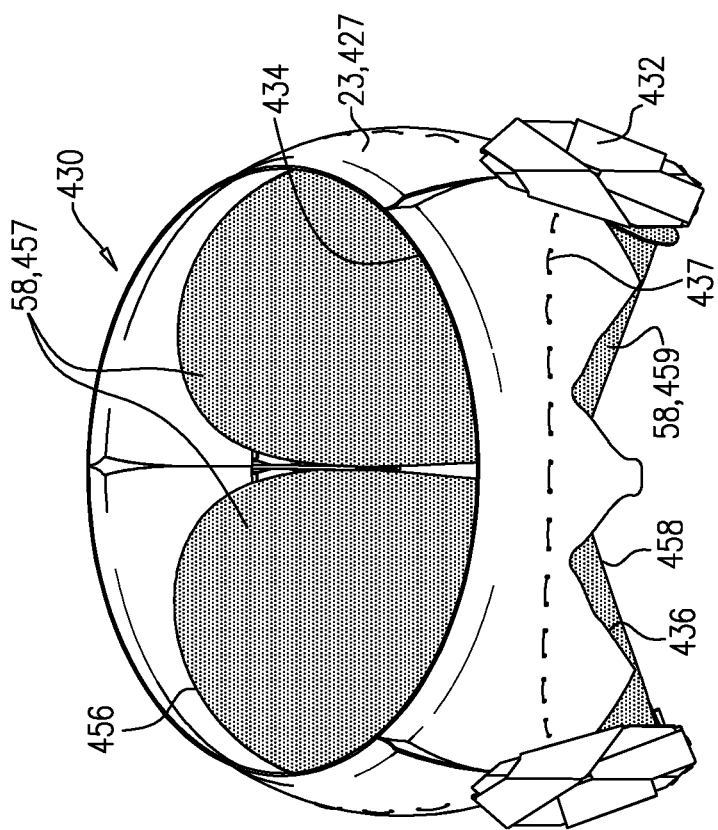
FIG. 13B
FIG. 13A

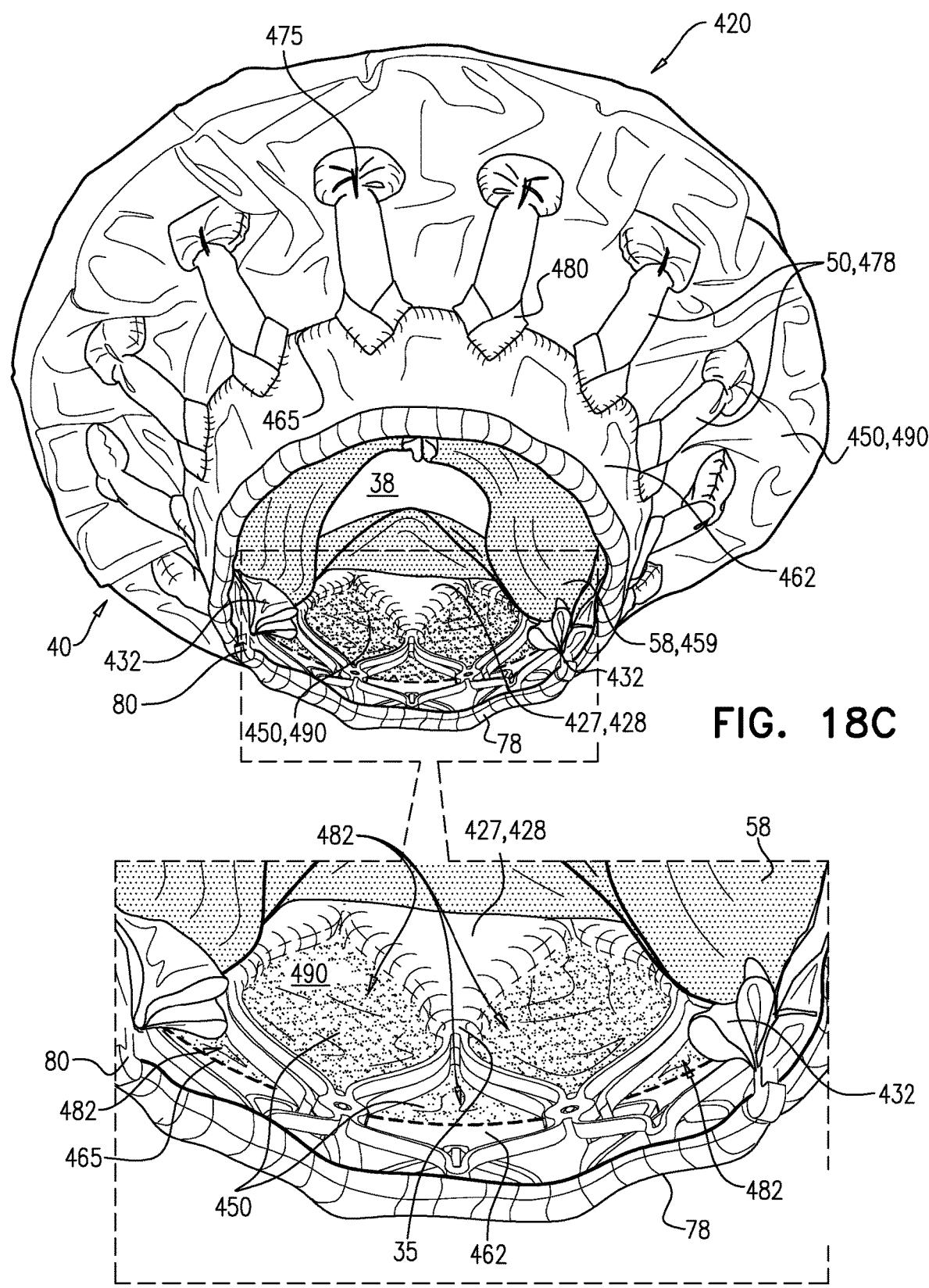

PROSTHETIC HEART VALVE

CROSS-REFERENCES TO RELATED APPLICATIONS

The present application is the US National Phase of International Patent Application PCT/IL2018/050725 to Hariton et al., filed Jul. 4, 2018, which published as WO 2019/026059, and which:
  (a) claims priority from:
  U.S. patent application Ser. No. 15/668,559 to Iamberger et al., filed Aug. 3, 2017, and entitled "Prosthetic heart valve" (now U.S. Pat. No. 10,537,426),
  U.S. provisional patent application 62/560,384 to Hariton et al., filed Sep. 19, 2017, and entitled "Prosthetic valve and methods of use," and
  U.S. patent application Ser. No. 15/956,956 to Iamberger et al., filed Apr. 19, 2018, and entitled "Prosthetic heart valve," which published as US 2019/0038405; and
  (b) is a Continuation-In-Part of U.S. patent application Ser. No. 15/956,956 to Iamberger et al., filed Apr. 19, 2018, and entitled "Prosthetic heart valve," which published as US 2019/0038405, and which is a Continuation-In-Part of U.S. patent application Ser. No. 15/668,559 to Iamberger et al., filed Aug. 3, 2017, and entitled "Prosthetic heart valve" (now U.S. Pat. No. 10,537,426), both of which are incorporated herein by reference.

FIELD OF THE INVENTION

Some applications of the present invention relate in general to valve replacement. More specifically, some applications of the present invention relate to prosthetic valves for replacement of a cardiac valve.

BACKGROUND

Ischemic heart disease causes regurgitation of a heart valve by the combination of ischemic dysfunction of the papillary muscles, and the dilatation of the ventricle that is present in ischemic heart disease, with the subsequent displacement of the papillary muscles and the dilatation of the valve annulus.

Dilation of the annulus of the valve prevents the valve leaflets from fully coapting when the valve is closed. Regurgitation of blood from the ventricle into the atrium results in increased total stroke volume and decreased cardiac output, and ultimate weakening of the ventricle secondary to a volume overload and a pressure overload of the atrium.

SUMMARY OF THE INVENTION

For some applications, an implant is provided having a tubular portion, an upstream support portion and one or more flanges. The implant is percutaneously deliverable to a native heart valve in a compressed state, and is expandable at the native valve. The implant comprises an inner frame and an outer frame. The upstream support portion is at least partly defined by the inner frame, and the flanges are at least partly defined by the outer frame. The implant is secured at the native valve by sandwiching tissue of the native valve between the upstream support portion and the flanges.

There is therefore provided, in accordance with an application of the present invention, a method for assembling a prosthetic valve, the method including:

(A) stitching a first sheet of flexible material to a frame assembly, the first sheet having (i) a greater perimeter, and (ii) a smaller perimeter that defines an opening, the frame assembly including:
  a tubular portion that circumscribes a longitudinal axis and defines a lumen along the axis,
  a plurality of arms that are coupled to the tubular portion at a first axial level with respect to the longitudinal axis, each of the arms extending radially outward from the tubular portion to a respective arm-tip, and
  a plurality of ventricular legs that are coupled to the tubular portion at a second axial level with respect to the longitudinal axis, and that extend radially outward from the tubular portion,
and stitching the first sheet to the frame assembly includes aligning the opening of the first sheet with the lumen and stitching the first sheet onto the plurality of arms;

(B) subsequently to stitching the first sheet to the plurality of arms, stitching an outer perimeter of a second sheet of flexible material to the greater perimeter of the first sheet, the second sheet being annular, and having an inner perimeter; and (C) subsequently to stitching the outer perimeter of the second sheet to the greater perimeter of the first sheet, everting the second sheet by passing the inner perimeter of the second sheet around the arm-tips.

In an application, the method further includes, prior to stitching the first sheet to the plurality of arms:
  obtaining the first sheet while the first sheet is flat, is shaped as a major arc of an annulus, and has a first arc-end and a second arc-end; and
  by attaching the first arc-end to the second arc-end, shaping the first sheet into an open frustum that has (i) the greater perimeter at a first base of the frustum, and (ii) the smaller perimeter at a second base of the frustum.

In an application, the method further includes, subsequently to everting the second sheet, stitching the inner perimeter to the tubular portion such that the ventricular legs are disposed radially outside of the second sheet.

In an application, each of the ventricular legs extends radially outward from the tubular portion at an acute angle to define a respective cleft between the leg and the tubular portion, and everting the second sheet includes positioning the inner perimeter to circumscribe the tubular portion, and tucking the inner perimeter into the cleft defined by each leg.

In an application, stitching the outer perimeter of the second piece to the greater perimeter of the first piece includes stitching the outer perimeter of the second piece to the greater perimeter of the first piece such that the inner perimeter is disposed axially away from the frame assembly, and everting the second sheet includes bringing the inner perimeter toward the frame assembly.

In an application, arms collectively define an arm-span, and the inner perimeter defines a diameter that is smaller than the arm-span.

In an application, the method further includes temporarily bending at least one arm of the plurality of arms to facilitate passing the inner perimeter of the second sheet around the arms.

In an application, the method further includes securing, within the tubular portion, a valvular assembly that includes a plurality of prosthetic leaflets and a liner, and securing the valvular assembly within the tubular portion includes stitching the liner to the tubular portion, and the method further includes stitching an upstream edge of the liner to the smaller perimeter of the first sheet.

In an application, the frame assembly further includes a plurality of projections extending axially away from the tubular portion, and stitching the upstream edge of the liner to the smaller perimeter of the first sheet includes stitching the upstream edge of the liner to the smaller perimeter of the first sheet such that the projections protrude between the upstream edge of the liner and the smaller perimeter of the first sheet.

There is further provided, in accordance with an application of the present invention, a method for assembling a prosthetic valve, the method including:
obtaining:
a frame assembly that includes:
a tubular portion that circumscribes a longitudinal axis and defines a lumen along the longitudinal axis, and
a plurality of ventricular legs that extend radially outward from the tubular portion; and
a piece of flexible material, the piece being flat, and shaped to define (i) a belt, and (ii) a plurality of elongate strips, each of the strips (i) having a first edge, a second edge, and an end, and (ii) extending from the belt along a respective strip-axis until the end, the first edge and the second edge extending, on either side of the strip-axis, from the belt to the end of the strip;
for each of the strips, forming the strip into a respective pocket by:
folding the strip over itself, about a fold-line that is orthogonal to the strip-axis, thereby forming (i) a first strip-portion that extends from the belt to the fold-line, and (ii) a second strip-portion that extends from fold-line back toward the belt; and
stitching together (i) the first strip-portion at the first edge, and the second strip-portion at the first edge, and (ii) the first strip-portion at the second edge, and the second strip-portion at the second edge, the pocket having (i) an opening defined at least in part by the end of the strip, and (ii) a tip at the fold-line; and subsequently,
dressing the frame assembly with the piece of flexible material by:
sliding each leg into a respective pocket via the opening of the respective pocket; and
wrapping the belt circumferentially around the tubular portion.

In an application, the method further includes placing a pad inside each pocket at the tip of the pocket.

In an application, the method further includes forming the pad by flattening and folding a piece of foam to form a niche, and sliding each leg into the respective pocket includes sliding each leg into the respective pocket and into the niche of the respective pad.

There is further provided, in accordance with an application of the present invention, apparatus, including an implant that includes:
a frame that has a tubular portion that circumscribes a central longitudinal axis of the implant to define a lumen along the axis;
a plurality of legs, each of the legs extending radially away from the tubular portion; and
a plurality of ribbons, each of the ribbons wrapped around a base of a respective one of the legs.

In an application, each of the legs extends radially away from the tubular portion at an acute angle to define a respective cleft between the base of the leg and the tubular portion, and each of the ribbons covers the respective cleft.

In an application, the implant is a prosthetic valve for use at a native valve of a heart of a subject, the tubular portion is a valve body, and the prosthetic valve further includes a plurality of prosthetic leaflets, disposed in the lumen, coupled to the valve body, and arranged to facilitate one-way upstream-to-downstream fluid flow through the lumen.

In an application, the implant includes an outer frame that is coupled to the tubular portion, and defines (i) a ring that circumscribes the tubular portion, and (ii) the plurality of legs, the plurality of legs being attached to the ring.

There is further provided, in accordance with an application of the present invention, a method for assembling an implant, the method including:
obtaining an assembly that includes:
a frame that has a tubular portion that circumscribes a central longitudinal axis of the implant to define a lumen along the axis; and
a plurality of legs, each of the legs extending radially away from the tubular portion; and
for each of the legs, wrapping a ribbon around a base of the leg.

In an application, each of the legs extends radially away from the tubular portion at an acute angle to define a cleft between the base of the leg and the tubular portion, and wrapping the ribbon around the base of the leg includes covering the cleft with the ribbon.

In an application, the method further includes securing the ribbon in place by stitching.

In an application, the method further includes coupling a plurality of prosthetic leaflets to the tubular portion such that the plurality of leaflets is disposed in the lumen and arranged to facilitate one-way upstream-to-downstream fluid flow through the lumen.

There is further provided, in accordance with an application of the present invention, apparatus, including:
a frame assembly that includes:
a valve body that circumscribes a longitudinal axis and defines a lumen along the axis;
a plurality of arms that are coupled to the valve body at a first axial level with respect to the longitudinal axis, each of the arms extending radially outward from the valve body to a respective arm-tip; and
a plurality of ventricular legs that are coupled to the valve body at a second axial level with respect to the longitudinal axis, and that extend radially outward from the valve body and toward the plurality of arms;
a tubular liner that lines the lumen, and that has an upstream end and a downstream end;
a plurality of prosthetic leaflets, disposed within the lumen, attached to the liner, and arranged to facilitate one-way upstream-to-downstream fluid flow through the lumen, the first axial level being upstream of the second axial level;
a first sheet of flexible material, the first sheet having (i) a greater perimeter, and (ii) a smaller perimeter that defines an opening, the first sheet being attached to the plurality of arms with the opening aligned with the lumen of the valve body; and
a second sheet of flexible material:
the second sheet having a first perimeter and a second perimeter,
the first perimeter being attached to the greater perimeter of the first sheet around the greater perimeter of the first sheet,
the second sheet extending from the first perimeter radially inwards and downstream toward the second perimeter, the second perimeter circumscribing, and attached to, the valve body at a third axial level that is downstream of the first axial level, and:

the first sheet, the second sheet, and the liner define an inflatable pouch therebetween, the first sheet defining an upstream wall of the pouch, the second sheet defining a radially-outer wall of the pouch, and the liner defining a radially-inner wall of the pouch, and the apparatus defines a plurality of windows from the lumen into the pouch, each of the windows bounded by the liner at an upstream edge of the window, and bounded by the second perimeter at a downstream edge of the window.

In an application, the pouch extends, with respect to the longitudinal axis, further upstream than the leaflets.

In an application, the first sheet covers an upstream side of the plurality of arms.

In an application, for each arm of the plurality of arms, at least most of the arm is disposed inside the pouch.

In an application, the plurality of arms defines an arm-span, and the second perimeter defines a diameter that is smaller than the arm-span.

In an application, the pouch extends radially outward further than the plurality of arms.

In an application, the pouch circumscribes the valve body.

In an application, the upstream end of the tubular liner is circular.

In an application, the upstream edge of each of the windows is the shape of a capital letter M.

In an application, the third axial level is upstream of the second axial level.

In an application, the smaller perimeter of the first sheet is attached to the upstream end of the liner.

In an application, the apparatus includes a circumferential stitch line, radially inward from the arm-tips, at which the first sheet is stitched to the second sheet.

In an application, at the circumferential stitch line, the arms are sandwiched between the first sheet and the second sheet.

In an application, the circumferential stitch line isolates the arm-tips from the pouch.

In an application, each of the leaflets is attached to the liner upstream of the plurality of windows.

In an application, each of the leaflets has a free edge that is disposed downstream of the third axial level.

In an application, the apparatus further includes a third sheet of flexible material attached to the frame assembly, the third sheet defining a belt that circumscribes the valve body downstream of the ventricular legs.

In an application, an upstream edge of the belt is attached circumferentially to the second perimeter of the second sheet.

In an application, the ventricular legs extend radially outward between the belt and the second sheet.

In an application, the third sheet further defines a plurality of elongate pockets extending from the upstream edge of the belt, each of the ventricular legs disposed within a respective elongate pocket.

There is further provided, in accordance with an application of the present invention, apparatus for use at a native valve of a heart of a subject, the apparatus including a prosthetic valve that includes:

a tubular valve body, defined by a repeating pattern of cells that extends around a central longitudinal axis of the prosthetic valve to define a lumen;

a plurality of prosthetic leaflets, disposed in the lumen, coupled to the valve body, and arranged to facilitate one-way upstream-to-downstream fluid flow through the lumen, thereby defining an upstream end of the prosthetic valve and a downstream end of the prosthetic valve, and:

the pattern of cells includes a plurality of first-row cells in a first row and a plurality of second-row cells in a second row, each of the first-row cells connected to two adjacent first-row cells at respective first-row-cell connection nodes, the first row is closer than the second row to the upstream end of the prosthetic valve, and the second-row cells are tessellated with the first-row cells such that an upstream extremity of each second-row cell is coincident with a respective first-row-cell connection node;

a plurality of arms, each of the arms extending from the upstream extremity of a respective second-row cell; and a plurality of elongate projections, each of the projections extending from an upstream extremity of a respective first-row cell, and terminating in a nub that facilitates snaring of the projection.

In an application, the apparatus further includes an annular sheet that defines an opening, the sheet being stitched to the arms such that the opening is aligned with the lumen of the valve body, and the arms and the annular sheet form an annular upstream support portion, and each of the elongate protrusions extends through the opening.

In an application, the apparatus includes a monolithic valve frame that includes the valve body, the plurality of arms, and the plurality of projections, and the apparatus further includes an outer frame that circumscribes the valve frame, and includes a plurality of legs that extend radially outward from the valve body and toward the arms, each of the legs terminating in a flange that is configured to engage ventricular tissue of the heart.

In an application, the second row includes a number of second-row cells, the plurality of arms includes a number of arms that is equal to the number of second-row cells, and an arm of the plurality of arms extends from the upstream extremity of every one of the second-row cells.

In an application, the first row includes a number of first-row cells, and the plurality of projections includes a number of projections that is smaller than the number of first-row cells.

In an application, the plurality of arms is configured to be positioned in an atrium of the heart, upstream of the native valve.

In an application, the plurality of elongate projections is configured to be positioned in an atrium of the heart, upstream of the native valve.

In an application, the apparatus includes fewer projections than arms.

In an application, the apparatus includes no more than half as many projections as arms.

In an application, the apparatus includes a quarter as many projections as arms.

In an application, each of the projections has two circumferentially-neighboring projections, and the plurality of arms and the plurality of projections are arranged such that at least two of the arms are disposed circumferentially between each projection and each of its circumferentially-neighboring projections.

In an application, the plurality of arms and the plurality of projections are arranged such that four of the arms are disposed circumferentially between each projection and each of its circumferentially-neighboring projections.

In an application, each of the projections has a projection-length measured from the upstream extremity of the respective first-row cell, and each of the arms has an arm-length measured from the upstream extremity of the respective second-row cell, the arm-length being greater than the projection-length.

In an application, the arm-length is 4-10 times greater than the projection-length.

In an application, the arm-length is 20-26 mm.

In an application, the projection-length is 2-10 mm.

In an application, each of the arms (i) has a narrow portion that is attached to, and extends from, the upstream extremity of the respective second-row cell, and (ii) at a widening zone, widens into a wide portion that extends from the narrow portion, and is wider than the narrow portion.

In an application, for each of the arms, the wide portion is 2-4 times wider than the narrow portion.

In an application, for each of the arms, the narrow portion is 0.4-0.6 mm wide and the wide portion is 1.4-1.8 mm wide.

In an application, for each of the projections, the nub is 1-2 mm wide.

In an application, the wide portion of each of the arms has a wide-portion length, the nub of each of the projections has a nub length, and the wide-portion length is at least 10 times greater than the nub length.

In an application, the apparatus includes a monolithic valve frame that includes the valve body, the plurality of arms, and the plurality of projections, the valve frame being manufactured by:

cutting the valve frame from a metallic tube to form a raw valve-frame structure in which the arms and the projections extend axially from the valve body, and shape-setting the raw valve-frame structure to form a shape-set valve-frame structure in which the valve body is wider than in the raw valve-frame structure, and the arms extend radially outward from the valve body.

In an application, in the raw valve-frame structure, the nub is axially closer than the wide portion to the valve body.

In an application, in the shape-set valve-frame structure, the projections do not extend radially outward from the valve body.

In an application, in the shape-set valve-frame structure, the projections extend axially from the valve body.

In an application, the narrow portion has a narrow-portion length that is at least 40 percent of the arm-length.

In an application, the narrow-portion length is greater than the projection-length.

In an application, the narrow-portion length is 1.5-3 times greater than the projection-length.

In an application, the wide portion has a wide-portion length that is at least 40 percent of the arm-length.

There is further provided, in accordance with an application of the present invention, apparatus for use at a heart of a subject, the apparatus including:

a prosthetic valve that includes:

a tubular portion that circumscribes a longitudinal axis of the prosthetic valve and defines a lumen along the axis;

a plurality of prosthetic leaflets arranged within the lumen so as to facilitate one-way upstream-to-downstream fluid flow through the lumen, thereby defining an upstream end of the prosthetic valve and a downstream end of the prosthetic valve;

an upstream support portion coupled to the tubular portion; and a plurality of ventricular legs coupled to the tubular portion downstream of the upstream support portion, each of the legs having a base, and extending from the base to a leg-tip; and a delivery tool having a proximal portion and a distal portion, the tool including:

at the proximal portion of the tool, an extracorporeal controller;

a shaft, extending from the controller to the distal portion of the tool;

at the distal portion of the tool, a mount, coupled to the shaft, and shaped to engage a portion of the prosthetic valve; and at the distal portion of the tool, a capsule including one or more capsule portions, the capsule being dimensioned for percutaneous delivery to the heart while the delivery tool is in a delivery state thereof, and:

(a) the prosthetic valve is compressible into a compressed state in which (i) the prosthetic valve is housed by the capsule (ii) the prosthetic valve is engaged with the mount, and (iii) the delivery tool is in the delivery state, (b) while the delivery tool is in the delivery state and the prosthetic valve, is in the compressed state, the extracorporeal controller is operable to transition the delivery tool from the delivery state into an intermediate state by moving the one or more capsule portions axially with respect to the mount, the transitioning of the delivery tool into the intermediate state transitioning the prosthetic valve into a partially-expanded state in which:

the upstream support portion extends radially outward from the tubular portion, a downstream surface of the upstream support portion defines (i) an annular concave region extending radially between a concave-region inner radius and a concave-region outer radius, and (ii) an annular convex region, radially outward from the concave region, extending radially between a convex-region inner radius and a convex-region outer radius, and for each of the ventricular legs:

the leg extends from the base radially outward and in an upstream direction, and the leg-tip is disposed radially between the concave-region inner radius and the concave-region outer radius, and (c) while the delivery tool is in the intermediate state and the prosthetic valve is in the partially-expanded state, the extracorporeal controller is operable to transition the delivery tool from the intermediate state into an open state by moving the one or more capsule portions axially with respect to the mount, the transitioning of the delivery tool into the open state transitioning the prosthetic valve into an expanded state in which:

the upstream support portion extends radially outward from the tubular portion, the downstream surface of the upstream support portion defines the annular concave region and the annular convex region, and for each of the ventricular legs:

the leg extends from the base radially outward and in an upstream direction, and the leg-tip is disposed radially between the convex-region inner radius and the convex-region outer radius.

There is further provided, in accordance with an application of the present invention, apparatus, including:

a tubular frame that circumscribes a longitudinal axis so as to define a lumen along the axis, the tubular frame having a cellular structure defined by a plurality of metallic elements with spaces therebetween;

a plurality of prosthetic leaflets, coupled to the tubular frame, disposed within the lumen, and arranged to provide unidirectional flow of blood from an upstream end of the lumen to a downstream end of the lumen; and an outer frame, coupled to the tubular frame, and including:

a first ring defined by a pattern of alternating first-ring peaks and first-ring troughs, the first-ring peaks being longitudinally closer than the first-ring troughs to the upstream end, and the first-ring troughs being longitudinally closer than the first-ring peaks to the downstream end;

a second ring defined by a pattern of alternating second-ring peaks and second-ring troughs, the second-ring peaks being longitudinally closer than the second-ring troughs to the upstream end, and the second-ring troughs being longitudinally closer than the second-ring peaks to the downstream end; and a plurality of legs, each of the legs coupled to the first ring and the second ring, and extending radially outward from the longitudinal axis, and:

each of the first-ring peaks is disposed directly radially outward from a respective part of the tubular frame, each of the second-ring peaks is disposed directly radially outward from a respective space in the tubular frame, and neither the first-ring peaks nor the second-ring peaks are in contact with the tubular frame.

In an application, the first ring is closer than the second ring to the upstream end.

There is further provided, in accordance with an application of the present invention, apparatus, including:

a tubular valve body having an upstream end and a downstream end, and having a central longitudinal axis, and defining a lumen along the axis; and a plurality of prosthetic leaflets, disposed within the lumen, and configured to facilitate one-way movement of fluid through the lumen in an upstream-to-downstream direction, and:

the valve body has a cellular structure defined by a plurality of joists connected at a plurality of nodes, the joists and nodes delimiting cells of the cellular structure, the plurality of nodes including minor nodes at which 2-4 joists are connected, and major nodes at which 6-8 joists are connected, and the cells of the cellular structure include a first circumferential row of first-row cells, each of the first-row cells being connected to each of its circumferentially-adjacent first-row cells at a respective one of the major nodes, and being longitudinally delimited by two of the minor nodes.

In an application, at the minor nodes exactly two joists are connected.

In an application, at the major nodes exactly six joists are connected.

In an application, at the major nodes exactly eight joists are connected.

In an application, the first circumferential row includes exactly 12 first-row cells.

In an application, the first circumferential row includes exactly 9 first-row cells.

In an application, the first circumferential row includes exactly 12 major nodes at which each of the first-row cells is connected to each of its circumferentially-adjacent first-row cells.

In an application, the first circumferential row includes exactly 9 major nodes at which each of the first-row cells is connected to each of its circumferentially-adjacent first-row cells.

In an application, the cellular structure defines exactly 24 major nodes.

In an application, the cellular structure defines exactly 18 major nodes.

In an application, for each of the first-row cells, the first-row cell is not connected to another cell at the two minor nodes that longitudinally delimit the first-row cell.

In an application, the apparatus includes a frame assembly that includes (i) an inner frame that defines the valve body, and (ii) an outer frame that circumscribes the valve body, and is coupled to the inner frame by being fixed to a plurality of the major nodes of the valve body.

In an application, the cellular structure further includes a second circumferential row of second-row cells, each of the second-row cells being connected to each of its circumferentially-adjacent second-row cells at a respective one of the major nodes, and being longitudinally delimited by at least one of the major nodes.

In an application, each of the second-row cells is also longitudinally delimited by one of the minor nodes.

In an application, each of the respective major nodes at which the circumferentially-adjacent first-row cells are connected is also a major node that longitudinally-delimits a second-row cell.

In an application, all the cells of the cellular structure of the valve body are either first-row cells or second-row cells.

In an application, the apparatus includes a frame assembly that includes (i) an inner frame that defines the valve body, and (ii) an outer frame that circumscribes the valve body, and is coupled to the inner frame by being fixed to the major nodes at which the circumferentially-adjacent second-row cells are connected.

In an application, each of the first-row cells and each of the second-row cells is delimited by exactly four nodes.

In an application, the first and second circumferential rows are disposed at opposing ends of the valve body.

In an application, the first circumferential row is disposed at the upstream end of the valve body, and the second circumferential row is disposed at the downstream end of the valve body.

There is further provided, in accordance with an application of the present invention, apparatus, including:

a tubular valve body having an upstream end and a downstream end, and having a central longitudinal axis, and defining a lumen along the axis; and a plurality of prosthetic leaflets, disposed within the lumen, and configured to facilitate one-way movement of fluid through the lumen in an upstream-to-downstream direction, and:

the valve body has a cellular structure defined by a plurality of joists connected at a plurality of nodes, the joists and nodes delimiting cells of the cellular structure, the plurality of nodes including:

minor nodes at which 2-4 joists are connected, and which are arranged in minor-node rows, each minor-node row circumscribing the longitudinal axis at a respective minor-node-row longitudinal site, and major nodes at which 6-8 joists are connected, and which are arranged in major-node rows, each major-node row circumscribing the longitudinal axis at a respective major-node-row longitudinal site, and along at least part of the longitudinal axis, the minor-node-row longitudinal sites alternate with the major-node-row longitudinal sites.

In an application, each minor-node row includes exactly 12 minor nodes, and each major-node row includes exactly 12 major nodes.

In an application, each minor-node row includes exactly 9 minor nodes, and each major-node row includes exactly 9 major nodes.

In an application, the cellular structure defines exactly 24 major nodes.

In an application, the cellular structure defines exactly 18 major nodes.

In an application, at the minor nodes exactly two joists are connected.

In an application, at the major nodes exactly six joists are connected.

In an application, at the major nodes exactly eight joists are connected.

In an application, along at least the part of the longitudinal axis, at least 3 minor-node-row longitudinal sites alternate with at least 2 major-node-row longitudinal sites.

There is further provided, in accordance with an application of the present invention, apparatus, including a prosthetic valve, the prosthetic valve including:
  a frame assembly, including:
    an inner frame, defining a tubular valve body having an upstream end and a downstream end, and having a central longitudinal axis, and defining a lumen along the axis; and
    an outer frame that circumscribes the valve body; and
  a plurality of prosthetic leaflets, disposed within the lumen, and configured to facilitate one-way movement of fluid through the lumen in an upstream-to-downstream direction, and:
    the valve body has a cellular structure defined by a plurality of joists connected at a plurality of nodes, the joists and nodes delimiting cells of the cellular structure, the plurality of nodes including minor nodes at which 2-4 joists are connected, and major nodes at which 6-8 joists are connected, and
    the outer frame is coupled to the inner frame by being fixed to major nodes of the valve body.

In an application, at the minor nodes exactly two joists are connected.

In an application, at the major nodes exactly six joists are connected.

In an application, at the major nodes exactly eight joists are connected.

In an application, the outer frame is coupled to the inner frame by being fixed to exactly 12 major nodes of the valve body.

In an application, the outer frame is coupled to the inner frame by being fixed to exactly 9 major nodes of the valve body.

There is further provided, in accordance with an application of the present invention, apparatus, including:
  an implant frame, having an upstream end and a downstream end, and having a central longitudinal axis, and defining a lumen along the axis and:
    the implant frame has a cellular structure defined by a plurality of joists connected at a plurality of nodes arranged in node rows, each node row circumscribing the longitudinal axis at a respective longitudinal site, the joists and nodes delimiting cells of the cellular structure, the plurality of nodes including:
      minor nodes at which 2-4 joists are connected, and which are arranged in node rows that are minor-node rows, and
      major nodes at which 6-8 joists are connected, and which are arranged in node rows that are major-node rows, and
      a most upstream node row and a most downstream node row are minor-node rows.

In an application, each of the minor-node rows is at a respective minor-node-row longitudinal site, each of the major-node rows is at a respective major-node-row longitudinal site, and along at least part of the longitudinal axis, the minor-node-row longitudinal sites alternate with the major-node-row longitudinal sites.

In an application, each minor-node row includes exactly 12 minor nodes, and each major-node row includes exactly 12 major nodes.

In an application, each minor-node row includes exactly 9 minor nodes, and each major-node row includes exactly 9 major nodes.

In an application, the cellular structure defines exactly 24 major nodes.

In an application, the cellular structure defines exactly 18 major nodes.

In an application, at the minor nodes exactly two joists are connected.

In an application, at the major nodes exactly six joists are connected.

In an application, at the major nodes exactly eight joists are connected.

In an application, at least two major-node rows are disposed longitudinally between the most upstream node row and the most downstream node row.

In an application, at least two minor-node rows are disposed between the most upstream node row and the most downstream node row.

In an application, the node rows are arranged with respect to the longitudinal axis in the following order:
  a first minor-node row, which is the most upstream node row,
  a first major-node row,
  a second minor-node row,
  a second major-node row,
  a third minor-node row, and
  a fourth minor-node row, which is the most downstream node row.

There is further provided, in accordance with an application of the present invention, apparatus, including:
  a tubular valve body having an upstream end and a downstream end, having a central longitudinal axis, defining a lumen along the axis, and including a plurality of connected joists; and
  a plurality of prosthetic leaflets, disposed within the lumen, and configured to facilitate one-way movement of fluid through the lumen in an upstream-to-downstream direction, and:
    the valve body has a cellular structure defined by the joists delimiting cells, the cellular structure including a first circumferential row of cells, and a second circumferential row of cells that are tessellated with the cells of the first row, and
    the joists that delimit the cells of the first row do not delimit cells of the second row.

There is further provided, in accordance with an application of the present invention, apparatus for use with a native heart valve of a subject, the apparatus including a prosthetic valve, the prosthetic valve including:
  a valve body, shaped to define a lumen therethrough, the lumen defining a longitudinal axis of the prosthetic valve;
  an upstream support portion, including:
    a plurality of arms, coupled to and extending radially outward from the valve body; and
    an annular sheet disposed over and supported by the arms; and a plurality of elongate projections extending from the valve body in an upstream direction through the annular sheet; and a valve member, disposed within the lumen of the valve body.

In an application, the prosthetic valve includes a nub at the end of each projection.

In an application, the prosthetic valve includes the same number of arms as elongate projections.

In an application, the elongate projections curve inwards toward the longitudinal axis.

In an application:

the prosthetic valve includes a valve frame that defines the valve body, has a cellular structure, and has an upstream end that defines alternating peaks and troughs, the peaks being further upstream than the troughs, the arms are attached to the valve body at the troughs, and the elongate projections are attached to the valve body at the peaks.

There is further provided, in accordance with an application of the present invention, a method for augmenting, with a soft pad, a tissue-engaging flange of a frame of a prosthetic valve, the tissue-engaging flange being configured to facilitate anchoring of the prosthetic valve, the method including:

affixing, to the flange, a model of the soft pad;

subsequently, forming a mold by:

positioning the frame such that the model is supported within a fluid of a first substance while the first substance solidifies, and subsequently, removing the model from the first substance, leaving a cavity in the solidified first substance;

subsequently, removing the model from the flange;

subsequently, forming the pad by:

placing the flange in contact with a second substance by repositioning the frame such that the flange is supported within the cavity, and introducing a fluid of the second substance to the cavity, and while the flange remains in contact with the second substance, allowing the second substance to solidify and become affixed to the flange; and removing, from the cavity, the flange with the formed pad affixed thereto, the formed pad being of the solidified second substance.

In an application, the solidified second substance is a solid silicone material, and the step of allowing the second substance to solidify and become affixed to the flange, includes allowing the second substance to solidify into the solid silicone material and become affixed to the flange.

In an application, the solidified second substance is a foam, and the step of allowing the second substance to solidify and become affixed to the flange, includes allowing the second substance to solidify into the foam and become affixed to the flange.

In an application:

the frame has a plurality of flanges, the step of affixing the model to the flange includes affixing a respective plurality of models to the plurality of flanges, the step of forming the mold includes forming a mold that includes a respective plurality of cavities using the respective plurality of models, and forming the pad includes forming a plurality of pads on the respective plurality of flanges by:

placing the plurality of flanges in contact with the second substance by repositioning the frame such that the flanges are supported in respective cavities, and introducing the fluid of the second substance to the cavities, and while the flanges remain in contact with the second substance, allowing the second substance to solidify and become affixed to the flanges.

In an application, the frame is a first frame of the prosthetic valve, and the prosthetic valve includes a second frame, and the method further includes, subsequently to forming the plurality of pads, coupling the first frame to the second frame.

In an application, the second frame has an upstream end, a downstream end, and a longitudinal axis therebetween, and coupling the first frame to the second frame includes coupling the first frame to the second frame such that the pads are arranged circumferentially around the second frame longitudinally between the upstream end and the downstream end, exclusive.

There is further provided, in accordance with an application of the present invention, apparatus for use with a native heart valve of a subject, the apparatus including a prosthetic valve, the prosthetic valve including:

a frame assembly that defines:

a valve body, shaped to define a lumen therethrough, the lumen defining a longitudinal axis of the prosthetic valve;

a plurality of arms, coupled to the valve body; and a valve member, disposed within the lumen of the valve body, and:

the prosthetic valve has a compressed state in which the prosthetic valve is transluminally deliverable to the native heart valve, and is expandable at the native heart valve into an expanded state in which the valve member facilitates one-way blood flow through the lumen, in the expanded state, the plurality of arms extends radially outward from the valve body, and in the compressed state, the plurality of arms defines a ball at an end of the valve body.

In an application, the frame assembly includes a monolithic valve frame that defines the valve body and the plurality of arms.

In an application:

the frame assembly includes a first frame and a second frame, the first frame defines the valve body and the plurality of arms, the second frame circumscribes the first frame and defines a plurality of flanges, and in the expanded state the plurality of flanges extends radially outward from the valve body and toward the plurality of arms.

In an application, in the compressed state, the frame assembly defines a waist longitudinally between the valve body and the ball.

In an application, at the waist a transverse diameter of the frame assembly is less than 40 percent of a greatest transverse width of the ball.

In an application, at the waist the frame assembly has a transverse diameter that is less than 5 mm.

In an application, a greatest transverse diameter of the ball is 8-12 mm.

There is further provided, in accordance with an application of the present invention, apparatus, including:
a prosthetic valve, including:
a frame assembly that defines:
a valve body, shaped to define a lumen therethrough, the lumen defining a longitudinal axis of the prosthetic valve;
a plurality of arms, coupled to the valve body; and
a valve member, disposed within the lumen of the valve body; and
a capsule that includes a circumferential wall that defines a cavity, and the apparatus has a delivery state in which:
the prosthetic valve is in a compressed state, and is disposed within the cavity,
the prosthetic valve and the capsule define a toroidal gap therebetween, the toroidal gap circumscribing the longitudinal axis of the prosthetic valve,
the valve body extends in a first longitudinal direction away from the toroidal gap, and the arms extend in a second longitudinal direction away from the toroidal gap.

In an application, the valve member defines an upstream direction and a downstream direction of the prosthetic valve, and the first longitudinal direction is the downstream direction and the second longitudinal direction is the upstream direction.

In an application, the frame assembly includes a first frame, and a second frame that circumscribes the first frame, and in the delivery state, the second frame is disposed only downstream of the toroidal gap, but the first frame is disposed both upstream and downstream of the toroidal gap.

In an application, the frame assembly further defines a plurality of flanges that, in the delivery state, extend from a coupling point with the valve body, and toward the toroidal gap, such that the toroidal gap is disposed between tips of the flanges and the arms.

In an application, the toroidal gap is defined between the tips of the flanges and a downstream side of the arms.

There is further provided, in accordance with an application of the present invention, apparatus for use with a native heart valve of a subject, the apparatus including:
a valve body, having an upstream end and a downstream end, shaped to define a lumen from the upstream end to the downstream end, the lumen defining a longitudinal axis of the apparatus, and the valve body having;
a fabric liner, lining the lumen;
a valve member, disposed within the lumen of the valve body; and
a polytetrafluoroethylene ring coupled to the downstream end of the valve body such that the ring circumscribes the lumen at the downstream end of the valve body.

In an application, the ring is stitched to the downstream end of the valve body by stitches that wrap around the ring but do not pierce the ring.

In an application, the valve body includes an expandable frame that defines the lumen, the fabric liner lining the lumen defined by the expandable frame, and the polytetrafluoroethylene ring covers the valve frame at the downstream end.

The present invention will be more fully understood from the following detailed description of applications thereof, taken together with the drawings, in which:

BRIEF DESCRIPTION OF THE DRAWINGS

FIGS. 1A-E and 2 are schematic illustrations of an implant and a frame assembly of the implant, in accordance with some applications of the invention;

FIGS. 3A-F are schematic illustrations showing the implantation of the implant at a native valve of a heart of a subject, in accordance with some applications of the invention;

FIG. 7 is a schematic illustration of an outer frame of a frame assembly of an implant, in accordance with some applications of the invention;

FIG. 8 is a schematic illustration of a frame assembly, in accordance with some applications of the invention;

FIGS. 9A-B are schematic illustrations of an inner frame, and an implant comprising the inner frame, in accordance with some applications of the invention;

FIGS. 13A-E, 14A-D, 15A-C, 16A-C, 17, 18A-C, and 19 are schematic illustrations of an implant, and steps in the assembly of the implant, in accordance with some applications of the invention.

DETAILED DESCRIPTION OF EMBODIMENTS

Reference is made to FIGS. 1A-E and 2, which are schematic illustrations of an implant 20 and a frame assembly 22 of the implant, in accordance with some applications of the invention. Implant 20 serves as a prosthetic valve for use at a native heart valve of a subject—typically the mitral valve. Implant 20 has a compressed state for minimally-invasive (typically transluminal, e.g., transfemoral) delivery, and an expanded state into which the implant is transitioned at the native heart valve, and in which the implant provides prosthetic valve functionality. Implant 20 comprises frame assembly 22, flexible sheeting 23, and a valve member, such as prosthetic leaflets 58.

Figure 1A:
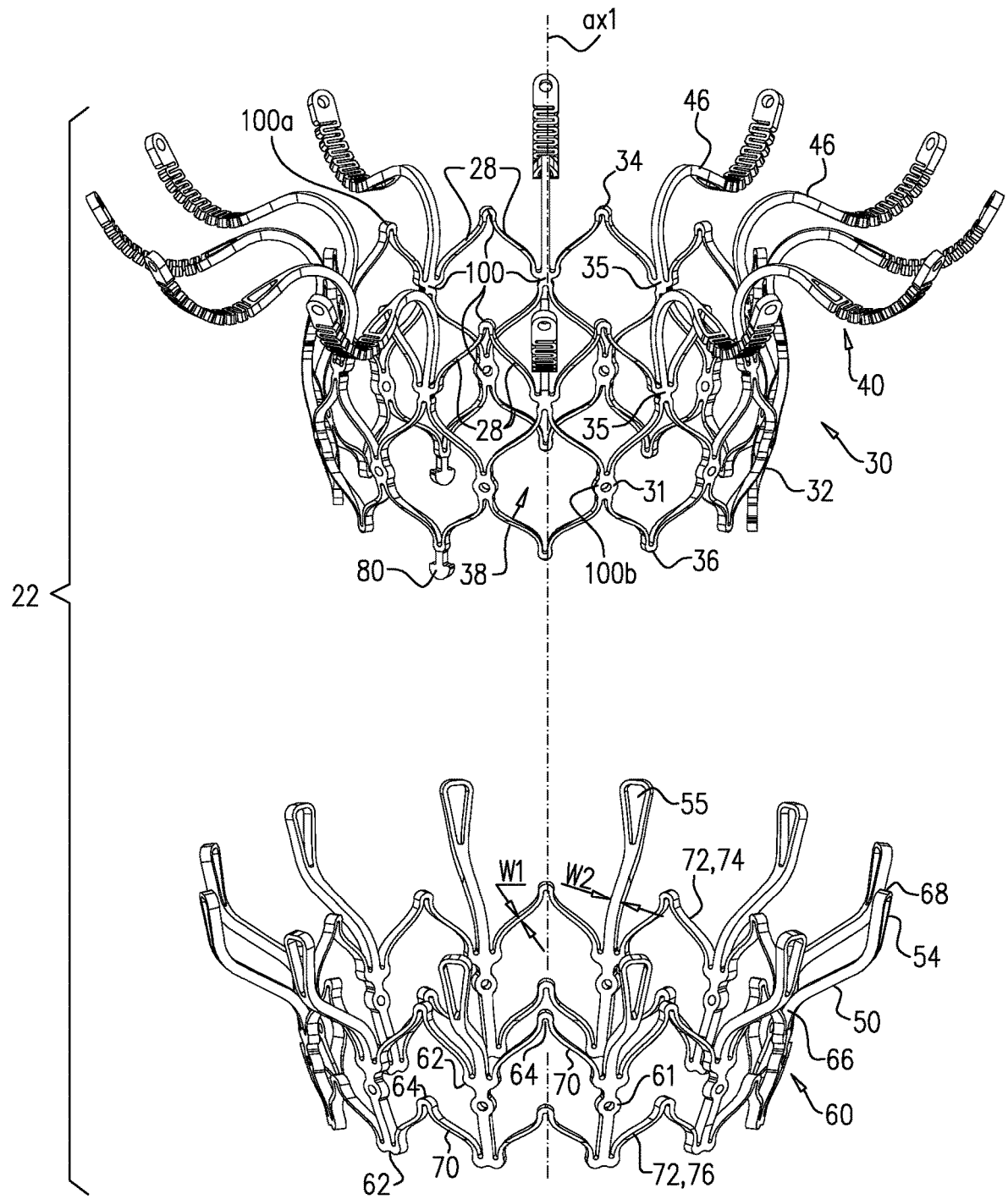
Figure 1B:
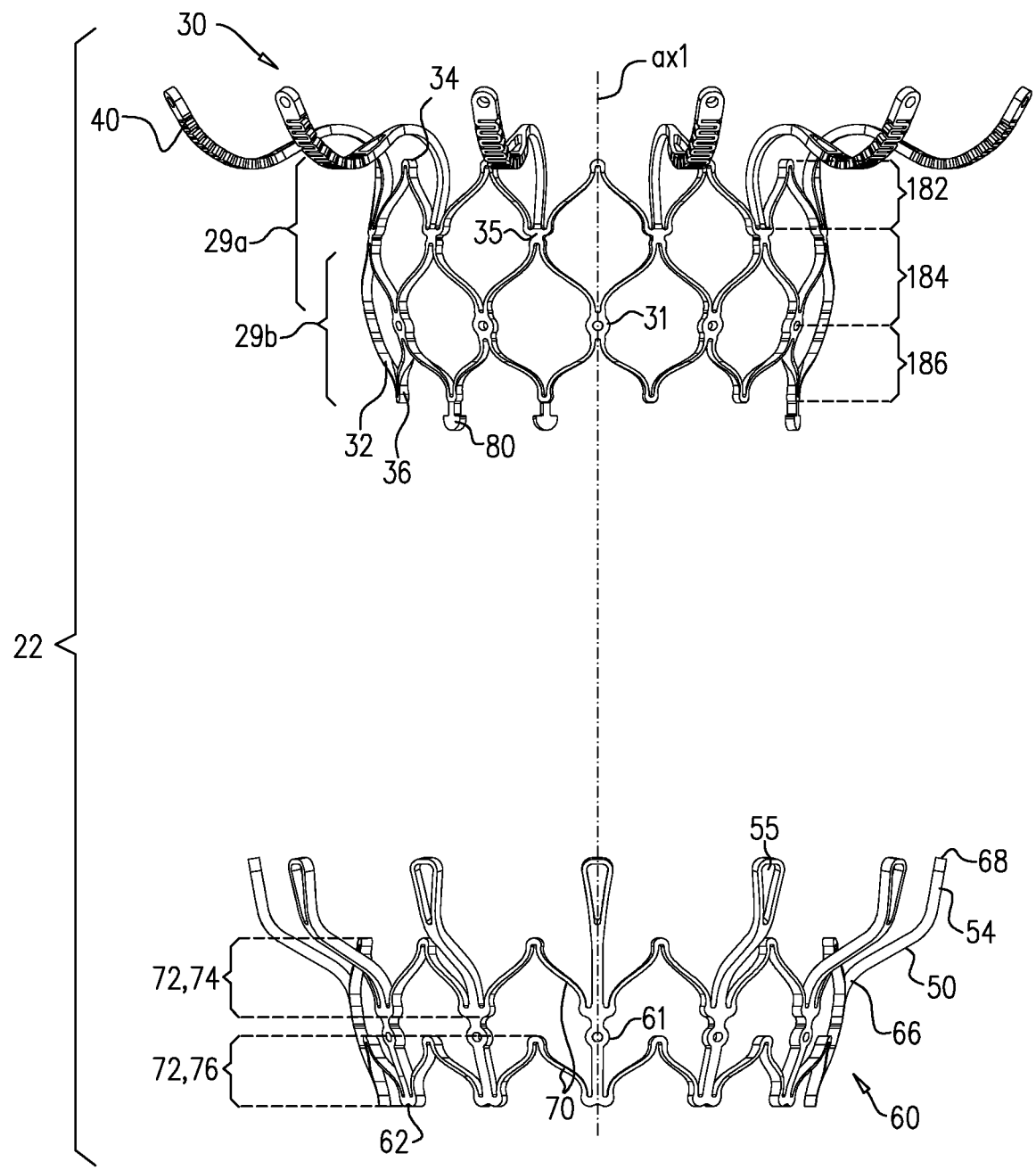

FIGS. 1A-E show implant 20 and frame assembly 22 in the expanded state. For clarity, FIGS. 1A-D show frame assembly 22 alone. FIG. 1A shows an isometric exploded view of frame assembly 22, and FIG. 1B shows a side exploded view of the frame assembly. FIGS. 1C and 1D are side- and top-views, respectively, of frame assembly 22, assembled. FIG. 1E is a perspective view of implant 20, including sheeting 23 and leaflets 58.

Implant 20 has an upstream end 24, a downstream end 26, and defines a central longitudinal axis ax1 therebetween. Frame assembly 22 comprises a valve frame 30 that comprises a valve body (which is a generally tubular portion) 32 that has an upstream end 34 and a downstream end 36, and is shaped to define a lumen 38 through the valve body from its upstream end to its downstream end. Valve body 32 circumscribes axis ax1, and thereby defines lumen 38 along the axis. Throughout this application, including the specification and the claims, unless stated otherwise, "upstream" and "downstream," e.g., with respect to the ends of implant 20, are defined with respect to the longitudinal axis of implant 20, by the orientation and functioning of leaflets 58, which facilitate one-way upstream-to-downstream fluid flow through lumen 38.

Valve frame 30 further comprises a plurality of arms 46, each of which, in the expanded state, extends radially outward from valve body 32. In this context, the term "extends radially outward" is not limited to extending in a straight line that is orthogonal to axis ax1, but rather, and as shown for arms 46, includes extending away from axis ax1 while curving in an upstream and/or downstream direction. Typically, and as shown, each arm 46 extends from valve body 32 in an upstream direction, and curves radially outward. That is, the portion of arm 46 closest to valve body 32 extends primarily upstream away from the valve body (e.g., extending radially outward only a little, extending not at all radially outward, or even extending radially inward a little), and the arm then curves to extend radially outward. The curvature of arms 46 is described in more detail hereinbelow.

Valve body 32 is defined by a repeating pattern of cells that extends around central longitudinal axis ax1. In the expanded state of each tubular portion, these cells are typically narrower at their upstream and downstream extremities than midway between these extremities. For example, and as shown, the cells may be roughly diamond or astroid in shape. Typically, and as shown, valve body 32 is defined by two stacked, tessellated rows of cells—an upstream row 29a of first-row cells, and a downstream row 29b of second-row cells. Frame 30 is typically made by cutting (e.g., laser-cutting) its basic (i.e., raw) structure from a tube of, for example, Nitinol (followed by re-shaping and heat treating to form its shape-set structure). Although valve body 32 is therefore typically monolithic, because the resulting cellular structure of valve body 32 resembles an open lattice, it may be useful to describe it as defining a plurality of joists 28 that connect at nodes 100 to form the cellular structure.

Typically, and as shown, each arm 46 is attached to and extends from a site 35 that is at the connection between two adjacent cells of upstream row 29a. That is, site 35 is a connection node between first-row cells. The tessellation between rows 29a and 29b is such that site 35 may alternatively be described as the upstream extremity of cells of downstream row 29b. That is, the upstream extremity of each second-row cell is coincident with a respective connection node between first-row cells. Site 35 is therefore a node 100 that connects four joists 28. Upstream end 34 of valve body 32 may be described as defining alternating peaks and troughs, and sites 35 are downstream of the peaks (e.g., at the troughs).

It is hypothesized by the inventors that connecting arm 46 to valve body 32 at site 35 (instead of at upstream end 34) maintains the length of the lumen of the tubular portion, but also advantageously reduces the distance that the tubular portion extends into the ventricle of the subject, and thereby reduces a likelihood of inhibiting blood flow out of the ventricle through the left ventricular outflow tract. It is further hypothesized by the inventors that because each site 35 is a node 100 that connects four joists (whereas each node 100 that is at upstream end 34 connects only two joists), sites 35 are more rigid, and therefore connecting arms 46 to valve body 32 at sites 35 provides greater rigidity to each arm.

Sheeting 23 may comprise one or more individual sheets, which may or may not be connected to each other. The individual sheets may comprise the same or different materials. Typically, sheeting 23 comprises a fabric, e.g., comprising a polyester, such as polyethylene terephthalate. Arms 46 are typically covered with sheeting 23. Typically, and as shown in FIG. 1E, an annular sheet 25 of sheeting 23 is disposed over arms 46, extending between the arms, e.g., so as to reduce a likelihood of paravalvular leakage. For some such applications, excess sheeting 23 is provided between arms 46, so as to facilitate movement of arms 46 independently of each other. Annular sheet 25 typically covers the upstream side of arms 46, but may alternatively or additionally cover the downstream side of the arms.

Alternatively, each arm 46 may be individually covered in a sleeve of sheeting 23, thereby facilitating independent movement of the arms.

Arms 46, and typically the sheeting that covers the arms, define an upstream support portion 40 of implant 20.

Other surfaces of frame assembly 22 may also be covered with sheeting 23. Typically, sheeting 23 covers at least part of valve body 32, e.g., defining a liner 27 that lines an inner surface of the valve body, and thereby defining lumen 38.

Support 40 has an upstream surface, and a downstream surface. Each arm 46 is typically curved such that a downstream surface of support 40 defines an annular concave region 152, and an annular convex region 154 radially outward from the concave region. That is, in region 152 the downstream surface of support 40 (e.g., the downstream surface of each arm 46 thereof) is concave, and in region 154 the downstream surface of the support is convex.

Concave region 152 extends radially between a concave-region inner radius r1 and a concave-region outer radius r2. Convex region 154 extends radially between a convex-region inner radius r3 and a concave-region outer radius r4. It is to be noted that in this context (including the specification and the claims), the term "radius" means a radial distance from axis ax1.

For some applications, and as shown, each arm 46 has a serpentine shape, such that there is no discernable gap between concave region 152 and convex region 154. For such applications, each arm 46 has an inflection point where region 152 transitions into region 154. For such applications, radius r2 and radius r3 are coincident, and collectively define an inflection radius at which the inflection point of each arm lies.

For some applications, radius r1 is the radius of tubular portion 32. For some applications, there is a discernable gap between regions 152 and 154. For example, each arm may be curved in regions 152 and 154, but have a straight portion between these regions.

Although regions 152 and 154 may be locally defined with respect to one or more particular arms 46, these regions typically completely circumscribe axis ax1.

Frame assembly 22 further comprises a plurality of legs 50, each of which, in the expanded state, extends radially outward and in an upstream direction from a respective leg-base 66 to a respective leg-tip 68. Each leg 50 defines a tissue-engaging flange 54, which is typically the most radially outward part of the leg, and includes leg-tip 68. Typically, legs 50 are defined by an outer frame (or "leg frame") 60 that circumscribes and is coupled to valve frame 30.

Frames 30 and 60 define respective coupling elements 31 and 61, which are fixed with respect to each other at coupling points 52. For some applications, frames 30 and 60 are attached to each other only at coupling points 52. Although frames 30 and 60 are attached to each other at coupling points 52, radial forces may provide further coupling between the frames, e.g., frame 30 pressing radially outward against frame 60.

Typically, coupling points 52 are circumferentially aligned with legs 50 (and flanges 54 thereof), but circumferentially offset with respect to arms 46. That is, the coupling points are typically at the same rotational position around axis ax1 as the legs, but are rotationally staggered with respect to the rotational position of the arms.

Coupling points 52 are typically disposed circumferentially around frame assembly 22 on a transverse plane that is orthogonal to axis ax1. That is, coupling points 52 are typically all disposed at the same longitudinal position along axis ax1. Typically, coupling points 52 are disposed longitudinally between upstream end 24 and downstream end 26 of frame assembly 22, but not at either of these ends. Further typically, coupling points 52 are disposed longitudinally between upstream end 34 and downstream end 36 of tubular portion 32, but not at either of these ends. As shown, tubular portion 32 is typically barrel-shaped—i.e., slightly wider in the middle than at either end. For some applications, and as shown, coupling points 52 are disposed slightly downstream of the widest part of tubular portion 32. For example, coupling points 52 may be 0.5-3 mm downstream of the widest part of tubular portion 32. Alternatively or additionally, the longitudinal distance between the widest part of tubular portion 32 and coupling points 52 may be 20-50 percent (e.g., 20-40 percent) of the longitudinal distance between the widest part of the tubular portion and downstream end 36.

Coupling elements 31 are typically defined by (or at least directly attached to) legs 50. Therefore legs 50 are fixedly attached to frame 30 at coupling points 52. Despite the fixed attachment of legs 50 to frame 30, frame 60 comprises a plurality of struts 70 that extend between, and connect, adjacent legs. Struts 70 are typically arranged in one or more rings 72, e.g., a first (e.g., upstream) ring 74 and a second (e.g., downstream) ring 76. For some applications, and as shown, frame 60 comprises exactly two rings 72. Each ring is defined by a pattern of alternating peaks 64 and troughs 62, the peaks being further upstream than the troughs. Each ring is typically coupled to legs 50 at troughs 62—i.e., such that peaks 64 are disposed circumferentially between the legs. Peaks 64 are therefore typically circumferentially aligned with arms 46. That is, peaks 64 are typically at the same rotational position around axis ax1 as arms 46.

The elongate element of frame 60 that defines leg 50 continues in a downstream direction past ring 74 and coupling element 61, and couples ring 74 to ring 76. However, throughout this patent application, leg 50 itself is defined as the free portion of this elongate element that extends from ring 74. Leg-base 66 may be defined as the region of leg 50 that is coupled to the remainder of frame 60 (e.g., to ring 74). Because each leg 50 extends in a generally upstream direction, leg-base 66 may also be defined as the most downstream region of leg 50.

In the expanded state, the leg-tip 68 of each leg is typically disposed radially between radius r3 and radius r4. That is, the leg-tip 68 of each leg is aligned with convex region 154.

Frame 60 is typically cut from a single tube, e.g., of Nitinol. Therefore, the radial thickness of the frame is typically consistent throughout—e.g., it is the wall thickness of the tube from which it was cut. However, the circumferential width of components of frame 60 (i.e., the width of the component measured around the circumference of the frame) may differ. For example, for some applications, a circumferential thickness W2 of legs 50 may be at least three times greater than a circumferential thickness W1 of struts 70. Greater circumferential thickness typically provides the component with greater rigidity.

Valve frame 30 and outer frame 60 are typically each cut from respective metallic tubes, e.g., of Nitinol. This is typically the case for each of the implants described herein. More specifically, for each of the implants described herein:

(1) the valve frame is typically cut from a metallic tube to form a raw valve-frame structure in which the arms and the projections extend axially from the valve body, and the raw valve-frame structure is subsequently shape-set to form a shape-set valve-frame structure in which (i) the valve body is wider than in the raw valve-frame structure, and (ii) the arms extend radially outward from the valve body; and (2) the outer frame is typically cut from a metallic tube to form a raw outer-frame structure in which the legs (including the flanges) extend axially, and the raw outer-frame structure is subsequently shape-set to form a shape-set outer-frame structure in which (i) the rings are wider than in the raw outer-frame structure, and (ii) the flanges extend radially outward from the rings.

Prosthetic leaflets 58 are disposed within lumen 38, and are configured to facilitate one-way liquid flow through the lumen from upstream end 34 to downstream end 36. Leaflets 58 thereby define the orientation of the upstream and downstream ends of valve body 32, and of implant 20 in general.

Typically, implant 20 is biased (e.g., shape-set) to assume its expanded state. For example, frames 30 and 60 may be constructed from a shape-memory metal such as Nitinol or a shape-memory polymer. Transitioning of implant 20 between the respective states is typically controlled by delivery apparatus, such as by constraining the implant in a compressed state within a capsule and/or against a control rod, and selectively releasing portions of the implant to allow them to expand.

Figure 2:
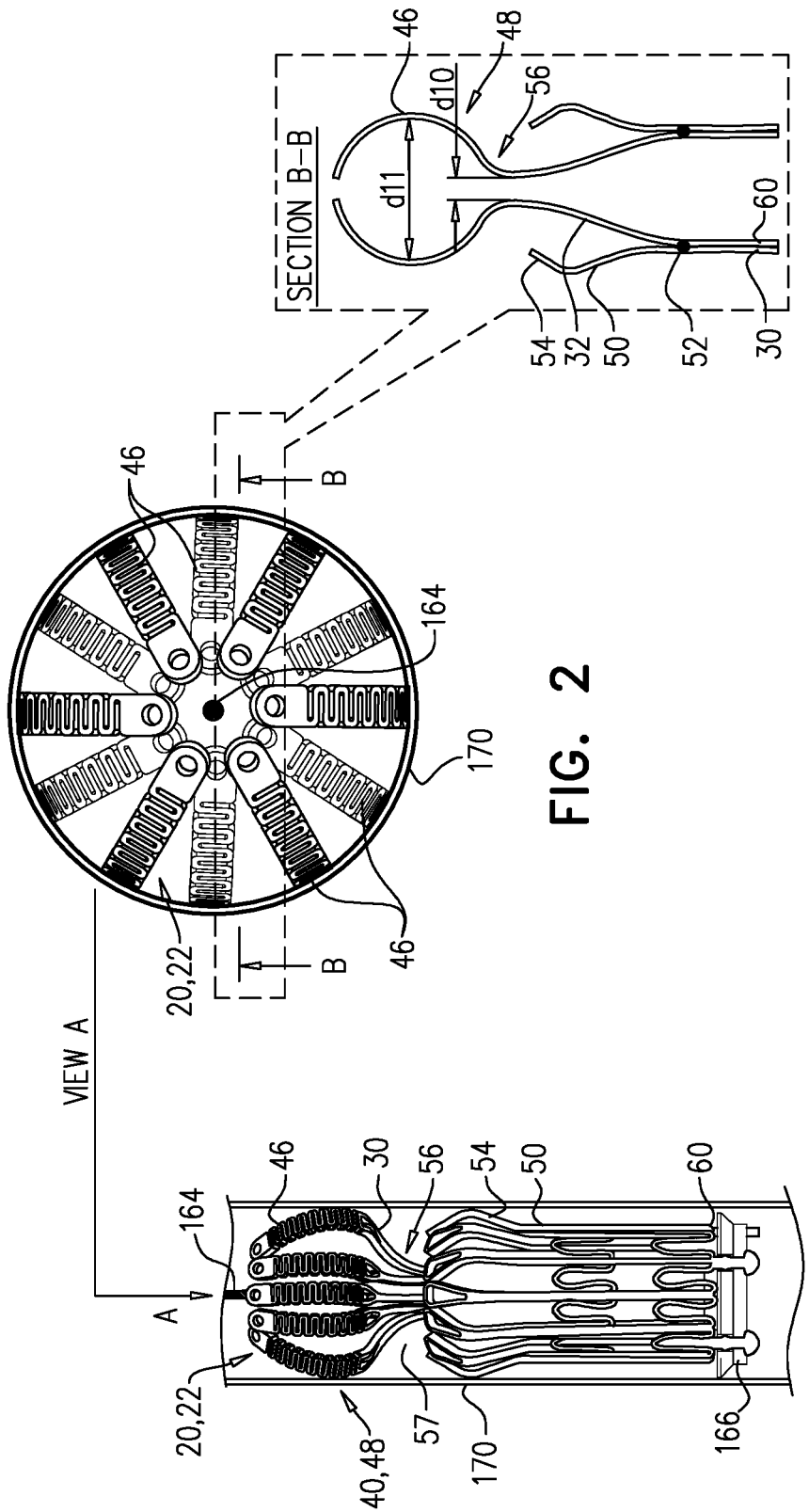

FIG. 2 shows implant 20 in its compressed state, for delivery to the heart of the subject, e.g., within a capsule 170 or delivery tube. Capsule 90 may be a capsule or a catheter. For clarity, only frame assembly 22 of implant 20 is shown. In the compressed state, arms 46 define a ball 48 at an end of valve body 32. It is to be noted that in this context, the term "ball" (including the specification and the claims) means a substantially bulbous element. The ball may be substantially spherical, spheroid, ovoid, or another bulbous shape.

In the compressed state, frame assembly 22 defines a waist 56 (i.e., is waisted) at a longitudinal site between the valve body and the ball. For some applications, and as shown, waist 56 is longitudinally upstream of frame 60, and is therefore primarily defined by valve frame 30. However, for some such applications, the downstream limit of the waist may be defined by the upstream limit of frame 60 (e.g., flanges 54 thereof).

It is to be noted that, typically, the bulbous shape of ball 48 is interrupted at waist 56, i.e., where the frame transitions from the ball to the waist. For some applications, and as shown, valve frame 30 is monolithic (e.g., cut from a single metal tube), and defines both valve body 32 and arms 46. For some applications, and as shown, in the compressed state, the overall shape of valve frame 30 resembles that of an air rifle pellet or a shuttlecock (e.g., see the cross-section in FIG. 2). For some applications, a longitudinal cross-section of frame 30 has an overall shape that resembles a keyhole.

For some applications, at waist 56, frame 30 (and typically frame assembly 22 overall) has a transverse diameter d10 that is less than 5 mm (e.g., 2-4 mm). For some applications, ball 48 has a greatest transverse diameter d11 of 8-12 mm (e.g., 9-11 mm). For some applications, transverse diameter d10 is less than 40 percent (e.g., less than 30 percent, such as 10-30 percent) of transverse diameter d11.

Due to waist 56, while implant 20 is in its compressed state and disposed within capsule 90, the implant and capsule define a toroidal gap 57 therebetween. Toroidal gap 57 circumscribes longitudinal axis ax1 of the implant around waist 56. Therefore, valve body 32 extends in a first longitudinal direction (i.e., in a generally downstream direction) away from gap 57, and arms 46 extend in a second longitudinal direction (i.e., in a generally upstream direction) away from the gap. For applications in which implant 20 is delivered to the native valve transfemorally, valve body 32 is closer to the open end of capsule 90 than is gap 57, and arms 46 (e.g., ball 48) are further from the open end of capsule 90 than is gap 57. For some applications, and as shown, a downstream limit of gap 57 is defined by the tips of flanges 54. For some applications, and as shown, an upstream limit of gap 57 is defined by the downstream side of arms 46.

It is to be noted that, typically, frame 60 is disposed only downstream of toroidal gap 57, but the frame 30 is disposed both upstream and downstream of the toroidal gap.

Reference is again made to FIG. 1E. For some applications, implant 20 comprises a polytetrafluoroethylene (e.g., Teflon) ring 78 attached to downstream end 26. Ring 78 circumscribes lumen 38 at downstream end 36 of valve body 32, and typically at downstream end 26 of implant 20. Therefore ring 78 serves as a downstream lip of lumen 38. Typically, ring 78 is attached (e.g., stitched) to both frame 30 and frame 60. For example, ring 78 may be attached to frame 60 at troughs 62. For some applications, ring 78 is stitched to downstream end 36 of valve body 32 by stiches 99 that wrap around the ring (i.e., through the opening of the ring and around the outside of the ring) but do not pierce the ring (i.e., the material of the ring).

Typically, ring 78 covers downstream end 26 of the implant (e.g., covers the frames at the downstream end). It is hypothesized by the inventors that ring 78 advantageously protects tissue (e.g., native leaflets and/or chordae tendineae) from becoming damaged by downstream end 26 of implant 20. There is therefore provided, in accordance with some applications of the invention, apparatus comprising:

- a valve body, having an upstream end and a downstream end, shaped to define a lumen from the upstream end to the downstream end, the lumen defining a longitudinal axis of the prosthetic valve, and the downstream end of the valve body having;
- a fabric liner, lining the lumen;
- a valve member, disposed within the lumen of the valve body; and
- a polytetrafluoroethylene ring coupled to the downstream end of the valve body such that the ring circumscribes the lumen at the downstream end of the valve body.

Reference is made to FIGS. 3A-F, which are schematic illustrations showing the implantation of implant 20 at a native valve 10 of a heart 4 of a subject, in accordance with some applications of the invention. Valve 10 is shown as a mitral valve of the subject, disposed between a left atrium 6 and a left ventricle 8 of the subject. However, implant 20 may be implanted at another heart valve of the subject, mutatis mutandis. Similarly, although FIGS. 3A-F show implant 20 being delivered transseptally via a sheath 88, the implant may alternatively be delivered by any other suitable route, such as transatrially, or transapically.

Figure 3A:
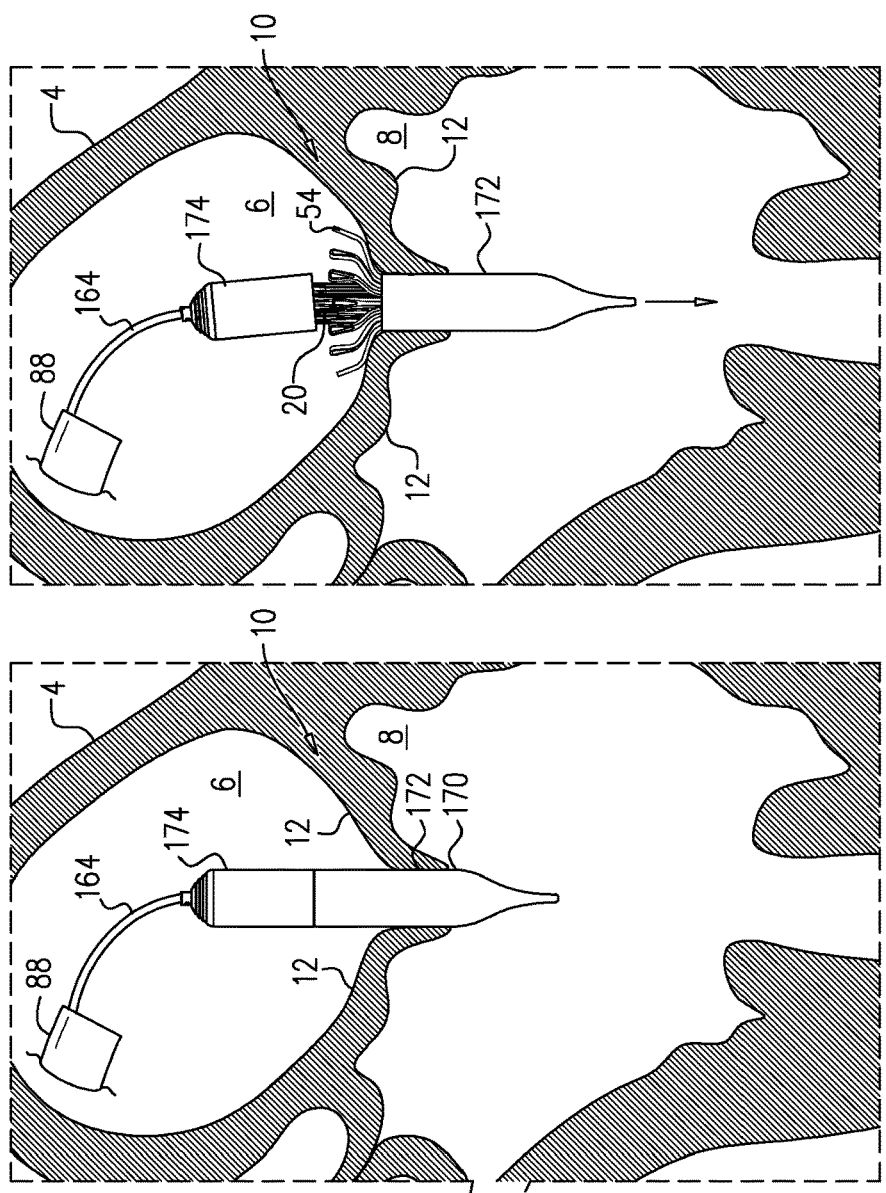

Implant 20 is delivered, in its compressed state, to native valve 10 using a delivery tool 160 that is operable from outside the subject (FIG. 3A). Tool 160 typically comprises an extracorporeal controller 162 (e.g., comprising a handle) at a proximal end of the tool, and a shaft 164 extending from the controller to a distal portion of the tool. At the distal portion of tool 160, the tool typically comprises a capsule 170 comprising one or more capsule portions 172, 174 (described below), and a mount 166. Mount 166 is coupled (typically fixed) to shaft 164. Controller 162 is operable to control deployment of implant 20 by transitioning the tool between a delivery state (FIG. 3A), an intermediate state (FIG. 3E), and an open state (FIG. 3F). Typically, implant 20 is delivered within capsule 170 of tool 160 in its delivery state, the capsule retaining the implant in the compressed state. Implant 20 typically comprises one or more appendages 80 at downstream end 26, each appendage typically shaped to define a catch or other bulbous element at the end of the appendage, and to engage mount 166, e.g., by becoming disposed within notches in the mount. Appendages 80 are typically defined by valve frame 30, but may alternatively be defined by outer frame 60. Capsule 170 retains appendages 80 engaged with mount 166 by retaining implant 20 (especially downstream end 26 thereof) in its compressed state. A transseptal approach, such as a transfemoral approach, is shown. At this stage, frame assembly 22 of implant 20 is as shown in FIG. 2.

Figure 3B:
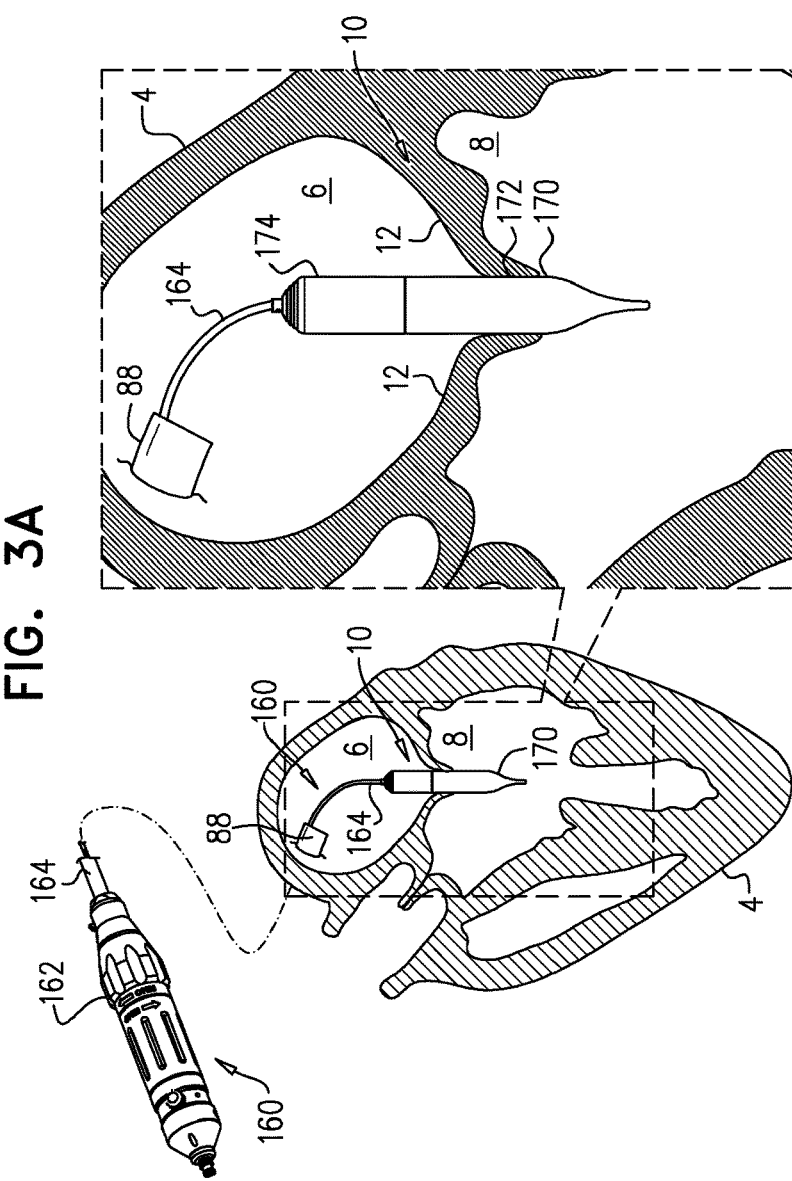

Subsequently, flanges 54 are deployed—i.e., are allowed to protrude radially outward, e.g., by releasing them from capsule 170 (FIG. 3B). For example, and as shown, capsule 170 may comprise a distal capsule-portion 172 and a proximal capsule-portion 174, and the distal capsule-portion may be moved distally with respect to implant 20, so as to expose flanges 54 while continuing to restrain upstream end 24 and downstream end 26 of implant 20. In FIG. 3B, upstream support portion 40 (e.g., arms 46) is disposed within capsule-portion 174, and downstream end 36 of tubular portion 32 is disposed within capsule-portion 172.

Typically, and as shown in FIGS. 3A-B, tool 160 is positioned such that when flanges 54 are deployed, they are deployed within atrium 6 and/or between leaflets 12 of the subject. Subsequently, the tool is moved downstream (distally, for a transseptal approach) until the leaflets are observed to coapt upstream of flanges 54 (FIG. 3C). It is hypothesized by the inventors that this reduces how far into ventricle 8 the flanges become disposed, and therefore reduces the distance that the deployed flanges must be moved in an upstream direction in order to subsequently engage the leaflets, and therefore reduces the likelihood of inadvertently or prematurely ensnaring tissue such as chordae tendineae. This is described in more detail, mutatis mutandis, in WO 2016/125160 to Hariton et al., filed Feb. 3, 2016, which is incorporated herein by reference.

Alternatively, flanges 54 may be initially deployed within ventricle 8.

Subsequently, implant 20 is moved upstream, such that flanges 54 engage leaflets 12 of valve 10 (FIG. 3D).

Subsequently, delivery tool 160 is transitioned into its intermediate state, thereby allowing implant 20 to assume a partially-expanded state in which upstream support portion 40 is expanded, e.g., by releasing the upstream support portion from capsule 170 (FIG. 3E). For example, and as shown, proximal capsule-portion 174 may be moved proximally with respect to mount 166 and/or implant 20, so as to expose upstream support portion 40 (e.g., arms 46). Typically, in this state, upstream support portion 40 has expanded to have a diameter that is at least 80 percent (e.g., at least 90 percent, e.g., at least 95 percent) of its diameter in the expanded state of implant 20 (e.g., the diameter after implantation is complete), while downstream end 26 of the implant remains compressed. For some applications, in the partially-expanded state, upstream support portion 40 has expanded to its fully-expanded diameter. That is, downstream end 36 of tubular portion 32 remaining disposed within capsule-portion 172 typically does not inhibit, by more than 20 percent, if at all, the expansion of upstream support portion 40. However, in the partially-expanded state of implant 20, legs 50 are partially inhibited from expanding, such that each leg-tip 68 is radially aligned with concave region 152. That is, each leg-tip 68 is disposed radially between concave-region inner radius r1 and concave-region outer radius r2.

In the intermediate state, leaflets 12 of native valve 10 are sandwiched between upstream support portion 40 (e.g., annular sheet 25 thereof) and legs 50 (e.g., flanges 54 thereof). It is to be noted that appendages 80 remain engaged with mount 166.

Subsequently, delivery tool 160 is transitioned into its open state, thereby allowing implant 20 to expand toward its expanded state (i.e., such that tubular portion 32 widens to its fully-expanded state) (FIG. 3F). For example, capsule-portion 172 may be moved distally with respect to mount 166 and/or implant 20. The resulting expansion of downstream end 26 of implant 20 disengages appendages 80, and thereby implant 20 as a whole, from mount 166. Appendages 80 are not visible in FIG. 3F (or FIG. 3C) because they are obscured by ring 78.

In the expanded state of implant 20, each leg-tip 68 is radially aligned with convex region 154. That is, each leg-tip 68 is disposed radially between convex-region inner radius r3 and convex-region outer radius r4. This is also illustrated in FIG. 1C.

Tool 160 (e.g., capsule-portion 172 thereof) may then be withdrawn via lumen 38 of implant 20, and removed from the body of the subject.

Figure 4:
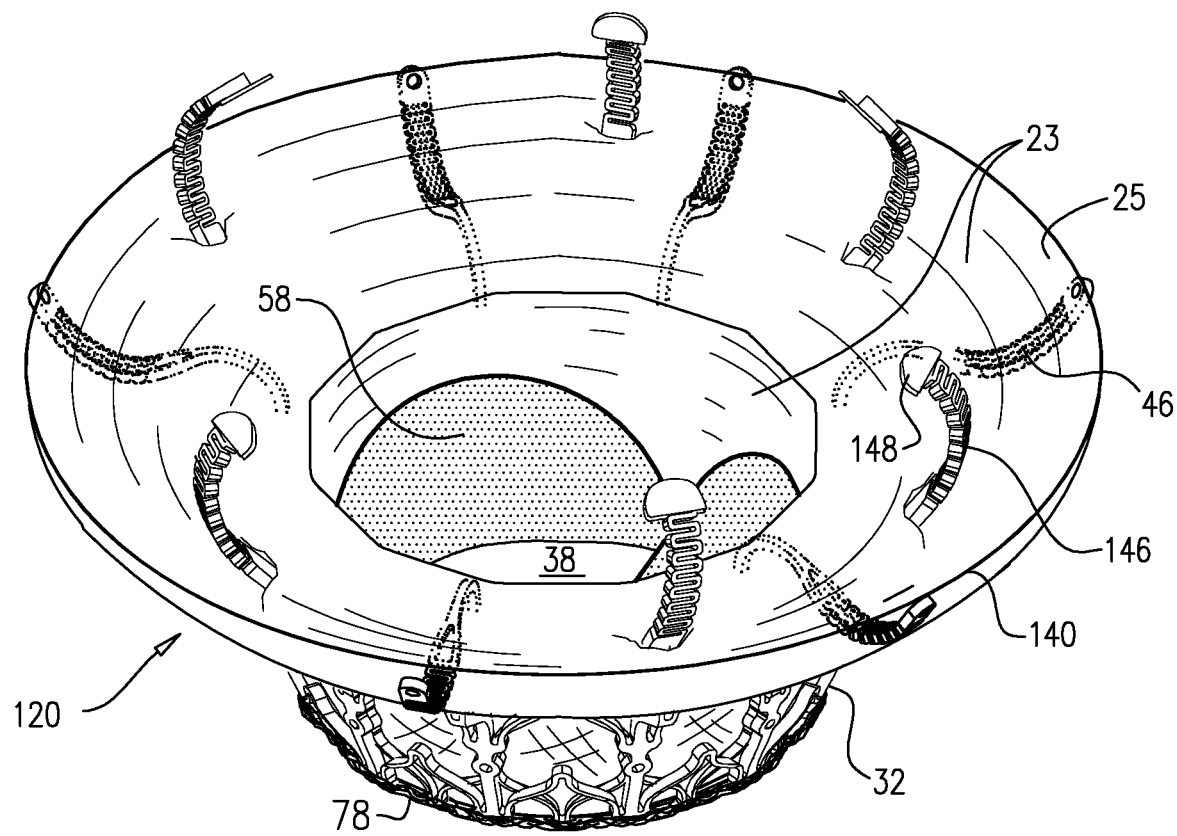
FIGS. 4, 5A-C, and 6 are schematic illustration of implants and their frames, in accordance with some applications of the invention.
Figure 5A:
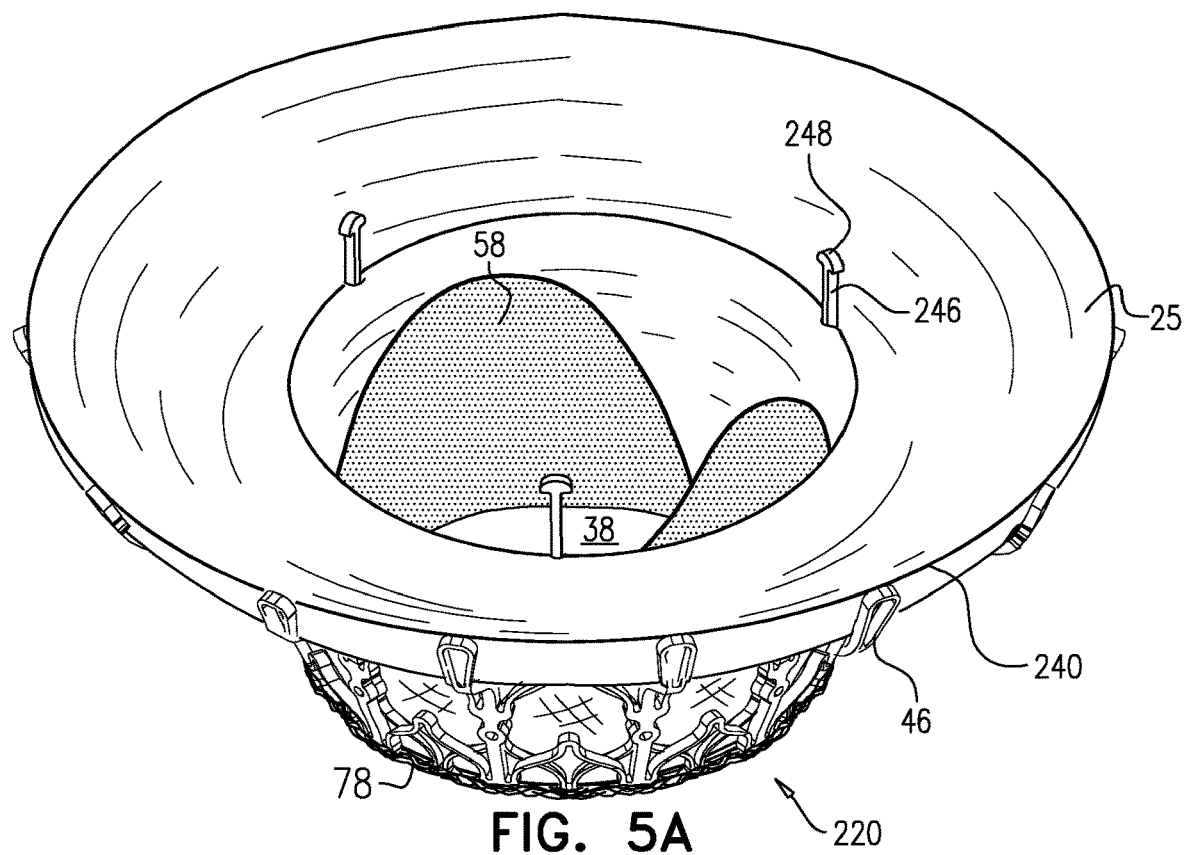
Figure 5B:
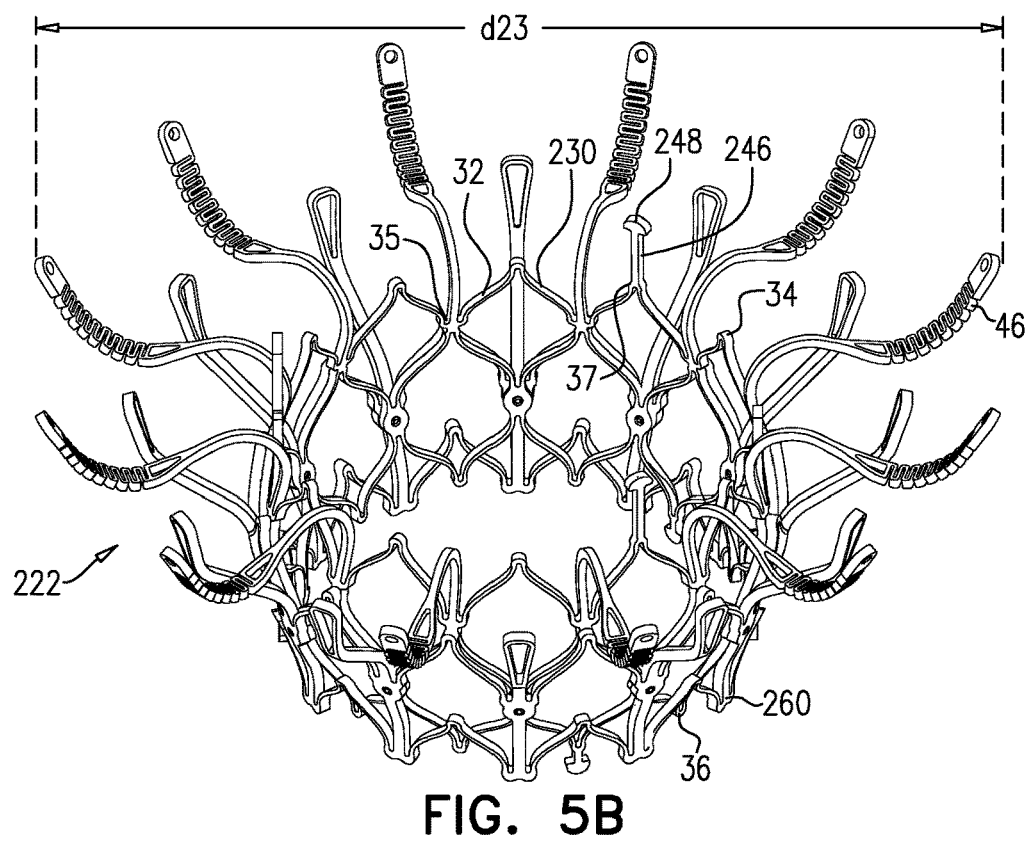
Figure 5C:
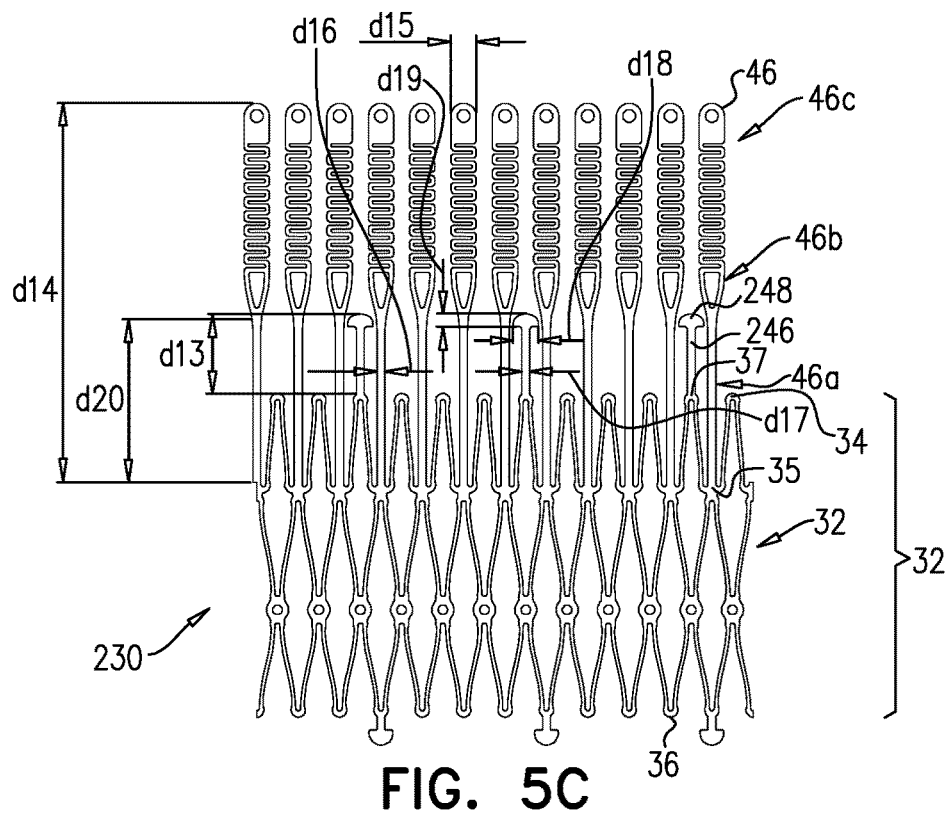

Reference is made to FIGS. 4, and 5A-C, which are schematic illustrations of implants, in accordance with some applications of the invention. FIG. 4 shows an implant 120. FIG. 5A shows an implant 220, FIG. 5B shows a frame assembly 222 of implant 220 after shape-setting, and FIG. 5C shows a valve frame 230 of frame assembly 222 prior to shape-setting (i.e., the shape-set valve-frame structure).

Implants 120 and 220 are typically the same as implant 20, described hereinabove, except where noted. Sheeting 23 forms annular sheet 25 that is disposed over and typically stitched to arms 46. Implant 120 thereby comprises valve body 32 (e.g., as described hereinabove), and an upstream support portion 140 that itself comprises arms 46 and annular sheet 25. Similarly, implant 220 comprises valve body 32 and an upstream support portion 240 that itself comprises arms 46 and annular sheet 25.

Implants 120 and 220 each further comprises a respective plurality of elongate projections 146 or 246. Whereas arms 46 are covered by sheeting 23, the projections extend in an upstream direction through sheeting 23. For some applications, and as shown for projections 146, the projections extend through annular sheet 25. For some applications, and as shown for projections 246, the projections extend between annular sheet 25, and a portion of sheeting 23 that lines valve body 32 (e.g., at a seam where these two portions of sheeting 23 are joined). The projections and arms 46 are both configured to be positioned in atrium 6 of the heart. For some applications, and as shown for projections 146, the projections extend through annular sheet 25.

It is to be noted that projection 146 and 246 are distinct from appendages 80, which are disposed at the other end of the valve body.

Each projection terminates in a nub 148 or 248 that facilitates snaring of the projection using a transcatheter snare, lasso, or similar tool. It is to be understood that the shapes shown for the nubs are merely examples, and that the scope of the invention includes any suitably shaped nub. It is hypothesized by the inventors that the projections facilitate repositioning and/or retrieval of the implant during and/or after implantation, using a snare, lasso, or similar tool. The projections are typically positioned and/or shaped such that nubs 148 or 248 are not in contact with annular sheet 25 or atrial tissue (e.g., are disposed at least 5 mm away (e.g., 5-25 mm away) from annular sheet 25 or atrial tissue). For some applications, and as shown for projections 146 of implant 120, the projections curve outwards and then inwards toward the central longitudinal axis of the implant (i.e., are shaped to be concave toward the axis). For some applications, and as shown for projections 246 of implant 220, the projections do not extend radially outward from the valve body. Projections 246 typically extend axially in an upstream direction away from the valve body (i.e., generally parallel to axis ax1, i.e., within 10 degrees of axis ax1).

Regarding implant 120 (FIG. 4), projections 146 extend from sites 35 in a similar way to arms 46. Projections 146 may be structurally similar to arms 46, and may even be identically cut when frame 30 is initially cut from the original metal tube (i.e., in the raw valve-frame structure). However, projections 146 have a different curvature to arms 46 (e.g., they may be bent differently post-cutting), and are curved such that they extend through annular sheet 25. Whereas at least some of arms 46 typically reach and press against the atrial wall, projections 146 are typically shaped such that nubs 148 are not in contact with the atrial wall. Typically, each projection 146 replaces an arm 46, such that the cumulative sum of arms and projections is twelve. FIG. 4 shows an embodiment comprising six arms 46 and six projections 146, but the scope of the invention includes other ratios, such as nine arms 46 and three projections 146.

FIG. 5A shows implant 220, comprising a frame assembly 222, leaflets 58, and sheeting 23. FIG. 5B shows frame assembly 222 alone, the frame assembly comprising (i) a valve frame 230 that defines valve body 32, and (ii) an outer frame 260. FIG. 5C shows the basic structure of valve frame 230, as it is initially cut from a tube (typically a metallic tube, such as a Nitinol tube), e.g., before the frame is shape-set into the shape shown in FIG. 5B. Although this basic structure is tubular, FIG. 5C depicts the structure two-dimensionally, as though the cut-out structure were cut longitudinally, and unrolled to become flat.

Except where noted, frame assembly 222, valve frame 230, and outer frame 260 are typically identical to frame assembly 22, valve frame 30, and outer frame 60, mutatis mutandis. For some applications, implant 220 is identical to implant 20 except for projections 246.

Figure 11A:
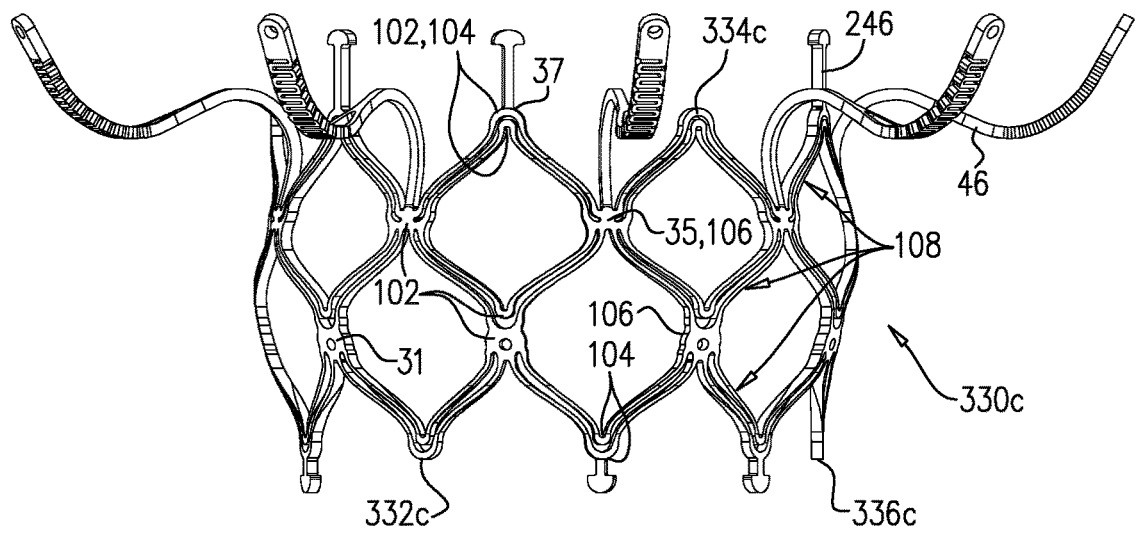
FIGS. 11A-B are schematic illustrations of an inner frame, and an implant comprising the inner frame, in accordance with some applications of the invention.
Figure 11B:
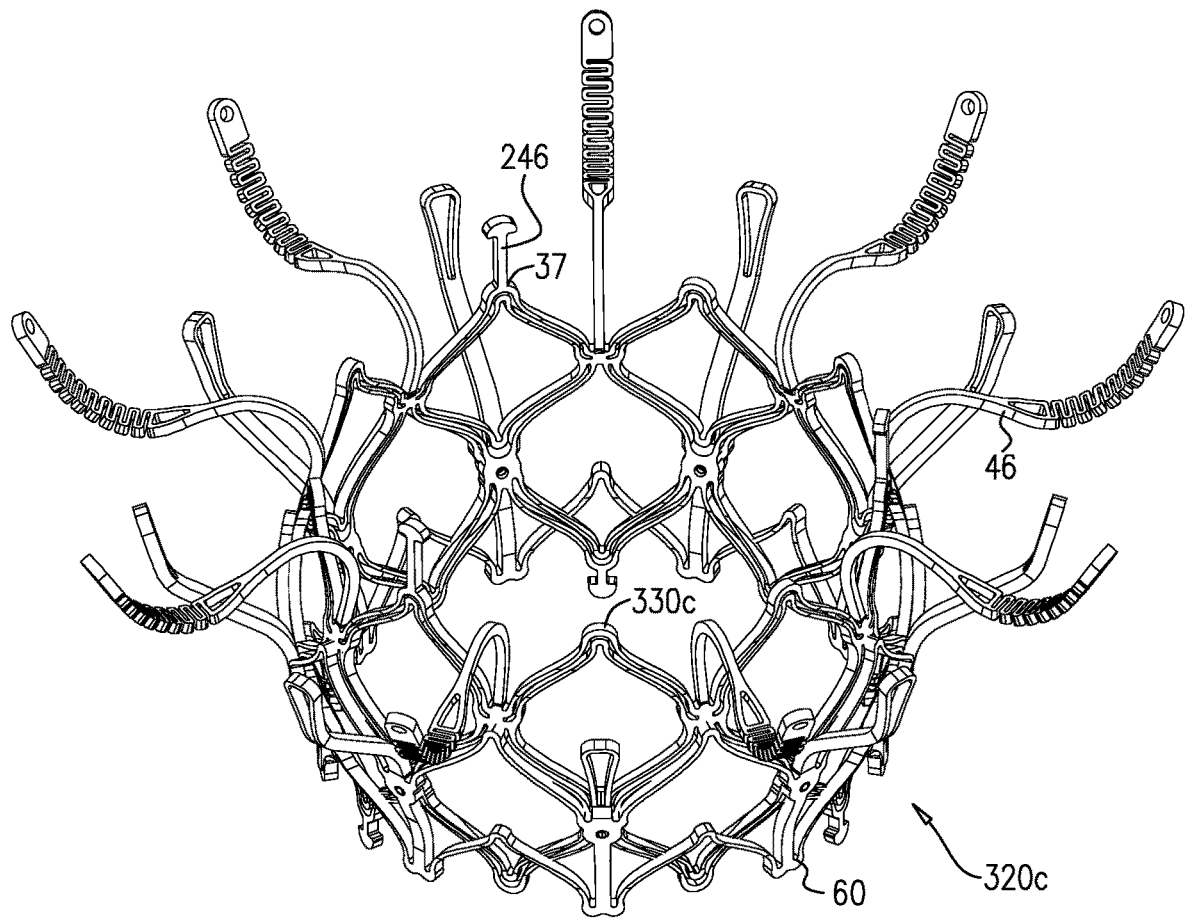

In contrast to projections 146 of implant 120, each projection 246 of implant 220 extends from a respective site 37 that is at the upstream extremity (i.e., peak) of a respective first-row cell of upstream row 29a of valve body 32 (i.e., from upstream end 34 of the valve body). Projections 246 thereby alternate with, rather than replace, arms 46. Therefore, it is possible for implant 220 to comprise projections 246 in addition to twelve arms 46. Implant 220 may comprise an equal number of projections 246 and arms 46, but typically, the implant comprises fewer projections than arms. For example, implant 220 may comprise half as many, or fewer, projections 246 than arms 46—e.g., a third as many, or a quarter as many projections as arms. Projections 246 and arms 46 are typically evenly distributed circumferentially, and therefore typically at least two arms (e.g., at least three arms, such as at least four arms) are disposed circumferentially between each projection and each of its circumferentially-neighboring projections. FIGS. 5A-C show implant 220 comprising three projections 246 and twelve arms 46, with four arms disposed circumferentially between each projection and each of its circumferentially-neighboring projections. FIGS. 11A-B, described hereinbelow, show an implant in which three arms are disposed circumferentially between each projection and each of its circumferentially-neighboring projections.

Each projection 246 has a projection-length d13, measured from the upstream extremity of the respective first-row cell (i.e., from site 37). Each of the arms has an arm-length d14, measured from the upstream extremity of the respective second-row cell (i.e., site 35). Arm-length d14 is greater than projection-length d13 (e.g., 2-20 times greater, e.g., 4-20 times greater, such as 4-10 times greater). For some applications, arm-length d14 is 20-28 mm, such as 22-26 mm (e.g., 22-23 mm, 23.5-24.5 mm, or 25-26 mm). For some applications, projection-length d13 is 2-10 mm (e.g., 3-8 mm, e.g., 4-6 mm, such as about 5 mm).

Typically, each arm 46 (i) has a narrow portion 46a that is attached to, and extends from, the upstream extremity of the respective second-row cell, and (ii) at a widening zone 46b, widens into a wide portion 46c that extends from the narrow portion, and is wider than the narrow portion. Narrow portion 46a has a narrow-portion length d20 that is typically at least 30 percent of arm-length d14 (e.g., at least 40 percent, such as 40-80 percent, such as 40-60 percent). Wide portion 46c has a wide-portion length that is at least 30 percent of arm-length d14 (e.g., at least 40 percent, such as 40-80 percent, such as 40-60 percent).

Wide portion 46c has a width d15 that is typically 1.5-6 times greater (e.g., 2-4 times greater, such as 2.5-3.5 times greater) than a width d16 of narrow portion 46a. For some applications width d15 is 1-2 mm (e.g., 1.4-1.8 mm, such as 1.6 mm). Width d16 is typically 0.2-0.8 mm (e.g., 0.4-0.6 mm, such as 0.5 mm). It is to be noted that, although individual parts of arm 46 within portion 46c may be narrower than within portion 46a, these individual parts form a back-and-forth pattern that results in wide portion 46c being, overall, wider than narrow portion 46a. Typically, wide portion 46c is more flexible, in at least one plane, than narrow portion 46a. Therefore, wide portion 46c is also a flexible portion of arm 46.

Each projection 246 has a width d17 that is typically 0.2-0.8 mm (e.g., 0.4-0 6 mm, such as 0.5 mm). Each nub has a nub-width d18 that is typically 1-2 mm (e.g., 1.4-1 8 mm, such as 1.6 mm), and a nub-length d19 that is typically 0.5-1 mm (e.g., 0.7-0.9 mm, such as 0.8 mm). Wide portion 46c is typically at least 3 times (e.g., at least 10 times) longer than nub-length d19.

As described hereinabove, the valve frame is typically monolithic, cut from a single tube. Typically, and as shown in FIG. 5C, while valve frame 230 is in its raw valve-frame structure (e.g., described hereinabove with reference to FIGS. 1A-E, mutatis mutandis), nubs 248 are disposed between arms 46. As shown in FIG. 5C, arms 46 and projections 246 may be dimensioned such that, while valve frame 230 is in its raw valve-frame structure, nubs 248 are disposed between narrow portions 46a of arms 46. That is, nubs 248 may be disposed axially closer than wide portion 46c to valve body 32. Thereby, arms 46 and projections 246 efficiently fit adjacently to each other within a single cutout from tube of a particular diameter. Narrow-portion length d20 is typically greater than projection-length d13 (e.g., at least 1.5 times greater, such as 1.5-3 times greater).

Figure 6:
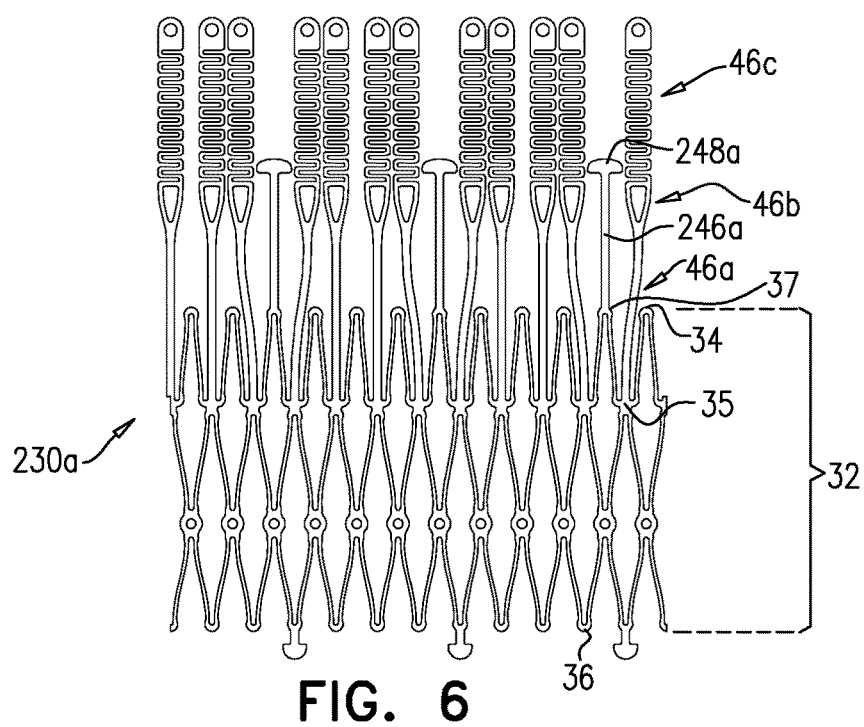

Reference is now made to FIG. 6, which shows the basic structure of a variant 230a of valve frame 230, in accordance with some applications of the invention. FIG. 6 shows variant 230a as it is initially cut from a tube (typically a metallic tube, such as a Nitinol tube), e.g., before the frame is shape-set. FIG. 6 shows a two-dimensional view, as though the cut-out structure were cut longitudinally, and unrolled to become flat. Similarly to with frame 230 (FIG. 5C), nubs 248 of variant 230a are disposed between arms 46. However, projections 246a of variant 230a are longer than projections 246 of frame 230, and nubs 248a are therefore disposed between wide portions 46c of arms 46. In order to accommodate this, in frame 230a, at least the arms 46 that are adjacent to nubs 248a are deflected circumferentially (which is represented two-dimensionally as being laterally deflected) compared to their positions in frame 230, and are typically unevenly spaced. During subsequent shape setting, arms 46 are typically circumferentially displaced, e.g., such that they are evenly spaced. Variant 230a may be used in place of any other valve frame described herein, mutatis mutandis. Similarly, variant 230a may be used in combination with other technologies described herein, mutatis mutandis.

Reference is made to FIG. 7, which is a schematic illustration of an outer frame 60a, in accordance with some applications of the invention. Outer frame 60a is typically identical to outer frame 60 except that peaks 64a of frame 60a have a larger radius of curvature than do peaks 64 of frame 60. Outer frame 60a may be used in place of any other outer frame described herein, mutatis mutandis. Similarly, frame 60a may be used in combination with other technologies described herein, mutatis mutandis.

Reference is made to FIG. 8, which is a schematic illustration of a frame assembly 22b, in accordance with some applications of the invention. Frame assembly 22b comprises a valve frame 30b and an outer frame 60b. Except where noted, frame assembly 22b, valve frame 30b, and outer frame 60b are as described for frame assembly 22, valve frame 30, and outer frame 60, respectively.

Outer frame 60b comprises (or defines) (1) a first (e.g., upstream) ring 74b defined by a pattern of alternating first-ring peaks and first-ring troughs, (2) a second (e.g., downstream) ring 76b defined by a pattern of alternating second-ring peaks and second-ring troughs, and a plurality of legs 50, each of the legs coupled to the first ring and the second ring, and extending radially outward.

Valve frame 30b comprises a tubular portion (e.g., a tubular frame) that has a cellular structure defined by a plurality of metallic elements with spaces therebetween a e.g., as described for valve frame 30, mutatis mutandis.

The cellular structure of the valve frames described herein may also be viewed as defining rings of alternating peaks and troughs, the rings circumscribing the longitudinal axis of the implant. Whereas the waveform (i.e., the peak-trough waveform) of the rings of the outer frame are in phase with each other, the phase of the waveform of the rings of the valve frame typically alternate with respect to each other. That is, for the valve frame, the waveform of one ring is out of phase (e.g., is in antiphase) with that of its axially-adjacent rings. For example, and with reference to FIG. 1B, valve frame 30 defines a first (e.g., upstream) ring 182, a second (e.g., middle) ring 184, and a third (e.g., downstream) ring 186, and ring 184 is in antiphase with rings 182 and 184. Valve frame 30b similarly defines a first (e.g., upstream) ring 182b, a second (e.g., middle) ring 184b, and a third (e.g., downstream) ring 186b, and ring 184b is in antiphase with rings 182b and 184b.

Typically, and as shown for each of the implants described herein, when the frame assembly is assembled, (1) the waveform of one of outer frame rings is in-phase with the waveform of the inner frame ring with which it is axially aligned, and (2) the waveform of one of outer frame rings is out of phase (e.g., is in antiphase) with the waveform of the inner frame ring with which it is axially aligned. For example, and with reference to FIG. 1C, ring 74 is in-phase with the ring of the inner frame with which it is axially aligned (ring 184), whereas ring 76 is in antiphase with the ring of the inner frame with which it is axially aligned (ring 186). Similarly, for frame assembly 22b, ring 74b is in-phase with the ring of the inner frame with which it is axially aligned (ring 184b), whereas ring 76b is in antiphase with the ring of the inner frame with which it is axially aligned (ring 186b).

Because ring 76b is in antiphase with ring 186b, the peaks of ring 76b are not disposed directly radially outward from respective parts of frame 30b, and therefore are not in contact with frame 30b. However, despite ring 74b being in phase with ring 184b, and the peaks of ring 74b being disposed directly radially outward from respective parts of frame 30b, the peaks of ring 74b are also not in contact with frame 30b. That is, frame assembly 22 defines a radial gap 188 between frames 30 and 60 at the peaks of ring 74b. Typically, therefore, none of the peaks of the rings of frame 60b is in contact with inner frame 30b. In contrast, for frame assembly 22, although the peaks of ring 76 are not in contact with frame 30, the peaks of ring 74 typically are in contact with frame 30.

The features of frame assembly 22b may be used in combination with other implants described herein. For example, other frame assemblies described herein may be shaped to define gap 188, mutatis mutandis.

Reference is made to FIGS. 9A-B, which are schematic illustrations of an inner frame 330a, and an implant 320a comprising inner frame 330a, in accordance with some applications of the invention. Inner frame 330a may be used in place of other inner frames of implants described herein, mutatis mutandis. Similarly, frame 330a may be used in combination with other technologies described herein, mutatis mutandis. Inner frame 330a comprises a valve body (which is a generally tubular portion) 332a that has an upstream end 334a and a downstream end 336a, and is shaped to define a lumen through the valve body from its upstream end to its downstream end. Valve frame 330a further comprises a plurality of arms 46, each of which, in the expanded state, extends radially outward from valve body 332a.

Valve body 332a has a cellular structure defined by a plurality of joists 28 connected at a plurality of nodes 102, the joists and nodes delimiting cells of the cellular structure. Except where noted, inner frame 330a is generally the same as inner frame 230 (or inner frame 30), mutatis mutandis, and valve body 332a is generally the same as valve body 32, mutatis mutandis. Compared to valve body 32, valve body 332a comprises additional joists 28, which are hypothesized by the inventors to increase strength and rigidity. In particular, the additional joists are hypothesized by the inventors to increase the resistance of the valve body to compression toward axis ax1, including resistance to circumferential compression (e.g., compression that would otherwise reduce the diameter of the valve body, but that would retain the valve body in a generally cylindrical shape) and localized compression (e.g., compression that would otherwise reduce the diameter of the valve body at only certain locations, causing the valve body to become more oval in transverse cross-section).

Referring back to FIGS. 1A-B, the cellular structure of valve body 32 is such that its nodes 100 typically connect 2-4 of its joists. For example, a node 100a connects two joists, and a node 100b connects four joists. (In this context, neither arms 46 nor projections 246 are joists of the valve body's cellular structure, and so sites 35 and 34 are also nodes that connect 2-4 joists.) In contrast, the cellular structure of valve body 332a is such that some of its nodes 102 are minor nodes 104, and some are major nodes 106. Minor nodes 104 connect 2-4 joists, whereas major nodes 106 connect 6-8 joists. Typically, and as shown, major nodes 106 connect 6 joists (again, excluding arms 46, which are not joists of the valve body's cellular structure). Typically, and as shown, minor nodes 104 connect 2 joists. Therefore, for some applications, none of the nodes 102 of the cellular structure of valve body 332a connects 4 joists.

Similarly to valve body 32 of frame 30, the cells of the cellular structure of valve body 332a comprise a first circumferential row 109a of cells, and a second circumferential row 109b of cells. That is, row 109a is a row of first-row cells, and row 109b is a row of second-row cells. Each of the cells of row 109a is connected to each of its circumferentially-adjacent first-row cells at a respective major node 106. Typically, and as shown, each of the cells of row 109a is longitudinally delimited by two minor nodes 104 (i.e., the upstream end and the downstream end of each cell is at a respective minor node). It is to be noted that, typically, each of the cells of row 109a is not connected to another cell at these minor nodes 104 (i.e., the minor nodes that longitudinally delimit the first-row cell).

Each of the cells of row 109b is connected to each of its circumferentially-adjacent second-row cells at a respective major node 106. Typically, and as shown, each of the cells of row 109b is longitudinally delimited by at least one major node 106 (e.g., is delimited by one major node at an upstream end of the cell). Typically, and as shown, each of the cells of row 109b is also longitudinally delimited by a minor node 104 (e.g., at a downstream end of the cell). For some applications, and as shown, each of the major nodes 106 at which circumferentially-adjacent first-row cells are connected is also the major node that longitudinally-delimits a respective second-row cell (e.g., at the upstream end of the second-row cell). In the example shown, that common major node 106 is also site 35, at which arms 46 are attached to the valve body.

The cells of the cellular structure of valve body 332a are typically delimited by exactly four nodes 102.

Frame 330a defines coupling elements 31, which are fixed to coupling elements 61 of frame 60 at coupling points, as described hereinabove for frame assembly 22, mutatis mutandis. For some applications, and as shown, coupling elements 31 are defined by respective major nodes 106. Therefore, for some applications, a frame assembly comprises (i) inner frame 330a that defines valve body 332a, and (ii) an outer frame (e.g., frame 60) that circumscribes the valve body, and is coupled to the inner frame by being fixed to major nodes of the valve body. For such applications, coupling elements 31 are typically defined by the major nodes at which circumferentially-adjacent second-row cells are connected.

For some applications, and as shown, valve body 332a is defined by exactly two stacked, tessellated rows 109 of cells. That is, typically, first row 109a is the most upstream row, second row 108b is the most downstream row, and these two rows are tessellated with each other. Therefore, for some applications, all the cells of the cellular structure of valve body 332a are either first-row cells or second-row cells.

Valve body 332a may be described as comprising pairs 108 of joists 28 that run generally parallel to each other. In the expanded state of the valve body (i.e., the state shown in FIG. 7) the joists 28 of each pair 108 are disposed 0.1-1 mm (e.g., 0.25-0.9 mm, such as 0.25-0.65 mm) from each other. Although the joists 28 of each pair 108 run generally parallel to each other, they typically only share one node 102 in common. That shared common node is typically a major node 106. That is, at a first end of each pair 108, both joists 28 are typically connected to each other at a major node. In some cases, at a second end of each pair 108, one of the joists connects to another major node 106, but the other joist connects to a minor node 104 that is disposed a distance d12 away from the major node at the second end of the pair. In other cases, at the second end of each pair 108, one of the joists connects to a first minor node, and the other joist connects to another minor node that is disposed a distance d12 away from the first minor node. Distance d12 is typically 0.1-1 mm (e.g., 0.25-0.9 mm, such as 0.25-0.65 mm).

For some applications, and as shown, the arrangement of joists 28 in pairs 108 results in the joists that delimit the cells of first row 109a not delimiting the cells of second row 109b. That is, for some applications, no individual joist 28 delimits both a first-row cell and a second-row cell.

Another aspect of valve body 332a is as follows: Major nodes 106 are typically arranged in major-node rows, each major-node row circumscribing longitudinal axis ax1 at a respective major-node-row longitudinal site, and minor nodes 104 are typically arranged in minor-node rows, each minor-node row circumscribing the longitudinal axis at a respective minor-node-row longitudinal site. Along at least part of axis ax1, the minor-node-row longitudinal sites alternate with the major-node-row longitudinal sites. For some applications, along at least this part of axis ax1, at least 3 minor-node-row longitudinal sites alternate with at least 2 major-node-row longitudinal sites, e.g., in the order minor-major-minor-major-minor, as shown.

Figure 10A:
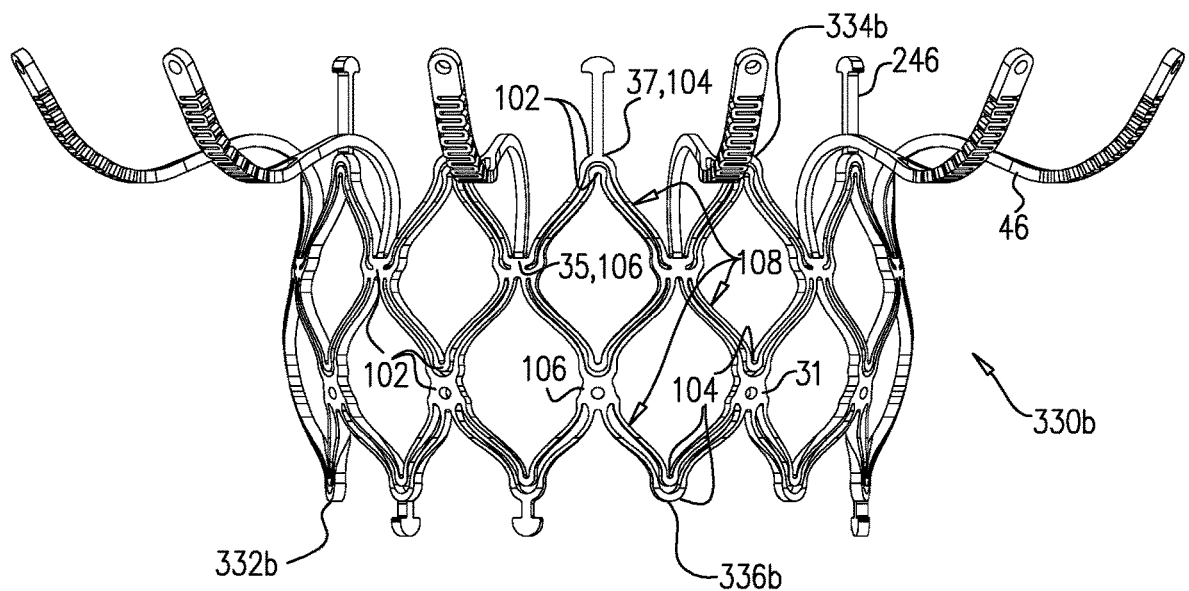
FIGS. 10A-B are schematic illustrations of an inner frame, and an implant comprising the inner frame, in accordance with some applications of the invention.
Figure 10B:
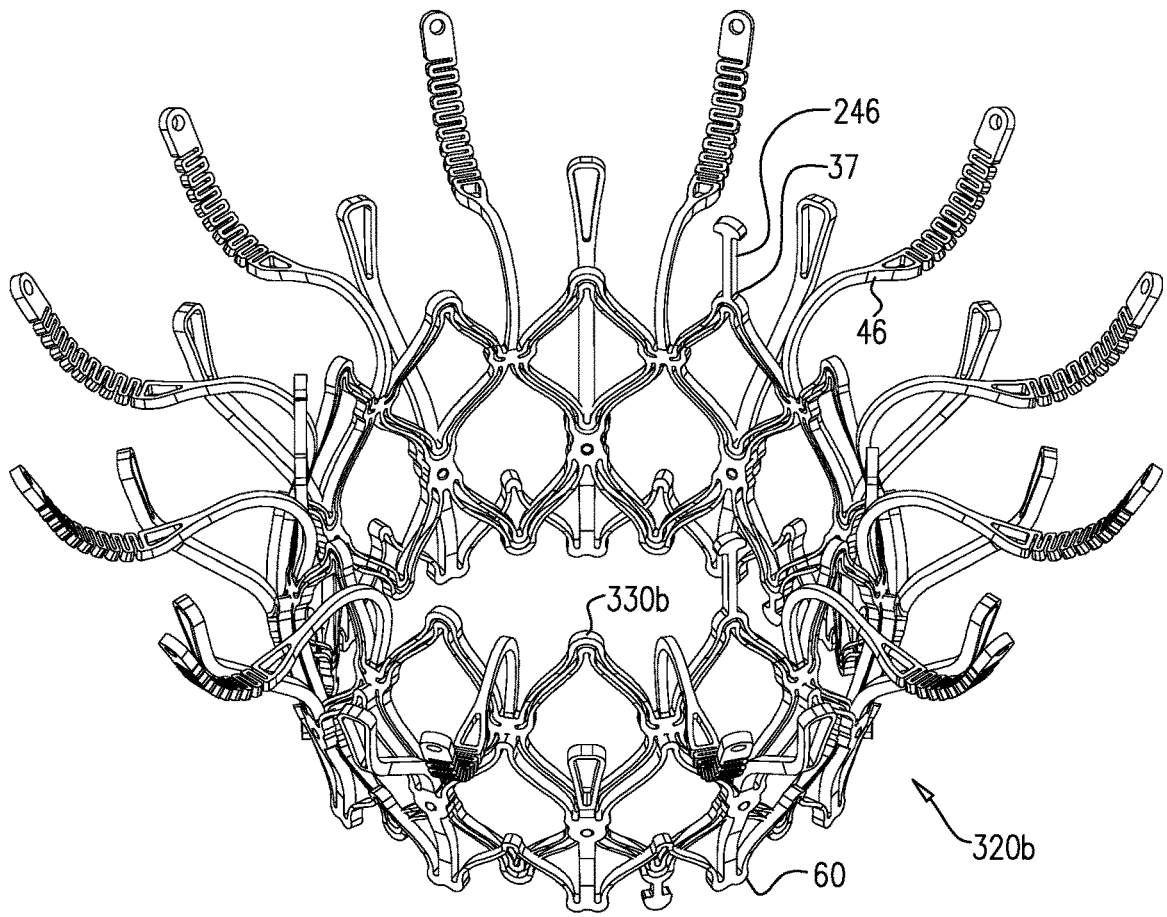

Reference is now made to FIGS. 10A-B, which are schematic illustrations of an inner frame 330b, and an implant 320b comprising inner frame 330b, in accordance with some applications of the invention. Inner frame 330b may be used in place of other inner frames of implants described herein, mutatis mutandis.

Inner frame 330b comprises a valve body (which is a generally tubular portion) 332b that has an upstream end 334b and a downstream end 336b, and is shaped to define a lumen through the valve body from its upstream end to its downstream end. Valve frame 330b further comprises a plurality of arms 46, each of which, in the expanded state, extends radially outward from valve body 332b. Inner frame 330b is typically the same as inner frame 330a, except where noted. Compared to inner frame 330a, inner frame 330b comprises additional joists 28 at upstream end 334b. That is, in contrast to inner frame 330a, for inner frame 330b pairs 108 of joists are also disposed at the upstream side of the upstream row of cells.

In frame 330a, sites 37 are coincident with the upstream extremity of a respective upstream-row cell. In contrast, in frame 330b, sites 37 are not coincident with the upstream extremity of a respective upstream-row cell. Rather, sites 37 are coincident with a minor node that joins the joists that are paired with (e.g., that are parallel with) the joists of the respective upstream-row cell.

Implant 320b is typically the same as implant 320a, except that it comprises inner frame 330b instead of inner frame 330a.

Reference is now made to FIGS. 11A-B, which are schematic illustrations of an inner frame 330c, and an implant 320c comprising inner frame 330c, in accordance with some applications of the invention. Inner frame 330c may be used in place of other inner frames of implants described herein, mutatis mutandis.

Inner frame 330c comprises a valve body (which is a generally tubular portion) 332c that has an upstream end 334c and a downstream end 336c, and is shaped to define a lumen through the valve body from its upstream end to its downstream end. Valve frame 330c further comprises a plurality of arms 46, each of which, in the expanded state, extends radially outward from valve body 332c. Inner frame 330c is typically the same as inner frame 330b, except where noted.

In general, for implants having an expandable cellular structure, such as the valve bodies described herein, for a given size of the implant, a cellular structure that defines fewer, larger cells, advantageously facilitates radial compression (i.e., "crimping") to a smaller diameter than does a comparable cellular structure that defines more, smaller cells. However, this is typically at the expense of strength and rigidity of the expanded valve. As described hereinabove, the presence of additional joists 28 (e.g., in inner frames 330a, 330b, and 330c) to form pairs 108 is hypothesized to increase strength and rigidity, in particular with respect to compression toward the central longitudinal axis. As a result, it is further hypothesized by the inventors that using such a paired joist cellular structure facilitates reducing the number, and increasing the size, of the cells of the valve body, in order to achieve a valve body that is radially compressible to a smaller diameter while maintaining sufficient strength and rigidity.

Accordingly, valve body 332c of inner frame 330c has fewer, larger cells compared to valve body 32 of inner frame 30, and is therefore radially compressible to a smaller diameter. Whereas each row of cells of valve body 32 includes 12 cells, each row of cells of valve body 332c includes 9 cells. More generally, whereas the rotationally-symmetrical pattern of valve body 32 has 12 repeats (e.g., 12 cells per cell row, 12 minor nodes per minor-node row, 12 major nodes per major-node row, 12 coupling elements, 12 arms 46), the rotationally-symmetrical pattern of valve body 332c has only 9 repeats. (Both valve body 32 and valve body 332c typically have 3 appendages 80 and 3 projections 246.) Both valve body 32 and valve body 332c define two rows of cells. Therefore, whereas valve body 32 defines 24 cells in total, valve body 332c defines 18 cells in total. Whereas valve body 32 defines exactly 24 major nodes, valve body 332c defines exactly 18 major nodes.

For some applications, and as shown, inner frame 330c comprises additional joists 28 at upstream end 334c (e.g., similarly to inner frame 330b). That is, for such applications, pairs 108 of joists are typically also disposed at the upstream side of the upstream row of cells of inner frame 330c. For such applications, implant 320c is typically the same as implant 320b, except that implant 320c comprises 9 rotationally-symmetrical repeats, rather than 12.

For some applications, inner frame 330c does not comprise additional joists 28 at upstream end 334c, and is instead more like inner frame 330a in this regard.

Reference is again made to FIGS. 9A-11B. It is to be noted that although the above-described arrangements of joists connected at major and minor nodes are described in the context of a prosthetic heart valve, the scope of the invention includes using such arrangements in other implants or components thereof that comprise a cellular structure, such as stents.

Reference is made to FIGS. 12A-H, which are schematic illustrations of a technique for use with a frame of a prosthetic valve, in accordance with some applications of the invention. The technique is for augmenting a tissue-engaging flange of the frame with a soft pad 300. To illustrate the technique, FIGS. 12A-H show the technique being used to augment flanges 54 of outer frame 60 with soft pads 300, but it is to be noted that the technique may be used with any suitable frame, mutatis mutandis.

Figure 12A:
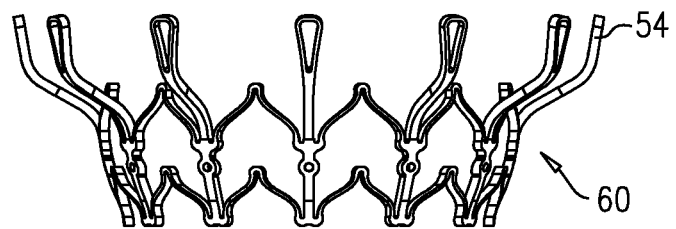
FIGS. 12A-H are schematic illustrations of a technique for use with a frame of a prosthetic valve, in accordance with some applications of the invention.
Figure 12B:
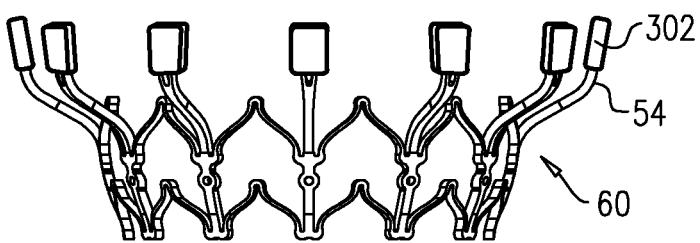
Figure 12C:
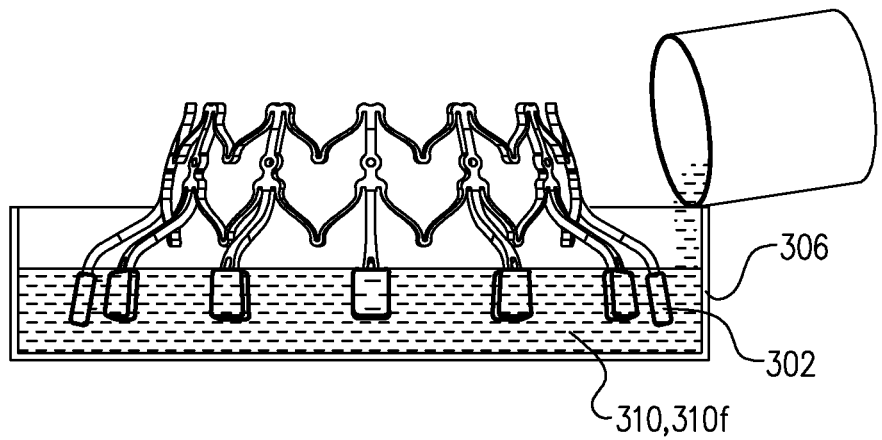
Figure 12D:
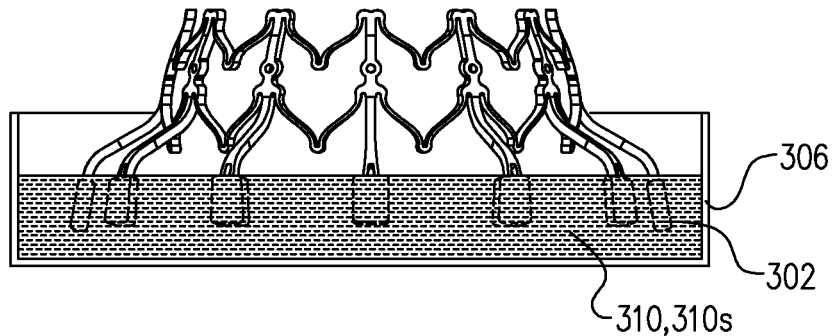
Figure 12E:
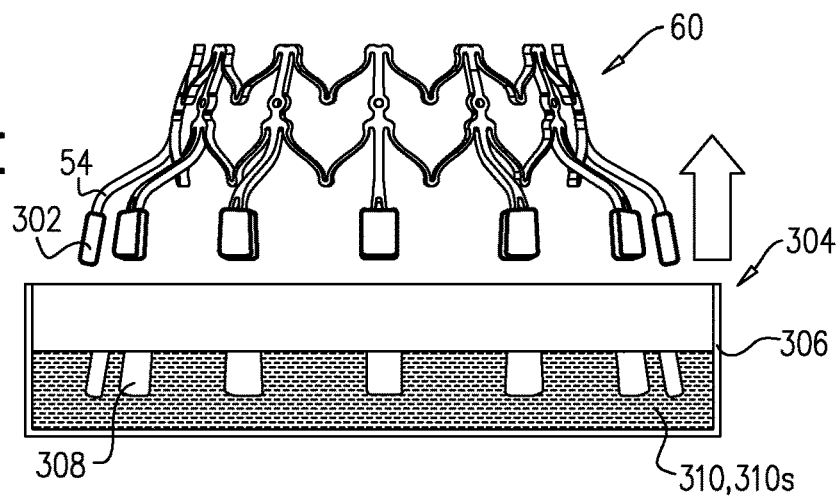

FIG. 12A shows frame 60, which has tissue-engaging flanges 54. A model 302 of a soft pad 300 with which each flange 54 is to be augmented is affixed to the respective flange (FIG. 12B). Subsequently, a mold 304 is formed by (i) positioning frame 60 such that models 302 are supported within a fluid 310f of a first substance 310 while the first substance solidifies, and (ii) subsequently, removing the models from the first substance, leaving a cavity in the solidified first substance. For example, and as shown in FIGS. 12C-E, a bath 306 of fluid 310f may be prepared, and frame 60 may be inverted and lowered into the bath such that models 302 are supported within the fluid (FIG. 12C). First substance 310 is allowed to solidify into solidified first substance 310s (FIG. 12D). Subsequently, frame 60 is withdrawn from the bath, thereby removing models 302 from solidified first substance 310s, such that each model leaves a respective cavity 308 in solidified first substance 310s (FIG. 12E).

Figure 12F:
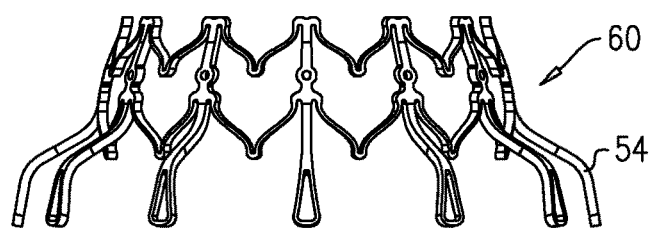
Figure 12G:
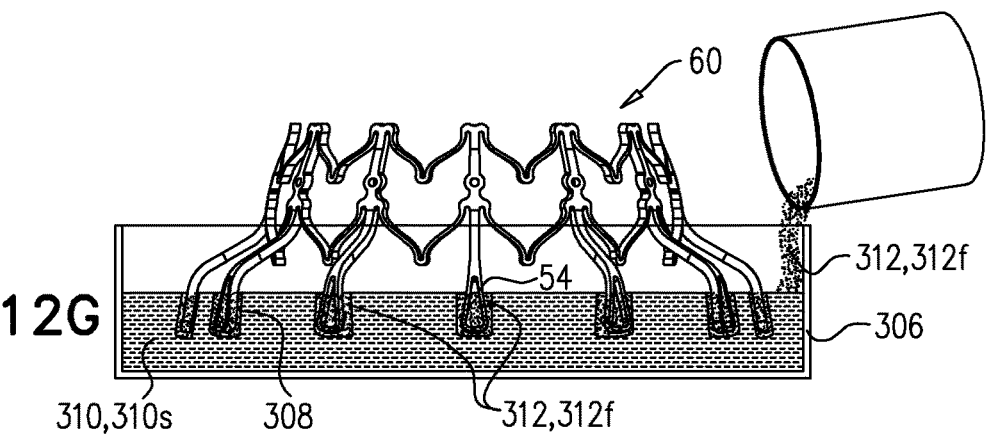
Figure 12H:
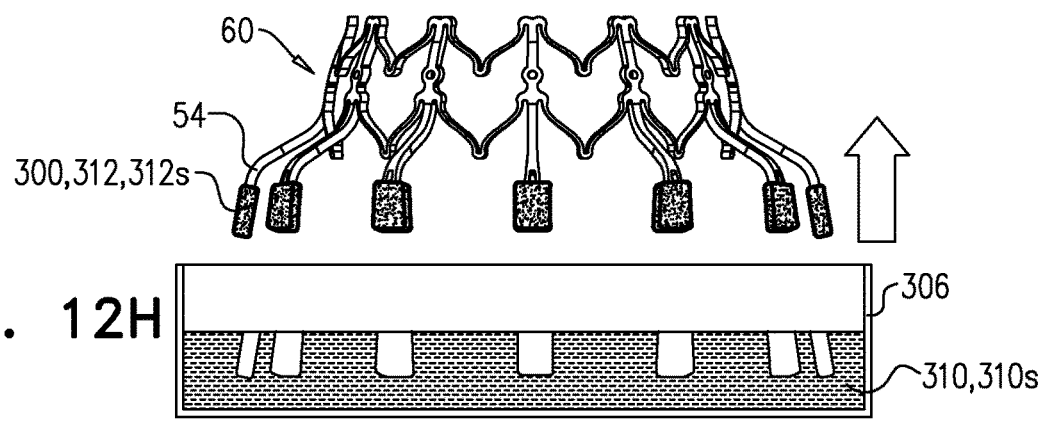

Models 302 are then removed from flanges 54 (FIG. 12F). Pads 300 are then formed by: (i) placing flanges 54 in contact with a second substance 312 by repositioning the frame such that each flange is supported within a respective cavity 308, and introducing a fluid 312f of the second substance to the cavity (FIG. 12G), and (ii) while the flange remains in contact with the second substance, allowing the second substance to solidify into solidified second substance 312s and to become affixed to the flange. Subsequently, flanges 54 are removed from cavities 308 with formed pads 300 (comprising solidified second substance 312s) affixed to the flanges (FIG. 12H).

The technique described with reference to FIGS. 12A-H may be used with a frame that has a single tissue-engaging flange. However, as shown, the technique is typically used with a frame that has a plurality of flanges, e.g., to augment all the flanges simultaneously. It is to be noted that flanges 54 are not all disposed on the same side of frame assembly 22 (i.e., after frames 30 and 60 have been attached to each other). For example, flanges 54 are not all at the upstream end of the prosthetic valve or at the downstream end of the prosthetic valve. Rather, they are disposed downstream of the tips of arms 46 and upstream of downstream end 26.

Furthermore, flanges 54 are arranged circumferentially around the longitudinal axis of the prosthetic valve. Flanges 54 (and eventually pads 300) are arranged circumferentially around frame 30 longitudinally between the upstream end and the downstream end of frame 30, exclusive. For some applications, the flanges being not all disposed on the same side might inhibit the use of the technique of FIGS. 12A-H to simultaneously augment all of the flanges. For example, it may be difficult to place all of models 302 into the fluid first substance, or to place all of flanges 54 into the fluid second substance, without also placing other portions of the frame assembly into the fluid substance. The two-frame nature of frame assembly 22 advantageously allows flanges 54 to be augmented with pads before frame 60 is attached to frame 30. Because all of flanges 54 are disposed at the same side (e.g., the upstream side) of frame 60, they can all be placed into the fluid substances simultaneously.

An alternative solution is also contemplated by the inventors, in which an annular bath is positioned circumscribing the central portion of the prosthetic valve or frame assembly, such that all flanges can be placed into the fluid substances even when the flanges are not all disposed on the same side of a prosthetic valve or frame assembly.

For some applications, substance 310 and/or substance 312 may be a mixture of constituents that is initially fluid upon mixing, and that solidifies as the constituents react with each other. For some applications, fluid substance 310f and/or fluid substance 312f is fluid because it is in a molten state, and solidifies as it cools. When solidified, second substance 312 is typically soft, flexible, and/or resilient. For some applications, second substance 312 (or at least solidified second substance 312s) is a foam. For some applications, second substance 312 comprises silicone, polyurethane, a thermoplastic elastomer such as Santoprene™, and/or polyether block amide.

For some applications, the techniques described with reference to FIGS. 12A-H are alternatively or additionally used, mutatis mutandis, to augment the downstream end of the implant with one or more pads, e.g., to serve a similar function to ring 78 described hereinabove.

Reference is made to FIGS. 13A-E, 14A-D, 15A-C, 16A-C, 17, 18A-C, and 19, which are schematic illustrations of an implant 420, and steps in the assembly of the implant, in accordance with some applications of the invention. In particular, these figures illustrate steps in the attachment of various flexible components to the frame assembly of the implant, such as steps in the dressing of the frame assembly with various sheets of flexible material. Implant 420 is shown as comprising frame assembly 222, and is typically identical to implant 220 except for where described otherwise. However, it is to be noted that the steps described with reference to FIGS. 13A-18C may be used, mutatis mutandis, to assemble other implants, including the other implants described herein.

Figure 13C:
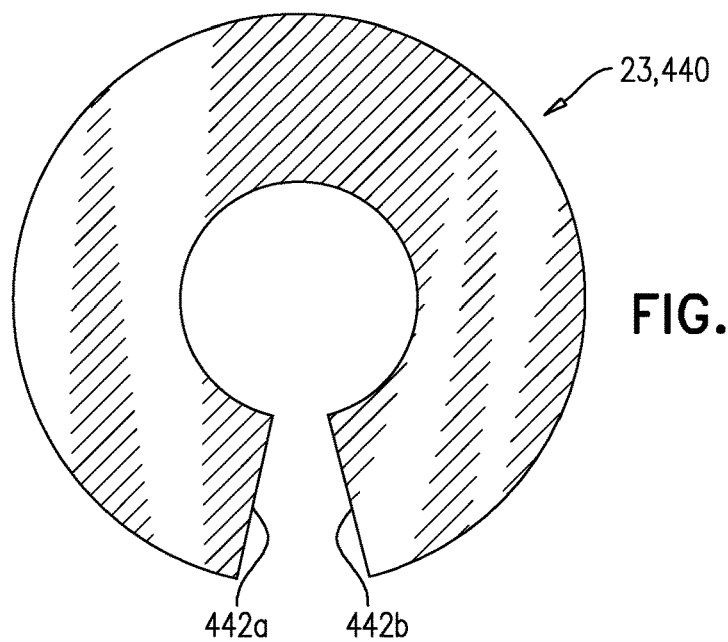

FIGS. 13A-E show flexible components of implant 420. FIGS. 13A-B are perspective and side views, respectively, of a valvular assembly 430, comprising leaflets 58 arranged to serve as a check valve. In valvular assembly 430, each leaflet 58 defines (i) an upstream surface 457, past which blood will flow through implant 420 in an upstream-to-downstream direction, and (ii) a downstream surface 459, against which blood will press when the valvular assembly closes and inhibits blood flow in a downstream-to-upstream direction. Valvular assembly 430 typically further comprises a liner 427 and/or a plurality of connectors 432. Liner 427 of implant 420 generally corresponds to liner 27 of implant 20, mutatis mutandis. Typically, valvular assembly 430 comprises three leaflets 58 and three connectors 432. Connectors 432 couple the leaflets to each other to form commissures, and are used to secure the leaflets, at the commissures, to frame assembly 222. Connectors 432 are arranged circumferentially, and leaflets 58 extend radially inward from the connectors. For some applications, valvular assembly 430, and connectors 432 in particular, are as described in PCT patent application publication WO 2018/029680 to Hariton et al., and/or U.S. patent application Ser. No. 15/878,206 to Hariton et al. (now U.S. Pat. No. 9,987,132), both of which are incorporated herein by reference.

Each leaflet 58 is attached (e.g., stitched) to liner 427 along a line (e.g., a stitch line) 437. Each leaflet 58 defines a free edge 458, which is typically straight, and at which the leaflet coapts with the other leaflets 58. Stitch line 437 is typically curved. Each leaflet typically defines a curved edge (e.g., an upstream edge) 456 at which the leaflet is attached to liner 427. The curve of edge 456 and/or stitch line 437 is concave toward the downstream end of valvular assembly 430, such that edge 456 and/or stitch line 437 (i) become closer to the downstream end of the valvular assembly at connectors 432, and (ii) are closest to the upstream end of the valvular assembly about midway circumferentially between the connectors. That is, edge 456 has an apex about midway circumferentially between connectors 432.

Typically, and as shown, leaflets 58 extend further axially downstream (i.e., downstream with respect to axis ax1) than does liner 427. Therefore, a downstream portion of each leaflet 58 is typically circumferentially exposed from liner 427. For some applications, and as shown, liner 427 is shaped to define regions 428 at which a downstream edge 436 of the liner recedes from the downstream end of valvular assembly 430. At each region 428, more of the respective leaflet 58 is circumferentially exposed. Each region 428 is typically circumferentially aligned with the concavity defined by edge 456 and/or stitch line 437. At regions 428, downstream edge 436 of liner 427 is typically stitched to ring 182 of frame 230. Therefore, for some applications, the most upstream parts of downstream edge 436 of liner 427 are closer to the upstream end of the implant than is the most downstream parts of arms 46. As described in more detail hereinbelow, in implant 420, regions 428 of liner 427 facilitate the provision of windows 482 into a pouch 490.

FIG. 13C shows a sheet 440 of flexible material. Typically, and as shown, sheet 440 is provided flat, and in the shape of a major arc of an annulus, having a first arc-end 442*a* and a second arc-end 442*b*. Sheet 440 of implant 420 generally corresponds to annular sheet 25 of implant 20, mutatis mutandis.

Figure 13D:
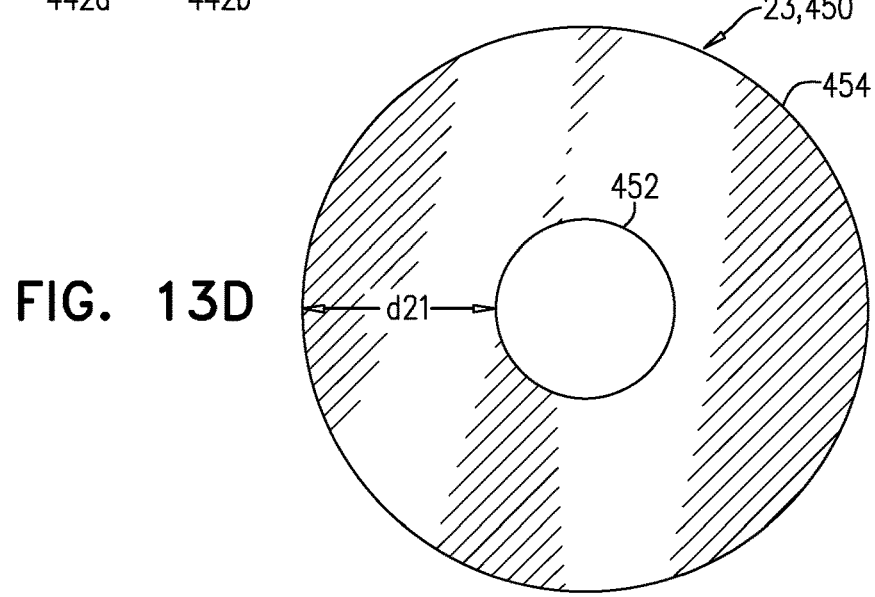

FIG. 13D shows a sheet 450 of flexible material. Sheet 450 is annular, and defines an inner perimeter 452, an outer perimeter 454, and a radial dimension d21 therebetween.

Figure 13E:
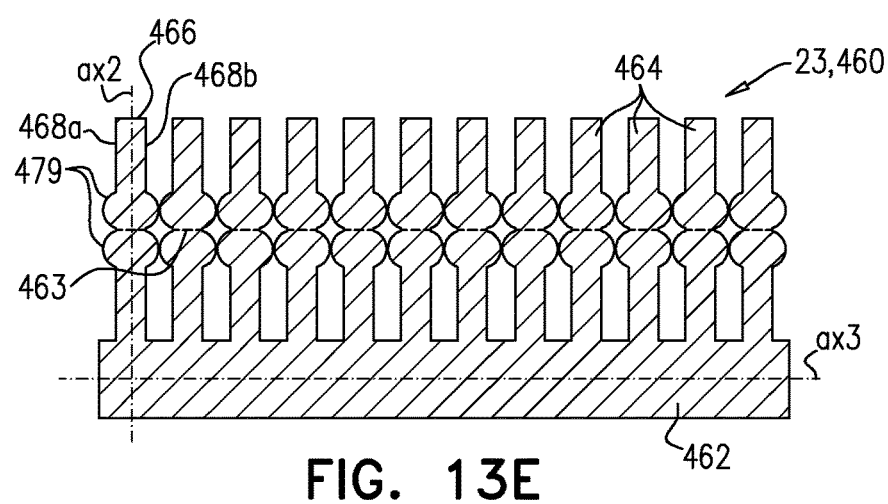

FIG. 13E shows a sheet 460 of flexible material. Sheet 460 is shaped to define a belt 462 and a plurality of elongate strips 464. Each strip 464 defines a respective central strip-axis ax2, and extends along its strip-axis from belt 462 to the end 466 of the strip. Typically, belt 462 is linear and defines a belt-axis ax3, and strip-axis ax2 is orthogonal to the belt-axis. Typically, strips 464 are parallel to each other. Each strip 464 has first and second edges 468 (e.g., a first edge 468*a* and a second edge 468*b*), which extend on either side of axis ax2, between belt 462 and end 466.

As indicated by the reference numeral 23, sheets 440, 450, and 460 may all be considered components of sheeting 23. For some applications, liner 427, sheet 440, sheet 450, and/or 460 comprise (e.g., consist of) the same material as each other. Typically, sheets 440, 450, and 460 are provided as flat, and are subsequently shaped during assembly of implant 420, e.g., as described hereinbelow.

Figure 14A:
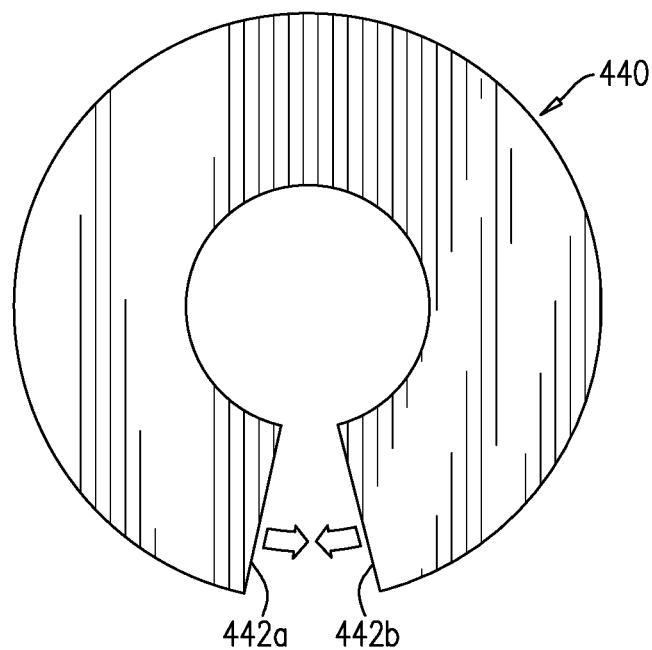
Figure 14B:
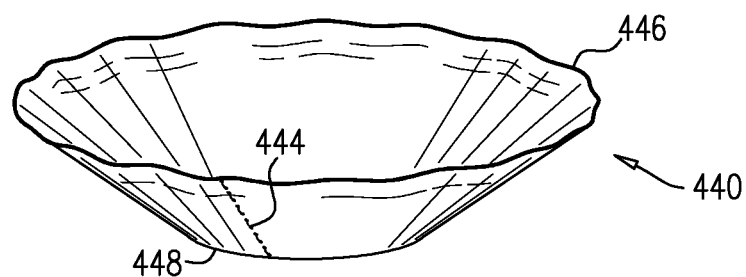
Figure 14C:
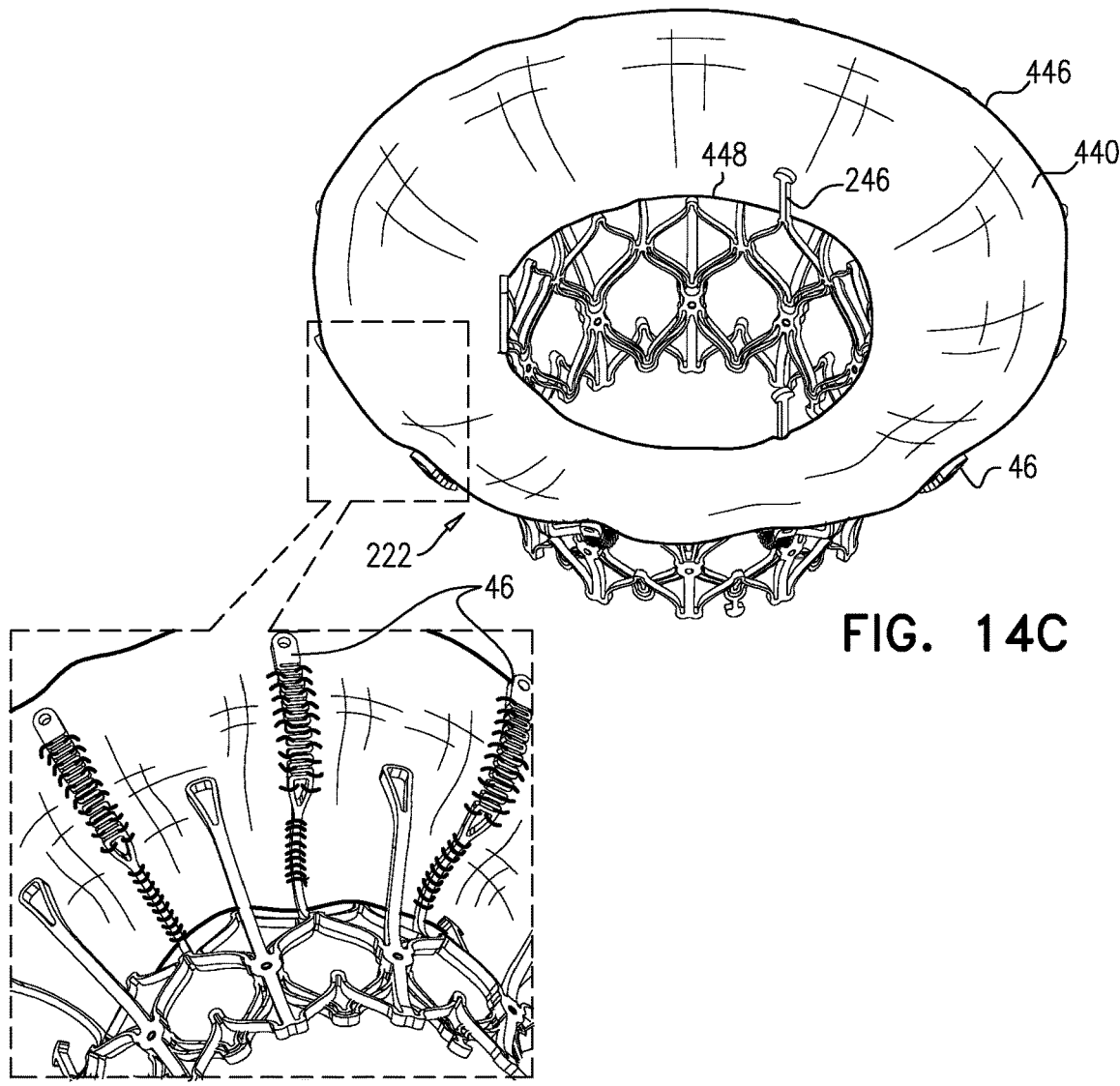
Figure 14D:
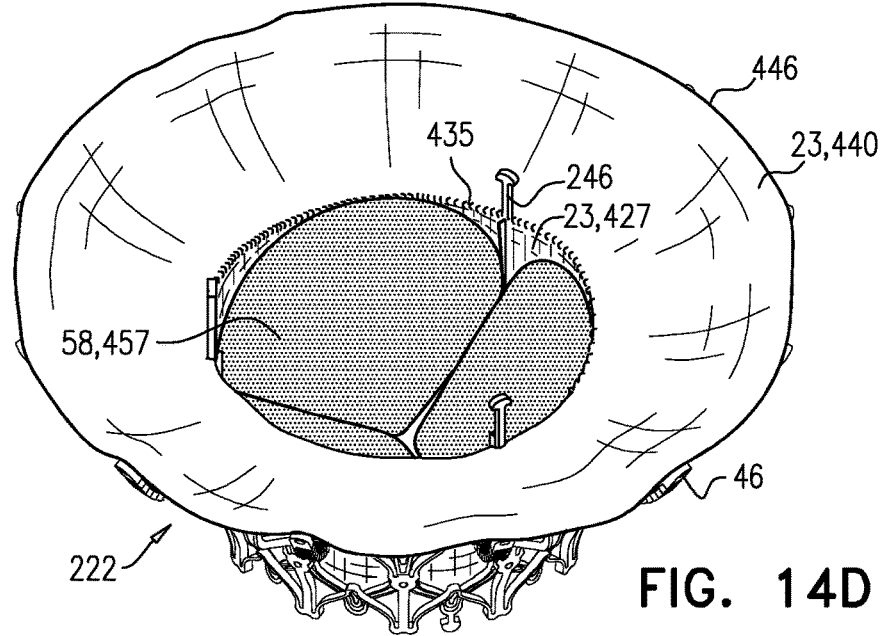

For applications in which sheet 440 is provided flat and in the shape of a major arc of an annulus, sheet 440 is shaped into an open frustum by attaching (e.g., stitching) ends 442*a* and 442*b* together (FIGS. 14A-B). This is represented by a stitch line 444 in FIG. 14B. Alternatively, sheet 440 may be provided in the open frustum shape. The open frustum shape has a greater perimeter 446 at a first base of the frustum, and a smaller perimeter 448 at a second base of the frustum. Perimeter 448 defines an opening, and sheet 440 is stitched to arms 46 such that the opening is aligned with the lumen defined by valve body 32 of frame 30 (FIG. 14C), and typically such that the sheet covers an upstream side of the arms. FIG. 14D shows valvular assembly 430 having been coupled to frame assembly 222. This step may be performed after sheet 440 is stitched to arms 46 (as shown) or beforehand. Valvular assembly 430 is placed inside valve body 32 of frame 30, and is attached by stitching connectors 432 and liner 427 to frame assembly 222. Connectors 432 are typically stitched to ring 184 and/or ring 186. For some applications, the attachment of connectors 432 to frame assembly 222 is as described in PCT patent application publication WO 2018/029680 to Hariton et al., and/or U.S. patent application Ser. No. 15/878,206 to Hariton et al. (now U.S. Pat. No. 9,987,132), both of which are incorporated herein by reference.

Smaller perimeter 448 of sheet 440 is stitched to an upstream edge 434 of liner 427, to form a substantially sealed channel through implant 420. This stitching is represented by a stitch line 435. Typically, and as shown, projections 246 extend between, and are sandwiched between, perimeter 448 of sheet 440 and upstream edge 434 of liner 427. Upstream edge 434 is typically circular.

Downstream edge 436 of liner 427 is stitched to valve body 32 of frame 30. Typically, downstream edge 436 is shaped and positioned to approximately conform to rings 182 and 184, and is stitched to these rings.

It is to be noted that throughout this patent application (including the specification and the claims) stitching of a perimeter or edge of a sheet to a perimeter or edge of another sheet, does not necessarily mean that the sheets are stitched at their absolute edges (i.e., their free edges). Rather, in this context, the "perimeter" or "edge" also includes the adjacent area of the sheet, as is understood by one of ordinary skill in the stitching art, and as is typically required for effective stitching.

Valvular assembly 430 is typically positioned within frame assembly such that the apex of curved edge 456 of each leaflet 58 is disposed axially close to (e.g., axially within 2 mm of, e.g., within 1 mm of) an upstream end 34 of valve body 32. Valvular assembly 430 is also typically positioned within frame assembly such that free edge 458 of each leaflet 58 is disposed downstream of leg 50.

Figure 15A:
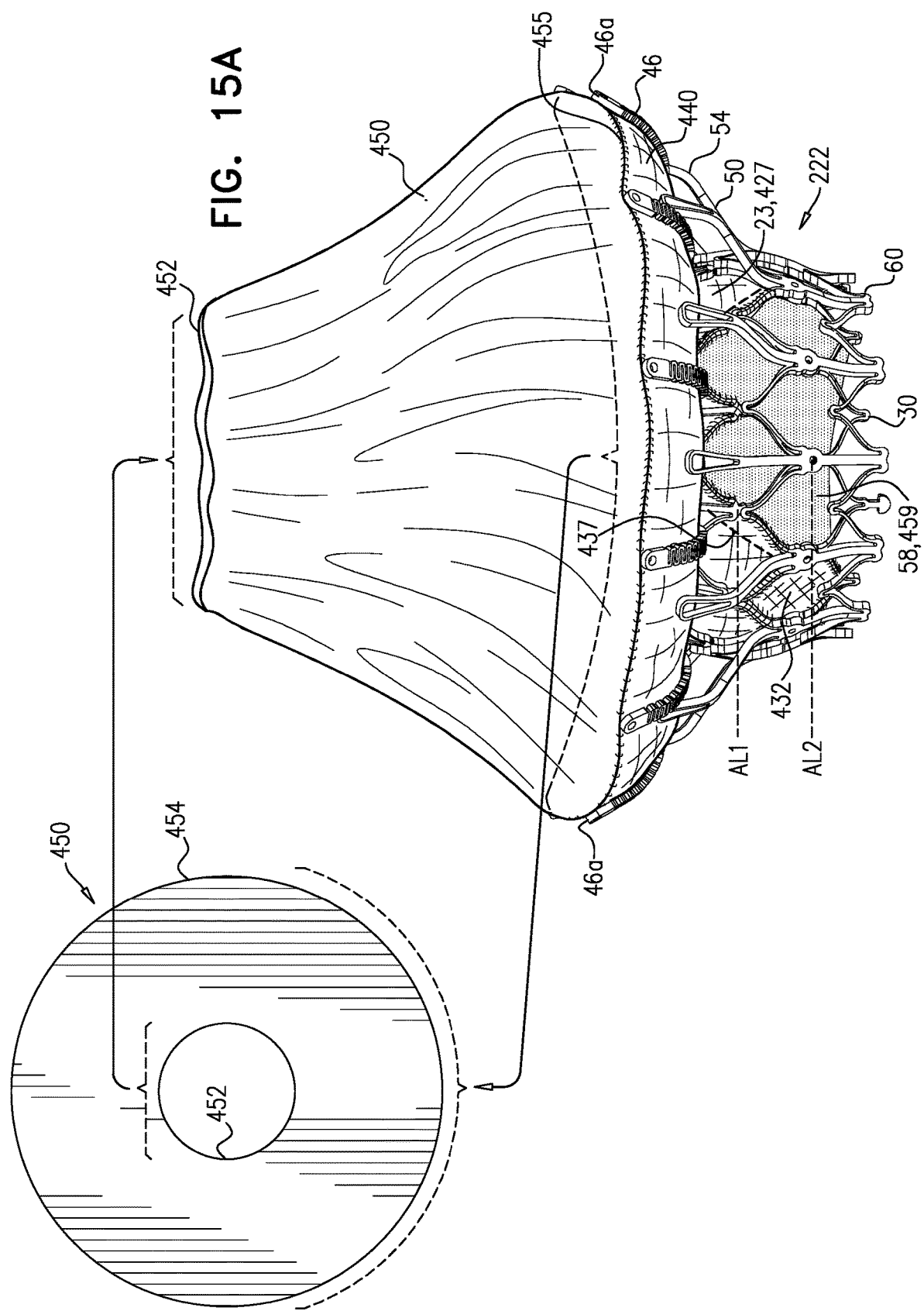
Figure 15B:
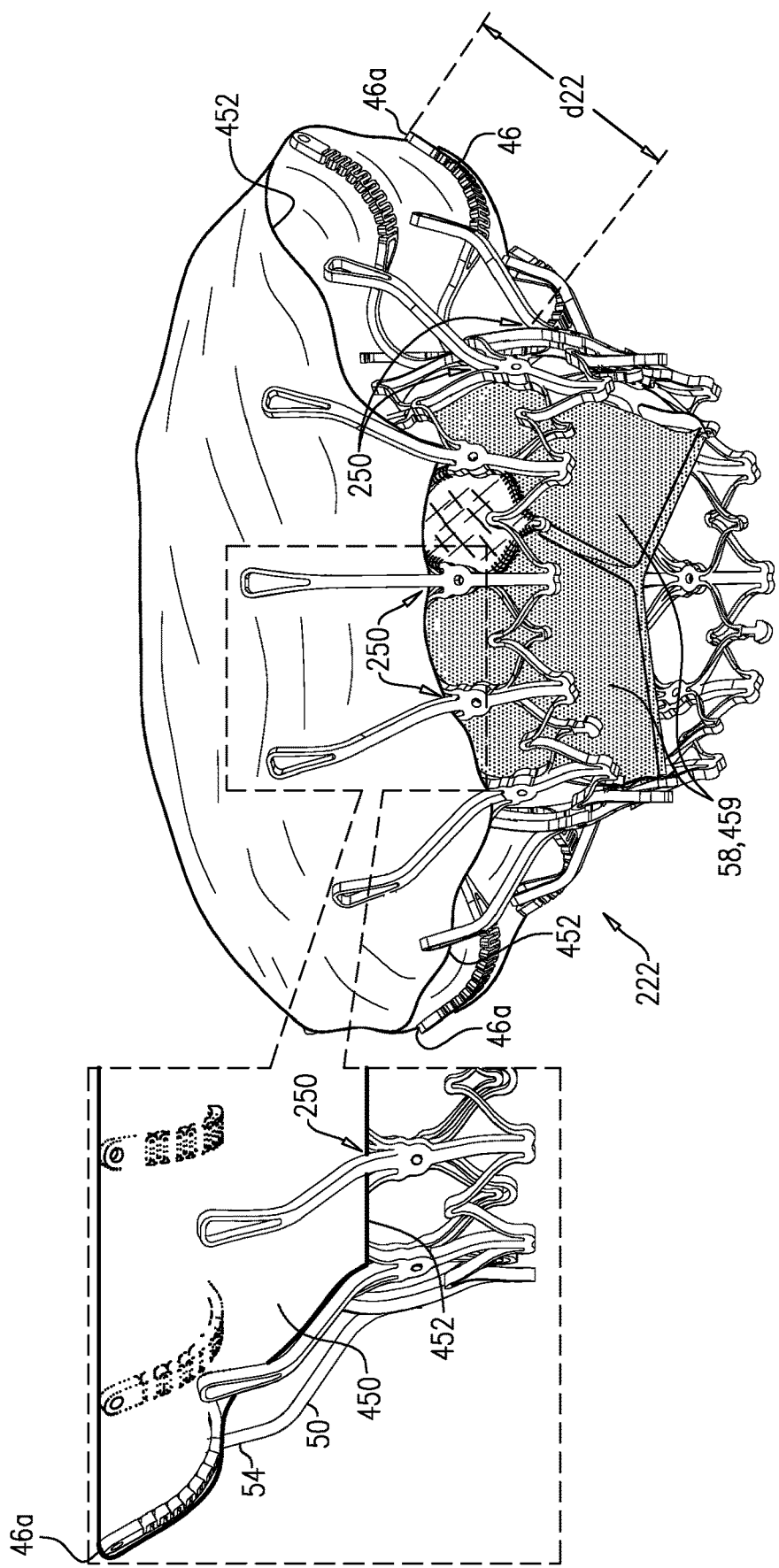
Figure 15C:
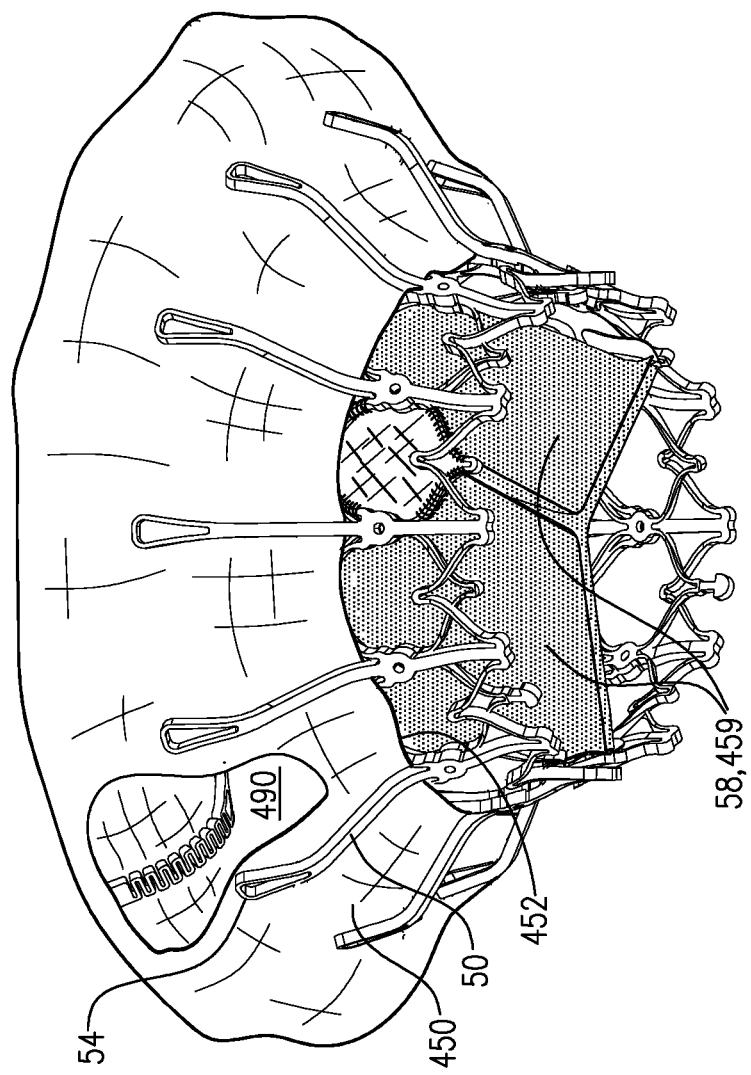

Subsequently, sheet 450 is attached to frame assembly 222 (FIGS. 15A-C). Outer perimeter 454 of sheet 450 is stitched to greater perimeter 446 of the sheet 440 (FIG. 15A). This is represented by stitch line 455. Typically, perimeter 454 is larger than perimeter 446, and is brought inwards to be stitched to perimeter 446 (e.g., making sheet 450 frustoconical), with inner perimeter 452 disposed axially away from frame assembly 222 (e.g., further axially away than outer perimeter 454 from the frame assembly).

Subsequently, sheet 450 is everted by bringing inner perimeter 452 toward frame assembly 222, and passing the inner perimeter around the tips 46*a* of arms 46—i.e., axially past the tips 46*a* of all of the arms (FIG. 15B). Typically, and as shown, arms 46 collectively define an arm-span d23 that is wider than perimeter 452. That is, the tips 46*a* of arms 46 typically define a perimeter that is greater than perimeter 452. For some applications, the passage of inner perimeter 452 around the tips 46*a* of arms 46 is facilitated by bending (e.g., temporarily) one or more of arms 46.

Inner perimeter 452 is advanced over at least part of valve body 32 toward a downstream end of frame assembly 222, and is stitched in place. Typically, perimeter 452 is advanced between the valve body and legs 50, such that perimeter 452 circumscribes valve body 32, and legs 50 are disposed radially outside of sheet 450. As described hereinabove, each leg 50 extends radially outward and in an upstream direction from a respective leg-base 66 to a respective leg-tip 68. Each leg therefore extends at an acute angle to define a respective cleft 250 between the leg and valve body 32 (e.g., the tubular portion), the cleft open to the upstream direction. Typically, perimeter 452 is tucked into clefts 250, and is stitched into place. Frame assembly 222 defines a distance d22, measured along a straight line, between the ends of arms 46 and clefts 250. For clarity, distance d22 may be defined as a distance between (i) an imaginary ring described by the ends of arms 46, and (ii) an imaginary ring described by clefts 250.

The dimensions and positioning of sheet 450 defines an inflatable pouch 490 that is bounded by sheet 450 (e.g., defining an outer and/or downstream wall of the pouch), sheet 440 (e.g., defining an upstream wall of the pouch), and liner 427 (e.g., defining an inner wall of the pouch). Pouch 490 typically circumscribes the valve body of frame assembly 222. As described in more detail hereinbelow, at least one respective window 482 into pouch 490 is defined between each leaflet 58 and perimeter 452.

Figure 16A:
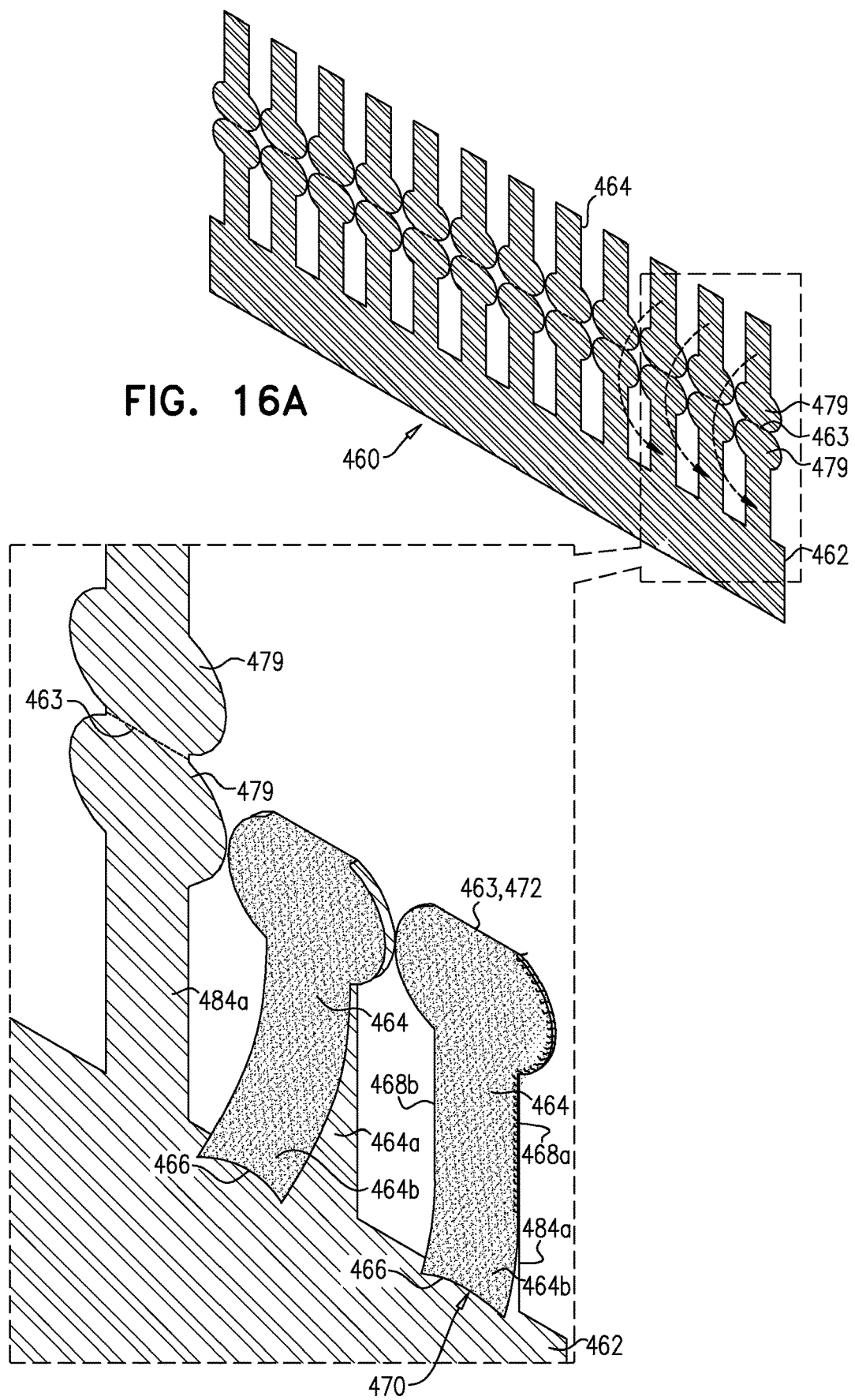
Figure 16B:
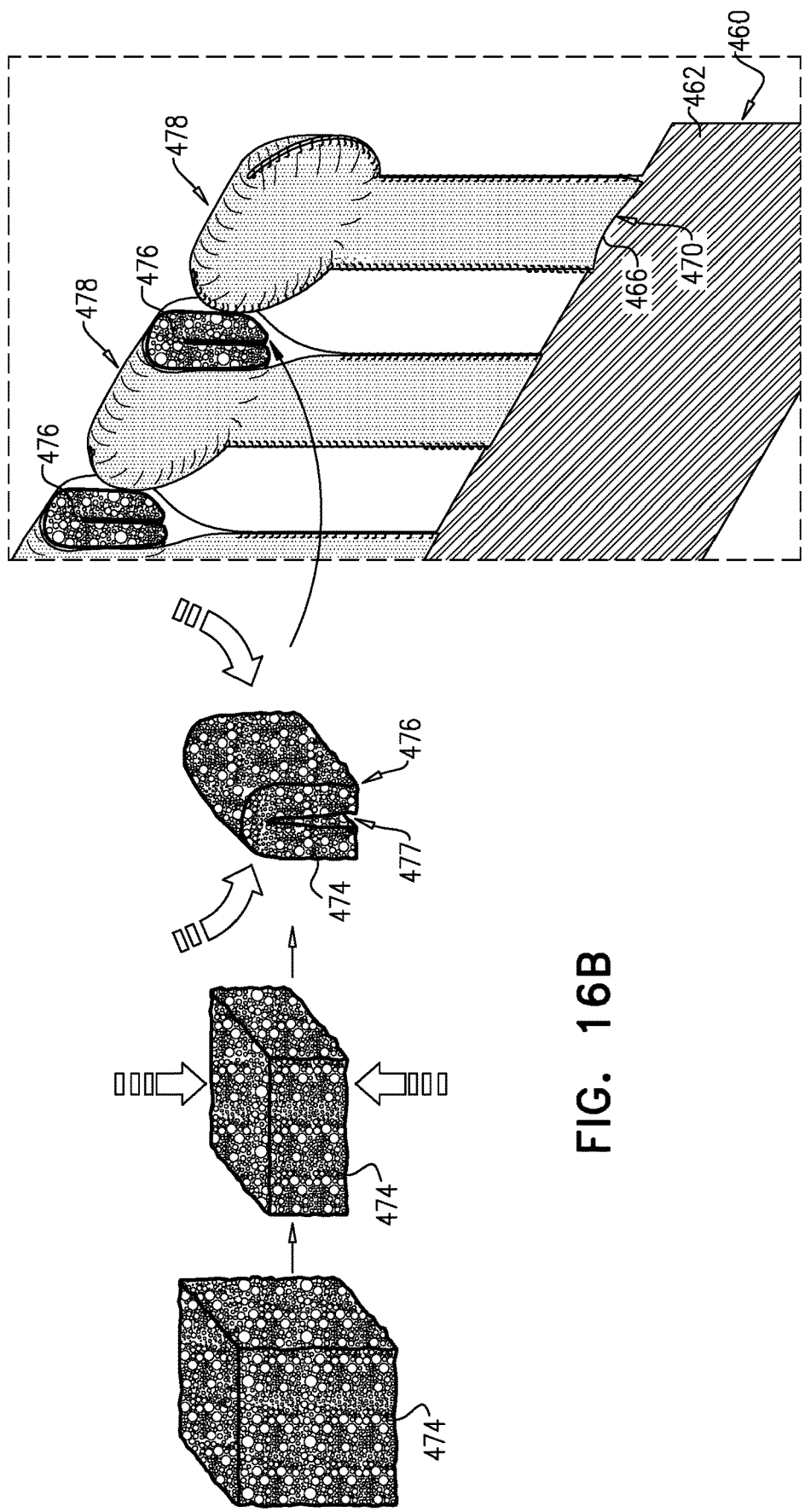
Figure 16C:
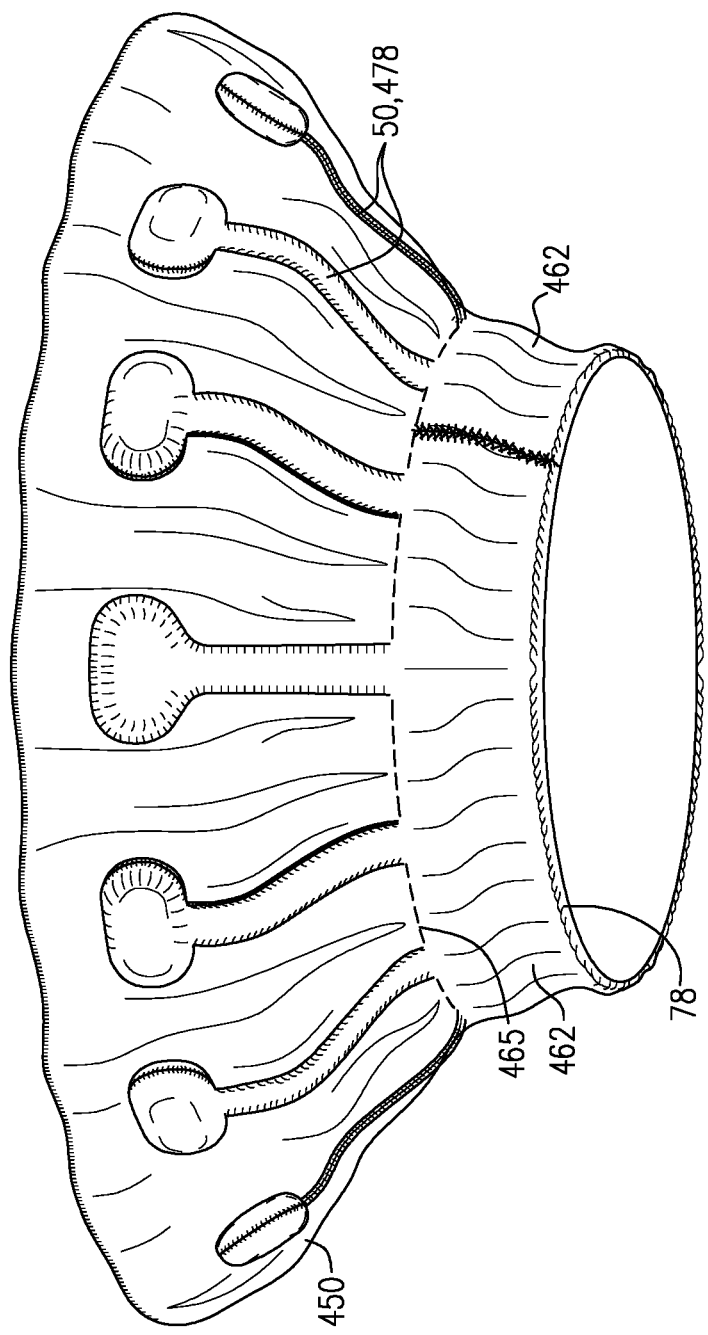

FIG. 16A-C show steps in dressing frame assembly 222 with sheet 460, in accordance with some applications of the invention. Each strip 464 is formed into a respective pocket 478 (FIGS. 16A-B). Each strip is folded over itself, about a fold-line 463 that is orthogonal to strip-axis ax2, thereby forming (i) a first strip-portion 464a that extends from belt 462 to the fold-line, and (ii) a second strip-portion 464b that extends from fold-line back toward the belt. First strip-portion 464a and second strip-portion 464b are stitched together at first edge 468a and second edge 468b. The resulting pocket 478 is typically elongate, and has (i) an opening 470 defined at least in part by end 466 of the strip, and (ii) a tip 472 at the fold-line.

For some applications, a soft pad 476 is provided in each pocket 478, typically at tip 472. For some such applications, and as shown in FIG. 15B, pad 476 is formed from a piece of foam 474 (e.g., comprising polyurethane). Piece of foam 474 may initially be generally cubic. For some applications, and as shown, piece of foam 474 is folded to form a niche 477 in pad 476, typically after having been at least partly flattened by compression. Pad 476 may be introduced into pocket 478 before the pocket is fully formed (e.g., as shown), or may be subsequently introduced into the pocket via opening 470.

Alternatively, pads 300 may be used in place of pads 476, and may be added to flanges 54 as described with reference to FIGS. 12A-H, mutatis mutandis.

For applications in which pad 476 is used, each strip-portion 464a and 464b typically defines a widened region 479 adjacent to fold-line 463, such that when pockets 478 are formed, a receptacle for pad 476 is formed.

Pockets 478 are subsequently slid onto legs 50, and belt 462 is wrapped around frame assembly 222 downstream of legs 50. For applications in which pads 476 are used, flanges 54 of legs 50 are typically advanced into niches 477 of the pads. Belt 462 (e.g., the edge of the belt from which pockets 478 extend) is stitched to sheet 450. More specifically, the upstream edge of belt 462 is stitched circumferentially to perimeter 452 of sheet 450. This is represented by a stitch line 465. Therefore, once implant 420 is assembled, the edge of belt 462 from which pockets 478 extend is an upstream edge of the belt, while the edge that is closest to the downstream end of the implant is a downstream edge of the belt. Legs 50, within pockets 478, extend radially outward from between belt 462 and sheet 450 (e.g., at stitch line 465).

For some applications, tips 472 and/or pads 476 are further secured to flanges 54 by stitching 475, which may pass through a hole 55 (labeled in FIG. 1A) defined in each flange 54. Stitching 475 is visible in FIGS. 18A-C.

As shown in FIG. 16C, for some applications, polytetrafluoroethylene ring 78 is typically also attached to frame assembly 222. For some such applications, in addition to being stitched to frame assembly 222, ring 78 is also stitched to belt 462 (e.g., to the edge of the belt opposite pockets 478 —i.e., the downstream edge of the belt).

Figure 17:
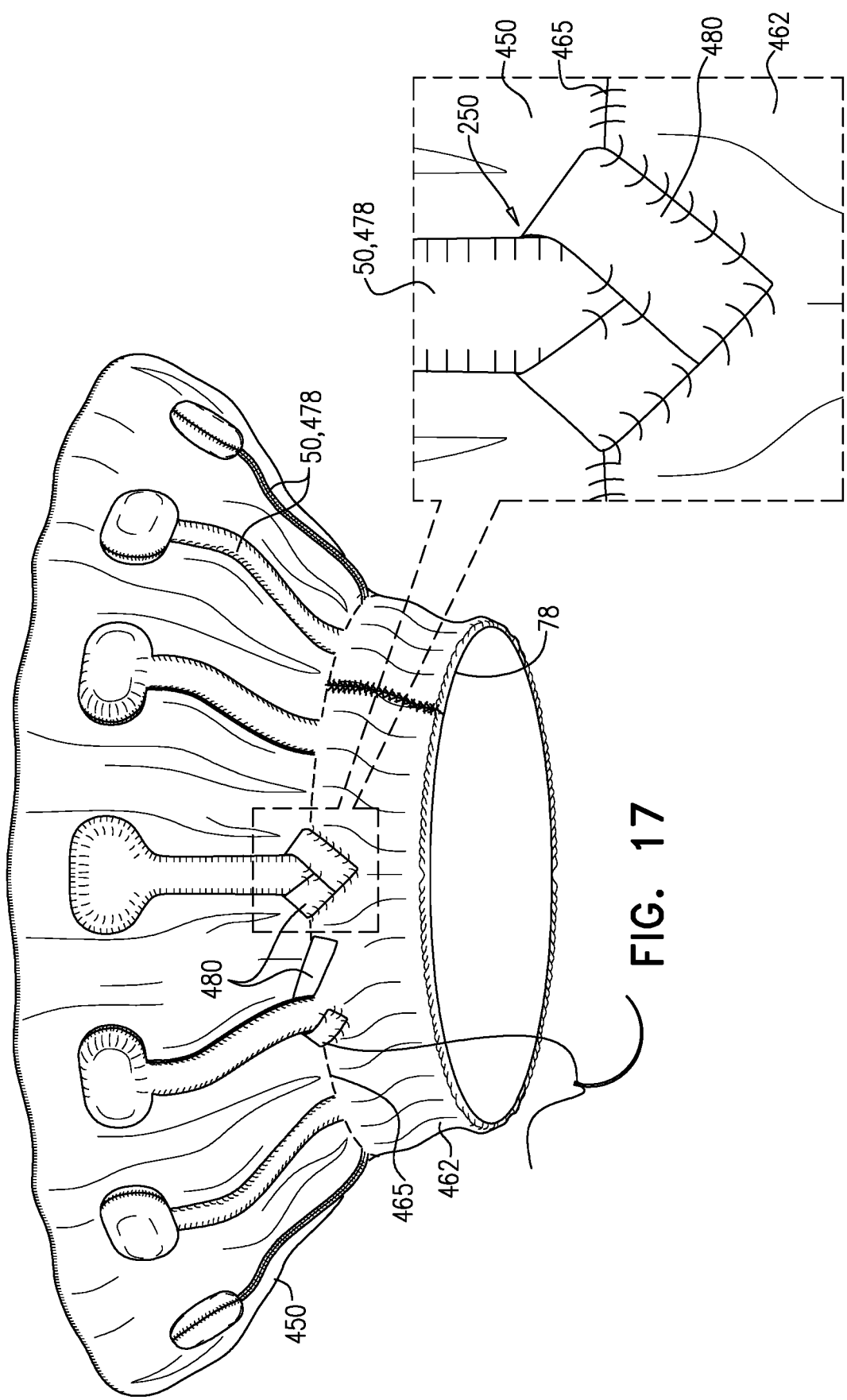

FIG. 17 shows a ribbon 480 being wrapped around the leg-base 66 of each leg 50, in accordance with some applications of the invention. For some applications, the ends of ribbon 480 overlap. Ribbons 480 are stitched in place, but the stitches are typically not disposed in cleft 250. As shown, ribbons 480 may be stitched to belt 462. Although ribbons 480 are shown being used in combination with pockets 478 (and are therefore wrapped around the pockets at leg-base 66), it is to be noted that ribbons 480 may alternatively be used for applications in which legs 50 are generally uncovered. Ribbon 480 covers cleft 250, and is hypothesized by the inventors to reduce a likelihood of tissue (e.g., leaflet or chordae tissue) from becoming wedged in and/or damaged by the cleft.

Figure 18A:
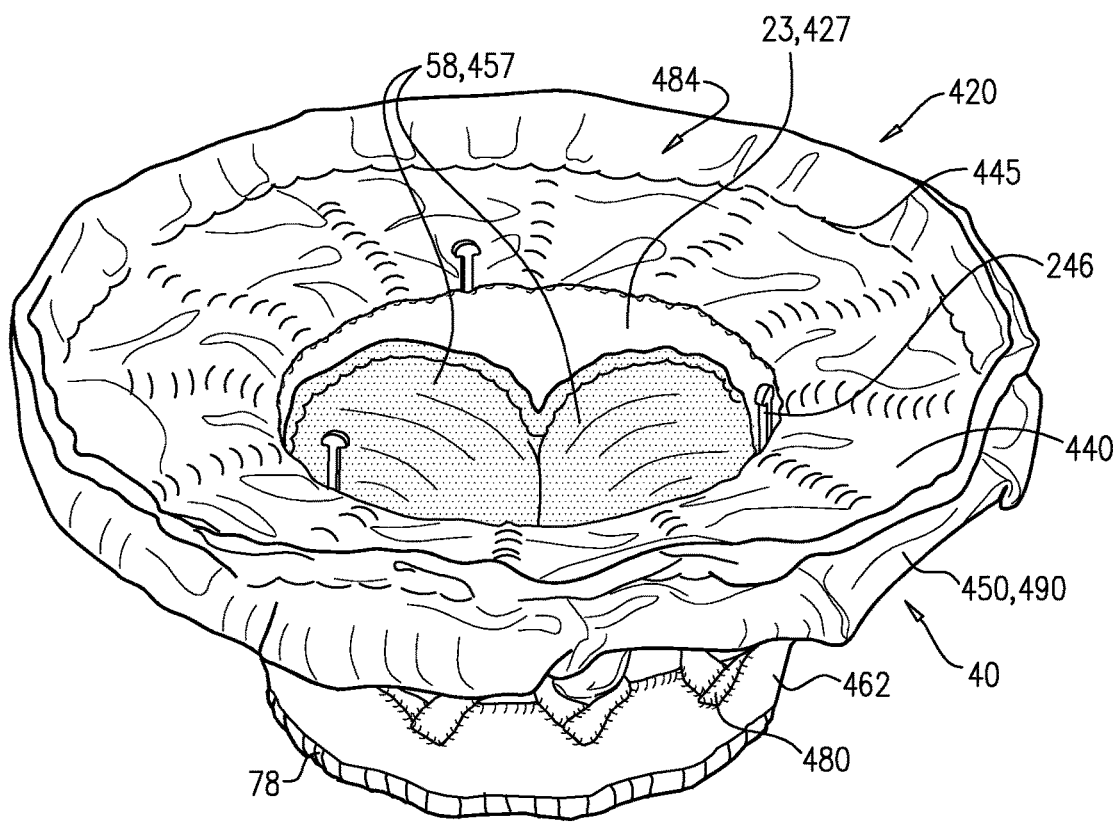
Figure 18B:
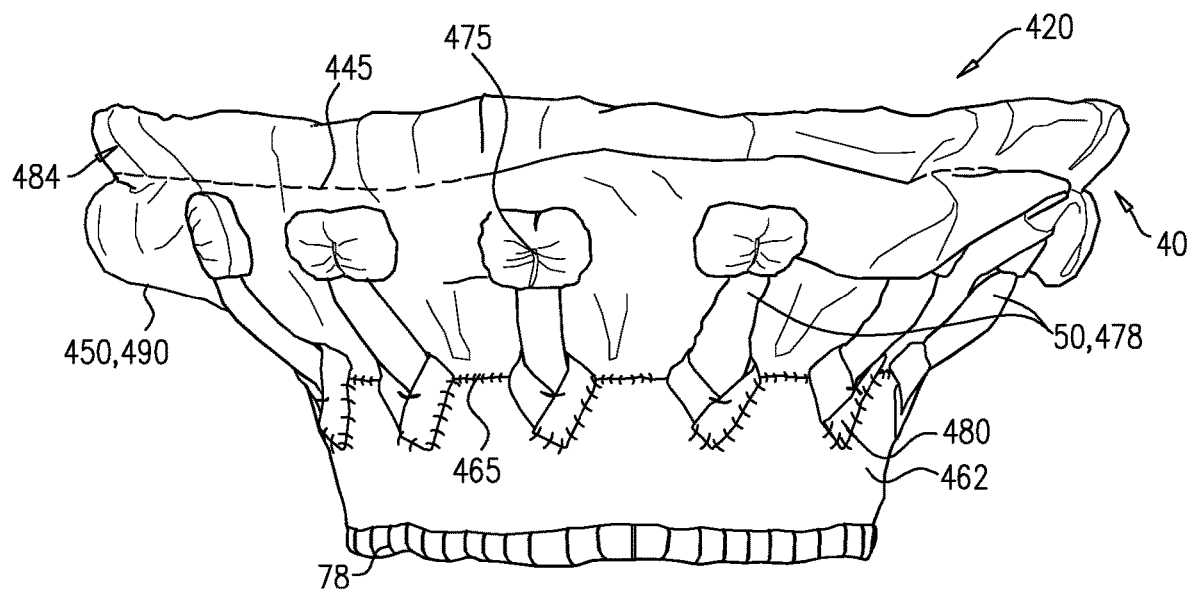

FIGS. 18A-C show implant 420 after its assembly. FIG. 18A is an upper perspective view (e.g., showing upstream surfaces of the implant), FIG. 18B shows a side view, and FIG. 18C shows a lower perspective view (e.g., showing downstream surfaces of the implant).

Figure 19:
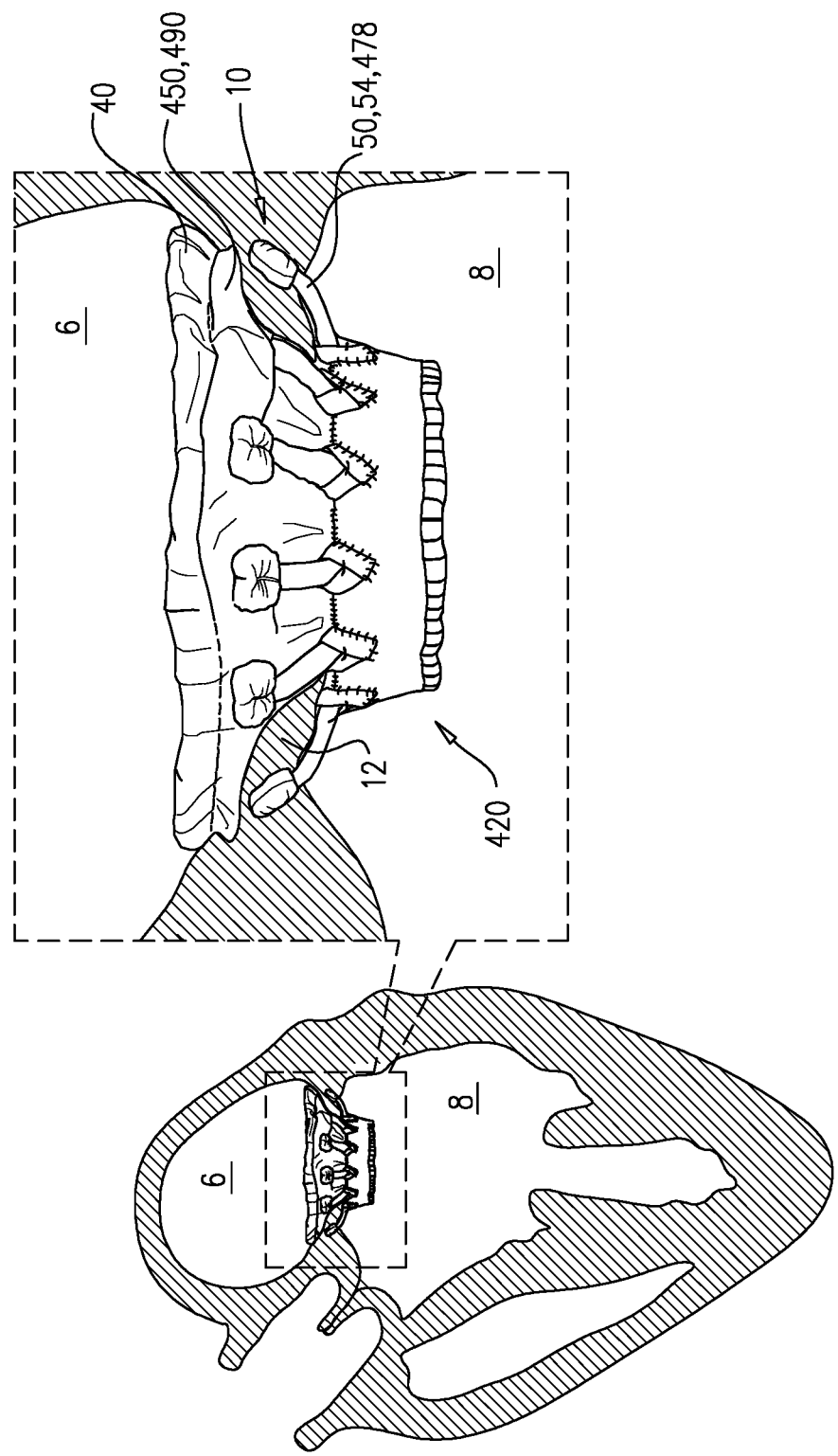

As described with reference to FIGS. 3E-F, implant 20 (which comprises frame assembly 22) is secured in place at the native valve by sandwiching tissue of the native valve between the implant's upstream support portion 40 and flanges 54. Implants that comprise frame assembly 222, such as implant 220, are typically secured in the same way, mutatis mutandis. Implants that further comprise pouch 490, such as implant 420, are typically secured similarly, but with pouch 490 disposed between the upstream support portion and the tissue of the native valve. Therefore in at least some regions of implant 420, the tissue of the native valve is sandwiched between flanges 54 and pouch 490, e.g., as shown in FIG. 19.

Windows 482 open into pouch 490 from the lumen of the valve body. Once implant 420 has been implanted at the native valve, windows 482 are disposed functionally within ventricle 8, whereas at least portions of pouch 490 are disposed functionally within atrium 6. Therefore, during ventricular systole, ventricular pressure (which is much greater than atrial pressure) forces blood into pouch 490, thereby inflating the pouch. This inflation presses pouch 490 against the tissue of the native valve. It is hypothesized by the inventors that this inhibits paravalvular leakage of blood, especially during ventricular systole. For example, the pouch may seal a paravalvular gap at the commissures of the native valve. For some applications, inflation of pouch 490 squeezes tissue of the native valve (e.g., native leaflets) between the pouch and flanges 54. Pouch 490 is typically dimensioned such that, if in a particular region tissue is not disposed between a flange 54 and pouch 490, inflation of the pouch presses the pouch against the flange.

There is therefore provided, in accordance with an application of the present invention, apparatus, comprising:
  a frame assembly (e.g., frame assembly 222) that comprises: (i) a valve body that circumscribes a longitudinal axis and defines a lumen along the axis; (ii) a plurality of arms (e.g., arms 46) that are coupled to the valve body at a first axial level AL1 with respect to the longitudinal axis (e.g., defined by sites 35), each of the arms extending radially outward from the valve body to a respective arm-tip 46*a*; and (iii) a plurality of ventricular legs (e.g., legs 50) that (a) are coupled to the valve body at a second axial level AL2 with respect to the longitudinal axis (e.g., defined by coupling points 52), the second axial level AL2 being downstream of the first axial level AL1 and that (b) extend radially outward from the valve body and toward the plurality of arms;

a tubular liner (e.g., liner 427) that lines the lumen, and that has an upstream end and a downstream end;

a plurality of prosthetic leaflets (e.g., leaflets 58), disposed within the lumen, attached to the liner, and arranged to facilitate one-way upstream-to-downstream fluid flow through the lumen;

a first sheet of flexible material (e.g., sheet 440), the first sheet having (i) a greater perimeter, and (ii) a smaller perimeter that defines an opening, the first sheet being attached to the plurality of arms with the opening aligned with the lumen of the valve body; and a second sheet of flexible material (e.g., sheet 450):
  the second sheet having a first perimeter and a second perimeter,
  the first perimeter being attached to the greater perimeter of the first sheet around the greater perimeter of the first sheet,
  the second sheet extending from the first perimeter radially inwards and downstream toward the second perimeter, the second perimeter circumscribing, and attached to, the valve body at a third axial level that is downstream of the first axial level.

The first sheet, the second sheet, and the liner define inflatable pouch 490 therebetween, the first sheet defining an upstream wall of the pouch, the second sheet defining a radially-outer wall of the pouch, and the liner defining a radially-inner wall of the pouch. The apparatus defines a plurality of windows (e.g., windows 482) from the lumen into the pouch, each of the windows bounded by the liner at upstream edges of the window, and bounded by the second perimeter at a downstream edge of the window. For some applications in which downstream edge 436 of liner 427 is stitched to ring 182 of frame 230, the most upstream parts of windows 482 are closer to the upstream end of the implant than are the most downstream parts of arms 46

Typically, and as shown, pouch 490 circumscribes the valve body of implant 420.

Typically, and as shown in FIG. 18C, each window 482 spans more than one cell of the valve body. This is represented by the multiple instances of reference numeral 482 in FIG. 18C. For some applications, and as shown, each window spans at least partly of five cells of the valve body. For some such applications, and as shown, each window spans substantially all of two cells (e.g., two cells of row 29*a*) and about half (e.g., 40-60 percent) of each of three cells (e.g., three cells of row 29*b*). Each window 482 is bounded by liner 427 at an upstream edge of the window. Typically, and as shown, the upstream edge of each window 482 is defined at rings 182 and 184 of valve frame 230, at which region 428 of liner 427 is stitched to the valve frame. At the downstream edge of each window, the window is bounded by perimeter 452, and also by belt 462. Therefore, at the downstream edge of each window 482, the window may be considered to be bounded by stitch line 465.

For some applications, the upstream edge of each window 482 is the shape of a capital letter M, e.g., with the apices of the letter M at upstream end 34 of the valve body, and with the vertex of the letter M at a site 35. Because region 428 of liner 427 follows, and is stitched to, the joists of valve frame 230 at region 428 of the liner, it is hypothesized by the inventors that this arrangement reinforces the upstream edge of window 482, e.g., increasing durability compared to an arrangement in which the upstream edge of the window crosses between joists of the valve frame.

As described hereinabove, sheet 440 typically covers an upstream side of arms 46. Once pouch 490 has been formed, at least most of each arm 46 is therefore disposed inside the pouch.

For some applications, a circumferential stitch line 445 is used to stitch sheet 440 to sheet 450 at a radius smaller than the overall radius of upstream support portion 40 (i.e., radially inward from the tips of arms 46), typically sandwiching arms 46 between these two sheets. Stitch line 445 is typically radially aligned with region 154 and/or wide (and flexible) portion 46*c* of arm 46. This typically creates a region 484 in which the portions of sheets 440 and 450 that are disposed radially outward from stitch line 445 are isolated from pouch 490. For such applications, the ends of arms 46 are therefore typically disposed in region 484, and are isolated from pouch 490.

For some applications, and as shown, sheet 450 is sufficiently baggy that the sheet (e.g., pouch 490) may extend radially outward beyond arms 46, particularly if uninhibited by tissue of the native valve. This may be achieved by radial dimension d21 of sheet 450 being greater than distance d22 between the ends of arms 46 and clefts 250. For some applications, dimension d21 is more than 30 percent greater (e.g., more than 50 percent greater) than distance d22. For example, dimension d21 may be 30-100 percent greater (e.g., 30-80 percent greater, e.g., 40-80 percent greater, such as 50-70 percent greater) than distance d22. As shown, pouch 490 may extend radially outward beyond arms 46 irrespective of the presence of stitch line 445, which is disposed radially-inward from the ends of arms 46.

Regarding the axial position (i.e., the position along the longitudinal axis of implant 420) of pouch 490 and windows 482. For some applications, pouch 490 extends, with respect to the longitudinal axis of implant 420, further upstream than the leaflets. That is, for some applications, upstream regions of pouch 490 (e.g., those closest to prosthetic valve support 40) are situated further upstream than even the apex of curved edge 456 of leaflets 58. For some applications, and as shown, each of leaflets 58 is attached to liner 427 upstream of windows 482. That is, at least the apex of curved edge 456 of leaflets 58 is disposed upstream of windows 482. Free edge 458 of each leaflet 58 is typically disposed downstream of the third axial level—i.e., the axial level at which perimeter 452 of sheet 450 is attached to frame assembly 222. That is, leaflets 58 typically extend further downstream than pouch 490. For some applications, and as shown, the third axial level (i.e., the axial level at which perimeter 452 of sheet 450 is attached to frame assembly 222) is upstream of the second axial level (i.e., the axial level at which legs 50 are attached to the valve body).

It is to be noted that, whereas liner 427 is disposed on the inside of valve body 32, sheet 450 and belt 462 are disposed on the outside of the valve body. Axially downstream of windows 482, valve body 32 is typically not lined—i.e., no liner is typically disposed between leaflets 58 and frame 30.

It is to be noted that projections 246 are not visible in FIG. 18B. For some applications, and as shown, the projection-length of projections 246 (e.g., see projection-length d13 in FIG. 5C) is such that the projections do not extend further upstream than the tips of arms 46. For some applications, and as shown, projections 246 extend further upstream than the highest part of arms 46 within concave region 152. For some applications, and as shown, projections 246 extend to an axial height that is between (a) that of the tips of arms 46, and (b) that of the highest part of arms 46 within concave region 152. This is illustrated perhaps most clearly in FIG. 9A, which shows inner frame 330a, but is applicable to each of the inner frames described herein, mutatis mutandis.

For some applications of the invention, the scope of the invention includes using one or more of the apparatus and techniques described in this patent application in combination with one or more of the apparatus and techniques described in one or more of the following documents, each of which is incorporated herein by reference:

- U.S. patent application Ser. No. 15/541,783 to Hariton et al., filed Jul. 6, 2017, and entitled "Prosthetic valve with axially-sliding frames," which published as US 2018/0014930 (now U.S. Pat. No. 9,974,651)
- U.S. patent application Ser. No. 15/668,659 to Hariton et al., filed Aug. 3, 2017, and entitled "Techniques for deployment of a prosthetic valve," which published as US 2017/0333187
- U.S. patent application Ser. No. 15/668,559 to Iamberger et al., filed Aug. 3, 2017, and entitled "Prosthetic heart valve" (now U.S. Pat. No. 10,537,426)
- U.S. patent application Ser. No. 15/956,956 to Iamberger et al., filed Apr. 19, 2018, and entitled "Prosthetic heart valve," which published as US 2019/0038405
- U.S. provisional patent application 62/560,384 to Hariton et al., filed Sep. 19, 2017, and entitled "Prosthetic valve and methods of use." Although inventions in the present patent application may also be described in U.S. 62/560,384 (to which priority is claimed), elements that are described in both of these applications may be named differently in one of these applications compared to the other of these applications. For the sake of clarity, element names used in the present application supersede those used in U.S. 62/560,384.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for assembling a prosthetic valve, the method comprising:
    (A) stitching a first sheet of flexible material to a frame assembly, the first sheet having (i) a greater perimeter, and (ii) a smaller perimeter that defines an opening, the frame assembly including:
        a tubular portion that circumscribes a longitudinal axis and defines a lumen along the axis,
        a plurality of arms that are coupled to the tubular portion at a first axial level with respect to the longitudinal axis, each of the arms extending radially outward from the tubular portion to a respective arm-tip, and
        a plurality of ventricular legs that are coupled to the tubular portion at a second axial level with respect to the longitudinal axis, and that extend radially outward from the tubular portion,
    wherein stitching the first sheet to the frame assembly comprises aligning the opening of the first sheet with the lumen and stitching the first sheet onto the plurality of arms;
    (B) subsequently to stitching the first sheet to the plurality of arms, stitching an outer perimeter of a second sheet of flexible material to the greater perimeter of the first sheet, the second sheet being annular, and having an inner perimeter; and
    (C) subsequently to stitching the outer perimeter of the second sheet to the greater perimeter of the first sheet, everting the second sheet by passing the inner perimeter of the second sheet around the arm-tips.

2. The method according to claim 1, further comprising, prior to stitching the first sheet to the plurality of arms:
    obtaining the first sheet while the first sheet is flat, is shaped as a major arc of a ring, and has a first arc-end and a second arc-end; and
    by attaching the first arc-end to the second arc-end, shaping the first sheet into an open frustum that has (i) the greater perimeter at a first base of the frustum, and (ii) the smaller perimeter at a second base of the frustum.

3. The method according to claim 1, further comprising, subsequently to everting the second sheet, stitching the inner perimeter to the tubular portion such that the ventricular legs are disposed radially outside of the second sheet.

4. The method according to claim 1, wherein each of the ventricular legs extends radially outward from the tubular portion at an acute angle to define a respective cleft between the leg and the tubular portion, and everting the second sheet comprises positioning the inner perimeter to circumscribe the tubular portion, and tucking the inner perimeter into the cleft defined by each leg.

5. The method according to claim 1, wherein stitching the outer perimeter of the second sheet to the greater perimeter of the first sheet comprises stitching the outer perimeter of the second sheet to the greater perimeter of the first sheet such that the inner perimeter is disposed axially away from the frame assembly, and wherein everting the second sheet comprises bringing the inner perimeter toward the frame assembly.

6. The method according to claim 1, wherein the arms collectively define an arm-span, and the inner perimeter defines a diameter that is smaller than the arm-span.

7. The method according to claim 6, further comprising temporarily bending at least one arm of the plurality of arms to facilitate passing the inner perimeter of the second sheet around the arms.

8. The method according to claim 1, further comprising securing, within the tubular portion, a valvular assembly that includes a plurality of prosthetic leaflets and a liner, wherein securing the valvular assembly within the tubular portion comprises stitching the liner to the tubular portion, and wherein the method further comprises stitching an upstream edge of the liner to the smaller perimeter of the first sheet.

9. The method according to claim 8, wherein the frame assembly further includes a plurality of projections extending axially away from the tubular portion, and wherein stitching the upstream edge of the liner to the smaller perimeter of the first sheet comprises stitching the upstream edge of the liner to the smaller perimeter of the first sheet such that the projections protrude between the upstream edge of the liner and the smaller perimeter of the first sheet.

10. The method according to claim 1, further comprising:
    obtaining a third sheet of flexible material, the third sheet being flat, and shaped to define (i) a belt, and (ii) a plurality of elongate strips, each of the strips (a) having a first edge, a second edge, and an end, and (b) extending from the belt along a respective strip-axis until the end, the first edge and the second edge extending, on either side of the strip-axis, from the belt to the end of the strip;

for each of the strips, forming the strip into a pocket by:
   folding the strip over itself, about a fold-line that is orthogonal to the strip-axis, thereby forming (i) a first strip-portion that extends from the belt to the fold-line, and (ii) a second strip-portion that extends from the fold-line back toward the belt; and
   stitching together (i) the first strip-portion at the first edge to the second strip-portion at the first edge, and (ii) the first strip-portion at the second edge to the second strip-portion at the second edge, the pocket having (i) an opening defined at least in part by the end of the strip, and (ii) a tip at the fold-line; and
subsequently to forming each of the strips into the corresponding pocket, dressing the frame assembly with the third sheet by:
   sliding each of the ventricular legs into a respective one of the pockets via the opening of the respective one of the pockets; and
   wrapping the belt circumferentially around the tubular portion.

11. The method according to claim 10, further comprising placing a pad inside each pocket at the tip of the pocket.

12. The method according to claim 11, further comprising forming the pad by flattening and folding a piece of foam to form a niche, and wherein sliding each of the ventricular legs into the respective one of the pockets comprises sliding each of the ventricular legs into the respective one of the pockets and into the niche of the respective pad.

13. The method according to claim 1, further comprising, for each of the ventricular legs, wrapping a ribbon around a base of the leg.

14. The method according to claim 13, wherein each of the ventricular legs extends radially outward from the tubular portion at an acute angle to define a cleft between the base of the ventricular leg and the tubular portion, and wherein wrapping the ribbon around the base of the ventricular leg comprises covering the cleft with the ribbon.

15. The method according to claim 1, wherein the tubular portion has an upstream end and a downstream end, and the lumen extends between the upstream end and the downstream end, and wherein the method further comprises securing a polytetrafluoroethylene ring to the downstream end of the tubular portion such that the polytetrafluoroethylene ring circumscribes the lumen at the downstream end.

16. The method according to claim 15, wherein securing the polytetrafluoroethylene ring comprises stitching the polytetrafluoroethylene ring to the downstream end of the valve body using stitches that wrap around the polytetrafluoroethylene ring but do not pierce the polytetrafluoroethylene ring.

\* \* \* \* \*